US007115580B1

(12) United States Patent
Bennett et al.

(10) Patent No.: US 7,115,580 B1
(45) Date of Patent: Oct. 3, 2006

(54) ANTISENSE MODULATION OF B7 PROTEIN EXPRESSION

(75) Inventors: C. Frank Bennett, Carlsbad, CA (US); Timothy A. Vickers, Oceanside, CA (US); James G. Karras, San Marcos, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/980,953

(22) PCT Filed: May 25, 2000

(86) PCT No.: PCT/US00/14471

§ 371 (c)(1),
(2), (4) Date: Apr. 19, 2002

(87) PCT Pub. No.: WO00/74687

PCT Pub. Date: Dec. 14, 2000

Related U.S. Application Data

(63) Continuation-in-part of application No. 09/326,186, filed on Jun. 4, 1999, now Pat. No. 6,319,906, which is a continuation-in-part of application No. 08/777,266, filed on Dec. 31, 1996, now Pat. No. 6,077,833.

(51) Int. Cl.
*A61K 31/7105* (2006.01)
*A61K 31/7115* (2006.01)
*A61K 31/712* (2006.01)
*A61K 31/7125* (2006.01)
*C12Q 1/68* (2006.01)
*C07H 21/02* (2006.01)

(52) U.S. Cl. .......................... 514/44; 435/6; 536/24.5
(58) Field of Classification Search .................. 514/44; 536/24.5; 435/6, 375
See application file for complete search history.

(56) References Cited

U.S. PATENT DOCUMENTS

| 5,585,479 | A | * | 12/1996 | Hoke et al. ..................... 602/6 |
| 5,667,998 | A | * | 9/1997 | Dougherty et al. .......... 435/456 |
| 6,077,833 | A | * | 6/2000 | Bennett et al. ................ 514/44 |
| 6,319,906 | B1 | * | 11/2001 | Bennett et al. ................ 514/44 |

OTHER PUBLICATIONS

Gerwitz, A.M. et al., "Facilitating oligonucleotide delivery: Helping antisense deliver on its promise", 1996, PNAS, vol. 93: pp. 3161-3163.*
Gura, T., "Antisense has growing pains", 1995, Science, vol. 270: pp. 575-577.*
Alberts et al., "*Molecular Biology of the Cell*", 1983, Garland Publishing Inc., New York, pp. 411-415.
Allison et al., "The Yin and Yang of T Cell Costimulation", *Science*, 1995, 270, 932-933.

Allison, J.P, "CD28-B7 interactions in T-cell activation", *Curr. Opin. Immunol.*, 1994, 6, 414.
Azuma et al., "B70 antigen is a second ligand for CTLA-4 and CD28", *Nature*, 1993, 366, 76-79.
Berkow et al., eds., "*The Merck Manual of Diagnosis and Therapy*", 15th Ed., 1987, Rahway, N.J., pp. 302-336 and 2516-2522.
Borriello et al., Characterization of the Murine B7-1 Genomic Locus Reveals an Additional Exon Encoding an Alternative Cytoplasmic Domain and a Chromosomal.
Borriello et al., "Differential Expression of Alternate mB7-2 Transcripts", *J. Immunol.*, 1995, 155, 5490-5497.
Brigstock et al., "Species-Specific High Molecular Weight Forms of Basic Fibroblast Growth Factors", *Growth Factors*, 1990, 4, 45-52.
Charachon et al., "Phosphorothioate Analogues of (2'-5') (A)$_4$: Agonist and Antagonist Activities in Intact Cells", *Biochemistry*, 1990, 29, 2550-2555.
Chen et al., "Monoclonal Antibody 2D10 Recognizes a Novel T cell Costimulatory Molecule on Activated Murine B Lymphocytes", *J. Immunol.*, 1994, 152, 2105-2114.
Chen et al., "Molecular Cloning and Expression of Early T Cell Costimulatory Molecule-1 and its Characterization as B7-2 Molecule", *J. Immunol.*, 1994.
Crooke et al., eds., "Antisense Research and Applications", CRC Press, Boca Raton, 1993, pp. 171-172.
Crooke et al., "Pharmokinetic Properties of Several Novel Oligonucleotide Analogs in mice", *J. Pharmacol. Exp. Ther.*, 1996, 277, 923-937.
DeVirgilio et al., Cloning and Disruption of a Gene Required for Growth on Acetate but not on Ethanol: the Acetyl-Coenzyme A Synthetase Gene of *Saccharomyces*.
Dulbecco et al., "Plaque Production by the Polyoma Virus", *Virol.*, 1959, 8, 396-397.
Freeman et al., "Cloning of B7-2: A CTLA-4 Counter-Receptor That Costimulates Human T Cell Proliferation", *Science*, 1993, 262, 909-911.
Freeman et al., "B7, A New Member of the Ig Superfamily with Unique Expression on Activated and Neoplastic B Cells", *J. Immunol.*, 1989, 143, 2714-2722.
Freeman et al., "Structure, Expression, and T Cell Costimulatory Activity of the Murine Homologue of the Human B Lymphocyte Activation Antigen B7", *J. Exp.*

(Continued)

*Primary Examiner*—Scott D. Priebe
*Assistant Examiner*—Michael Burkhart
(74) *Attorney, Agent, or Firm*—Knobbe Martens Olson & Bear LLP

(57) ABSTRACT

Compositions and methods for the diagnosis, prevention and treatment of immune states and disorders amenable to treatment through modulation of T cell activation are provided. In accordance with preferred embodiments, oligonucleotides are provided which are specifically hybridizable with nucleic acids encoding B7 proteins.

40 Claims, 10 Drawing Sheets

OTHER PUBLICATIONS

French et al., "Express of Two Related Nonstructural Proteins of Bluetongue Virust (BTV) Type 10 in Insect Cells by a Recombinant Baculovirus: Production of Polyclonal Ascitic Fluid and Characterization of the Gene Product in BTV-Infected BHK Cells", J.

Gebeyehu, G., et al., "Novel biotinylated nucleotide—analogs for labeling and colorimetric detection of DNA", *Nucleic Acids Res.*, 1987, 15, 4513-4534.

Gelbert et al., "Analysis of GPT Activity in Mammalian Cells with a Chromosomally Integrated Shuttle Vector Containing Altered gpt Genes", *Somat. Cell. Mol.*

Gold and Stormo, in: *Escherichia coli* and *Salmonella typhimurium: Cellular and Molecular Biology*, vol. 2, 1987.

Hakim et al., "Acute Graft-Versus-Host Reaction Can be Aborted by Blockade of Costimulatory Molecules", *J. Immun.*, 1995, 155, 1760-1766.

Harlan et al., "Mice expressing both B7-1 and viral glycoprotein on pancreatic beta cells along with glycoprotein-specific transgenic T cells develop diabetes due to a breakdown of T-lymphocyte unresponsiveness", *Proc. Natl. Acad. Sci. U.S.A.*, 1994, 91, 3137.

Hathcock et al., "Identification of an Alternative CTLA-4 Ligand Costimulatory for T Cell Activation", *Science*, 1993, 262, 905-907.

Inobe et al., "The Role of the B7-1a Molecule, an Alternatively Spliced Form of Murine B7-1 (CD80), on T Cell Activation", *J. Immun.*, 1996, 157, 582-588.

Jellis et al., "Genomic Organization of the gene coding for the costimulatory human B-lymphocyte antigen B7-2 (CD86)", *Immunogenet.*, 1995, 42, 85.

June et al., "The B7 and CD28 receptor families", *Immunol. Today*, 1994, 15, 321-331.

Kabanov et al., A new class of antivirals: antisense oligonucleotides combined with a hydrophobic substituent effectively inhibit influenza virus reproduction and.

Kanagasundaram et al., "Isolation and characterization of the gene encoding gluconolactonase from *Zymomonas mobilis*", *Biochim. Biophys. Acta*, 1992, 1171, 198-200.

Kornberg, A., DNA Replication, 1974, W.H. Freeman & Co., San Francisco, 1974, pp. 75-77.

Lenschow et al., "Long-Term Survival of Xenogeneic Pancreatic Islet Grafts Induced by CTLA4Ig", 1992, *Science*, 257, 789-792.

Lenschow et al., *Curr. Opin. Immunol.*, 1993, 5(5), 747-52.

Lenschow et al., "Expression and functional significance of an additional ligand for CTLA-4", *Proc. Natl. Acad. Sci. U.S.A.*, 1993, 90, 11054-11058.

Letsinger et al., Cholesteryl-conjugated oligonucleotides: Synthesis, properties, and activity as inhibitors or replication of human immunodeficiency.

Levine et al., "Antiviral Effect and Ex Vivo CD4$^+$ T Cell Proliferation in HIV-Positive Patients as a Result of CD28 Costimulation", *Science*, 1996, 272, 1939-1942.

Lin et al., "Long-Term Acceptance of Major Histocompatibility Complex Mismatched Cardiac Allografts Induced by CTLA4Ig Plus Donor-specific Transfusion", *J.*

Linsley et al., "CTLA-4 Is a Second Receptor for the B Cell Activation Antigen B7", *J. Exp. Med.*, 1991, 174, 561-569.

Linsley et al., "Immunosuppression in Vivo by a Soluble Form of the CTLA-4 T Cell Activation Molecule", *Science*, 1992, 257, 792-795.

Linsley and Ledbetter, "The Role of the CD28 Receptor During T Cell Responses to Antigen", *Annu. Rev. Immunol.*, 1993, 11, 191-212.

Liu and Linsley, "Costimulation of T-cell growth", *Curr. Opin. Immunol.*, 1992, 4, 265-270.

Manoharan et al., "Cholic Acid-Oligonucleotide Conjugates for Antisense Applications", *Bioorg. Med. Chem. Let.*, 1994, 4, 1053-1060.

Manoharan et al., "Oligonucleotide Conjugates: Alteration of the Pharmacokinetic Properties of Antisense Agents", *Nucleosides & Nucleotides*, 1995, 14.

Manoharan et al., "Chemical Modifications to Improve Uptake and Bioavailability of Antisense Oligonucleotides", *Ann. N.Y. Acad. Sci.*, 1992, 660, 306.

Manoharan et al., "Lipidic Nucleic Acids", *Tetrahedron Lett.*, 1995, 36, 3651-3654.

Manoharan et al., Introduction of a Lipophilic Thioether Tether in the Minor Groove of Nucleic Acids for Antisense Applications:, *Bioorg. Med. Chem. Let.*

Markussen et al., "Translational control of oskar generates Short OSK, the isoform that induces pole plasm assembly", *Development*, 1995, 121, 3723-3732.

Martin et al., "Ein neuer Zugang zu 2'-O-Alkyribonucleosiden und Eigenschaften deren Oligonucleotide", *Helv. Chim. Acta*, 1995, 78, 486-504.

McDermott et al., "Stucture and lens expression of the gene encoding chicken βA3/A1-crystallin", *Gene*, 1992, 117, 193.

Mishra et al., "Improved leishmanicidal effect of phosphorotioate antisense oligonucleotides by LDL-mediated delivery", *Biochim. Biophys. Acta*, 1995, 1264.

Monaco et al., "Structure of Two Rat Genes Coding for Closely Related Rolipram-sensitive cAMP Phosphodiesterases", *J. Biol. Chem.*, 1994, 269, 347-357.

Moore et al., "Cell Line Derived from Patient with Myeloma", *N.Y. J. Med.*, 1968, 68, 2054-2060.

Nabavi et al., "Signalling through the MHC class II cytoplasmic domain is required for antigen presentation and induces B7 expression", *Nature*, 1992, 360, 266-268.

Gao et al., Cloning and Characterization of a Mouse Gene with Homology to the Human von Hippel-Lindau Disease Tumor Suppressor Gene: Implications for the Potential Organization of the Human von Hippel.

Nielsen et al., "Sequence-Selective Recognition of DNA by Strand Displacement with a Thymine-Substituted Polyamide", *Science*, 1991, 254, 1497-1500.

Oberhauser et al., Effective incorporation of 2'-O-methyl-oligoribonucleotides into liposomes and enhanced cell association through modification with.

Olsen et al., "Inhibition of Protein Kinanse-A by Overexpression of the Cloned Human Protein Kinase Inhibitor", *Mol. Endocrinol.*, 1991, 5, 1246-1256.

Perri et al., "Interactions of Plasmid-encoded Replication Initiation Proteins with the Origin of DNA Replication in the Broad Host Range Plasmid RK2", J.

Pushpa-Rekha et al., "Rat Phospholipid-hydroperoxide Glutathione Peroxidase", *J. Biol. Chem.*, 1995, 270, 26993.

Reiser et al., "Murine B7 antigen provides an efficient costimulatory signal for activation of murine T lymphocytes via the T-cell", *Proc. Natl. Acad. Sci.*

Rogers et al., "Alternative splicing dictates translational start in Epstein-Barr virus transcripts", *EMBO J.*, 1990, 9, 2273-2277.

Romani et al., "Proliferating Dendritic Cell Progenitors in Human Blood", *J. Exp. Med.*, 1994, 180, 83-93.

Saison-Behmoaras et al., Short modified antisense oligonucleotides directed against Ha-ras point mutation induce selective cleavage of the mRNA and inhibit T24.

Sambrook et al., *Molecular Cloning. A Laboratory Manual*, Cold Spring Harbor Laboratory Press, 1989, vol. 2, p. 10.59-10.61.

Sambrook et al., "Molecular Cloning. A Laboratory Manual," Cold Spring Harbor Laboratory Press, 1989, vol. 2, p. 11.31-11.32.

Saul et al., "celB, a Gene Coding for a Bifunctional Cellulase from the Extreme Thermophile *Caldocellum saccharolyticum*", *Appl. Environ. Microbiol.*, 1990, 56.

Sawai, H., "Synthesis and Properties of Some New 2-5A Analogues", *Chemica Scripta*, 1986, 21, 169-172.

Shea et al., "Synthesis, hybridization properties and antiviral activity of lipid-oligodeoxynucleotide conjugates", *Nucl. Acids Res.*, 1990, 18, 3777-3783.

Smith et al., "The Nucleic Acid of Polyoma Virus" *Virol.*, 1960, 12, 185-196.

Stepkowski et al., Blocking of Heart Allograft Rejection by Intercellular Adhesion Molecule-1 Antisense Oligonucleotides Alone or in Combination with Other.

Svinarchuk et al., "Inhibition of HIV proliferation in MT-4 cells by antisense oligonucleotide conjugated to lipophilic groups", *Biochimie*, 1993, 75, 49-54.

Wu et al., "A Major Costimulatory Molecule on Antigen-presenting Cells, CTLA4 Ligand A, Is Distinct from B7", *J. Exp. Med.*, 1993, 178, 1789-1793.

Yang et al., "CD40 Ligand-Dependent T Cell Activation: Requirement of B7-CD28 Signaling Through CD40", *Science*, 1996, 273, 1862-1864.

Yaoita et al., "*Xenopus laevis* α and β thyroid hormone receptors", *Proc. Natl. Acad. Sci. USA*, 1990, 87, 7090-7094.

* cited by examiner

SEQUENCE LISTING

```
<160> NUMBER OF SEQ ID NOS: 285

<210> SEQ ID NO 1
<211> LENGTH: 32
<212> TYPE: DNA
<213> ORGANISM: Artificial Sequence
<220> FEATURE:
<223> OTHER INFORMATION: Synthetic

<400> SEQUENCE: 1
gatcagggta ccaggagcct taggaggtac gg                              32

<210> SEQ ID NO 2
<211> LENGTH: 33
<212> TYPE: DNA
<213> ORGANISM: Artificial Sequence
<220> FEATURE:
<223> OTHER INFORMATION: Synthetic

<400> SEQUENCE: 2
gatagcctcg agttatttcc aggtcatgag cca                             33

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ttccaggtca tgagccatta                                            20
```

```
<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
cataaggtgt gctctgaagt g                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ttactcatgg taatgtcttt                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
attaaaaaca tgtatcactt                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
ggaacacaga agcaaggtgg t                                              21

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
ccgtacctcc taaggctcct                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
cccatagtgc tgtcacaaat                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic
```

<400> SEQUENCE: 10
gcacagcagc attcccaagg                                                   20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ttgcaaattg gcatggcagg                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
tggtatgggc tttactcttt                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
aaaaggttgc ccaggaacgg                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gggagtcctg gagcccccctt                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ccattaagct gggcttggcc                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
tgcgagctcc ccgtacctcc                                                   20

<210> SEQ ID NO 17

```
<211> LENGTH: 20
<212> TYPE: DNA
<213> ORGANISM: Artificial Sequence
<220> FEATURE:
<223> OTHER INFORMATION: Synthetic
<300> PUBLICATION INFORMATION:
<310> PATENT DOCUMENT NUMBER: US 5514788
<311> PATENT FILING DATE: 1993-05-17
<312> PUBLICATION DATE: 1996-05-07

<400> SEQUENCE: 17
gcccaagctg gcatccgtca                                           20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ggattgccaa gcccatggtg                                           20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ctaagtagtg ctagccggga                                           20

<210> SEQ ID NO 20
<211> LENGTH: 38
<212> TYPE: DNA
<213> ORGANISM: Artificial Sequence
<220> FEATURE:
<223> OTHER INFORMATION: Synthetic

<400> SEQUENCE: 20
gatcagggta ccccaaagaa aaagtgattt gtcattgc                       38

<210> SEQ ID NO 21
<211> LENGTH: 35
<212> TYPE: DNA
<213> ORGANISM: Artificial Sequence
<220> FEATURE:
<223> OTHER INFORMATION: Synthetic

<400> SEQUENCE: 21
gatagcctcg aggataatga attggctgac aagac                          35

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
gggtaagact ccacttctga                                           20

<210> SEQ ID NO 23
<211> LENGTH: 20
<212> TYPE: DNA
<213> ORGANISM: Artificial Sequence
```

```
<220> FEATURE:
<223> OTHER INFORMATION: Synthetic

<400> SEQUENCE: 23
gggtctccaa aggttgtgga                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
gttcctgggt ctccaaaggt                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
acacacagag attggagggt                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gctcacgtag aagaccctcc                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ggcagggctg atgacaatcc                                               20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
tgcaaaacag gcagggctga                                               20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
agaccagggc acttcccagg                                               20
```

```
<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
cctgcctccg tgtgtggccc                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
gaccagccag caccaagagc                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
ccacaggaca gcgttgccac                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
ccggttcttg tactcgggcc                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
ccaaccagga gaggtgaggc                                              20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
ggcaaagcag taggtcaggc                                              20

<210> SEQ ID NO 36
<211> LENGTH: 20
<212> TYPE: DNA
<213> ORGANISM: Artificial Sequence
<220> FEATURE:
<223> OTHER INFORMATION: Synthetic
```

<400> SEQUENCE: 36
gcctcatgat ccccacgatc                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
agtcctacta ccagccgcct                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
tcagggtaag actccacttc                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
agggtgttcc tgggtctcca                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
ctccgtgtgt ggcccatggc                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
ggatggtgat gttccctgcc                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
tgagaaagac cagccagcac                               20

<210> SEQ ID NO 43

```
<211> LENGTH: 20
<212> TYPE: DNA
<213> ORGANISM: Artificial Sequence
<220> FEATURE:
<223> OTHER INFORMATION: Synthetic

<400> SEQUENCE: 43
gggcgcagag ccaggatcac                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
ggcccaggat gggagcaggt                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
agggcgtaca ctttcccttc                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46 cagcccttg cttctgcgga                                                20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
aaggagaggg atgccagcca                                               20

<210> SEQ ID NO 48
<211> LENGTH: 22
<212> TYPE: DNA
<213> ORGANISM: Artificial Sequence
<220> FEATURE:
<223> OTHER INFORMATION: Synthetic

<400> SEQUENCE: 48
ctgttacttt acagagggtt tg                                            22

<210> SEQ ID NO 49
<211> LENGTH: 25
<212> TYPE: DNA
<213> ORGANISM: Artificial Sequence
<220> FEATURE:
<223> OTHER INFORMATION: Synthetic

<400> SEQUENCE: 49
```
cttctgttac tttacagagg gtttg                                          25

<210> SEQ ID NO 50
<211> LENGTH: 21
<212> TYPE: DNA
<213> ORGANISM: Artificial Sequence
<220> FEATURE:
<223> OTHER INFORMATION: Synthetic

<400> SEQUENCE: 50
ctgttacttt acagagggtt t                                              21

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
gccctcgtca gatgggcgca                                                20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
agtcctacta ccagccgcct                                                20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
agtaagagtc tattgaggta                                                20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
ggttgagttt cacaacctga                                                20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
gtccacagaa tggaacagag                                                20

<210> SEQ ID NO 56
<211> LENGTH: 20
<212> TYPE: DNA

<213> ORGANISM: Artificial Sequence
<220> FEATURE:
<223> OTHER INFORMATION: Synthetic

<400> SEQUENCE: 56
ggcatccacc cggcagatgc                                         20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
tggatggcat ccacccggca                                         20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
aggcacctcc taggctcaca                                         20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gccaatggag cttaggcacc                                         20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
catgatgggg aaagccagga                                         20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
aattgcaagc catagcttca                                         20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
cggcaaggca gcaatacctt                                         20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
cccagcaatg acagacagca                                              20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
ggtctgaaag gaccaggccc                                              20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
tgggaaaccc ccggaagcaa                                              20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
ggctttggga aaccccccgga                                             20

<210> SEQ ID NO 67
<211> LENGTH: 19
<212> TYPE: DNA
<213> ORGANISM: Artificial Sequence
<220> FEATURE:
<223> OTHER INFORMATION: Synthetic

<400> SEQUENCE: 67
tcagattcag gatctggga                                               19

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
cccaggtgaa gtcctctgac                                              20

<210> SEQ ID NO 69
<211> LENGTH: 20
<212> TYPE: DNA
<213> ORGANISM: Artificial Sequence
<220> FEATURE:

<223> OTHER INFORMATION: Synthetic

<400> SEQUENCE: 69
ctgcgccgaa tcctgcccca                                                        20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
caggcccgaa ggtaaggctg                                                        20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
tcagctagca cggtgctgaa                                                        20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
ggcccagcaa acttgcccgt                                                        20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
ccaccacagt gggctcagcc                                                        20

<210> SEQ ID NO 74
<211> LENGTH: 19
<212> TYPE: DNA
<213> ORGANISM: Artificial Sequence
<220> FEATURE:
<223> OTHER INFORMATION: Synthetic

<400> SEQUENCE: 74
ggccatgagg gcaatctaa                                                         19

<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
gtggccatga gggcaatcta a                                                      21

```
<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
gatttaacat ttggcgccca                                            20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
aaagttacaa cattatatct                                            20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
agtgcgattc tcaaacctac                                            20

<210> SEQ ID NO 79
<211> LENGTH: 16
<212> TYPE: DNA
<213> ORGANISM: Artificial Sequence
<220> FEATURE:
<223> OTHER INFORMATION: Synthetic

<400> SEQUENCE: 79
tatttgcgag ctcccc                                                16

<210> SEQ ID NO 80
<211> LENGTH: 15
<212> TYPE: DNA
<213> ORGANISM: Artificial Sequence
<220> FEATURE:
<223> OTHER INFORMATION: Synthetic

<400> SEQUENCE: 80
tatttgcgag ctccc                                                 15

<210> SEQ ID NO 81
<211> LENGTH: 14
<212> TYPE: DNA
<213> ORGANISM: Artificial Sequence
<220> FEATURE:
<223> OTHER INFORMATION: Synthetic

<400> SEQUENCE: 81
tatttgcgag ctcc                                                  14

<210> SEQ ID NO 82
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 82
cgacagctcc tgcgctcctc                                          20

<210> SEQ ID NO 83
<211> LENGTH: 16
<212> TYPE: DNA
<213> ORGANISM: Artificial Sequence
<220> FEATURE:
<223> OTHER INFORMATION: Synthetic

<400> SEQUENCE: 83
agctccccgt acctcc                                              16

<210> SEQ ID NO 84
<211> LENGTH: 16
<212> TYPE: DNA
<213> ORGANISM: Artificial Sequence
<220> FEATURE:
<223> OTHER INFORMATION: Synthetic

<400> SEQUENCE: 84
tgcgagctcc ccgtac                                              16

<210> SEQ ID NO 85
<211> LENGTH: 10
<212> TYPE: DNA
<213> ORGANISM: Artificial Sequence
<220> FEATURE:
<223> OTHER INFORMATION: Synthetic

<400> SEQUENCE: 85
ctccccgtac                                                     10

<210> SEQ ID NO 86
<211> LENGTH: 11
<212> TYPE: DNA
<213> ORGANISM: Artificial Sequence
<220> FEATURE:
<223> OTHER INFORMATION: Synthetic

<400> SEQUENCE: 86
gctccccgta c                                                   11

<210> SEQ ID NO 87
<211> LENGTH: 12
<212> TYPE: DNA
<213> ORGANISM: Artificial Sequence
<220> FEATURE:
<223> OTHER INFORMATION: Synthetic

<400> SEQUENCE: 87
agctccccgt ac                                                  12

<210> SEQ ID NO 88
<211> LENGTH: 13
<212> TYPE: DNA
<213> ORGANISM: Artificial Sequence
<220> FEATURE:
<223> OTHER INFORMATION: Synthetic

<400> SEQUENCE: 88
gagctccccg tac                                                 13

<210> SEQ ID NO 89
<211> LENGTH: 14
```

```
<212> TYPE: DNA
<213> ORGANISM: Artificial Sequence
<220> FEATURE:
<223> OTHER INFORMATION: Synthetic

<400> SEQUENCE: 89
cgagctcccc gtac                                                        14

<210> SEQ ID NO 90
<211> LENGTH: 15
<212> TYPE: DNA
<213> ORGANISM: Artificial Sequence
<220> FEATURE:
<223> OTHER INFORMATION: Synthetic

<400> SEQUENCE: 90
gcgagctccc cgtac                                                       15

<210> SEQ ID NO 91
<211> LENGTH: 13
<212> TYPE: DNA
<213> ORGANISM: Artificial Sequence
<220> FEATURE:
<223> OTHER INFORMATION: Synthetic

<400> SEQUENCE: 91
gcgagctccc cgt                                                         13

<210> SEQ ID NO 92
<211> LENGTH: 15
<212> TYPE: DNA
<213> ORGANISM: Artificial Sequence
<220> FEATURE:
<223> OTHER INFORMATION: Synthetic

<400> SEQUENCE: 92
gccgccgcca agtct                                                       15

<210> SEQ ID NO 93
<211> LENGTH: 24
<212> TYPE: DNA
<213> ORGANISM: Artificial Sequence
<220> FEATURE:
<223> OTHER INFORMATION: Synthetic

<400> SEQUENCE: 93
gagaagcaaa gctttcaccc tgtg                                             24

<210> SEQ ID NO 94
<211> LENGTH: 22
<212> TYPE: DNA
<213> ORGANISM: Artificial Sequence
<220> FEATURE:
<223> OTHER INFORMATION: Synthetic

<400> SEQUENCE: 94
gaagcaaagc tttcaccctg tg                                               22

<210> SEQ ID NO 95
<211> LENGTH: 19
<212> TYPE: DNA
<213> ORGANISM: Artificial Sequence
<220> FEATURE:
<223> OTHER INFORMATION: Synthetic

<400> SEQUENCE: 95
```
gcaaagcttt caccctgtg                                             19

<210> SEQ ID NO 96
<211> LENGTH: 24
<212> TYPE: DNA
<213> ORGANISM: Artificial Sequence
<220> FEATURE:
<223> OTHER INFORMATION: Synthetic

<400> SEQUENCE: 96
ctccccgtac ctcctaaggc tcct                                       24

<210> SEQ ID NO 97
<211> LENGTH: 22
<212> TYPE: DNA
<213> ORGANISM: Artificial Sequence
<220> FEATURE:
<223> OTHER INFORMATION: Synthetic

<400> SEQUENCE: 97
ccccgtacct cctaaggctc ct                                         22

<210> SEQ ID NO 98
<211> LENGTH: 19
<212> TYPE: DNA
<213> ORGANISM: Artificial Sequence
<220> FEATURE:
<223> OTHER INFORMATION: Synthetic

<400> SEQUENCE: 98
ccgtacctcc taaggctcc                                             19

<210> SEQ ID NO 99
<211> LENGTH: 32
<212> TYPE: DNA
<213> ORGANISM: Artificial Sequence
<220> FEATURE:
<223> OTHER INFORMATION: Synthetic

<400> SEQUENCE: 99
gatcagggta ccaagagtgg ctcctgtagg ca                              32

<210> SEQ ID NO 100
<211> LENGTH: 32
<212> TYPE: DNA
<213> ORGANISM: Artificial Sequence
<220> FEATURE:
<223> OTHER INFORMATION: Synthetic

<400> SEQUENCE: 100
gatagcctcg aggtagaatt ccaatcagct ga                              32

<210> SEQ ID NO 101
<211> LENGTH: 20
<212> TYPE: DNA
<213> ORGANISM: Artificial Sequence
<220> FEATURE:
<223> OTHER INFORMATION: Synthetic
<300> PUBLICATION INFORMATION:
<302> TITLE: Blocking of Heart Allograft Rejection by Intercellular
      Adhesion Molecule-1 Synthetic Alone or
      in Combination with Other Immunosupprssive Modalities
<303> JOURNAL: J. Immunol.
<304> VOLUME: 153
<306> PAGES: 5336-5346
<307> DATE: 1994-12-01

<400> SEQUENCE: 101
tgcatccccc aggccaccat                                           20

<210> SEQ ID NO 102
<211> LENGTH: 21
<212> TYPE: DNA
<213> ORGANISM: Artificial Sequence
<220> FEATURE:
<223> OTHER INFORMATION: Synthetic
<300> PUBLICATION INFORMATION:
<302> TITLE: Blocking of Heart Allograft Rejection by Intercellular
      Adhesion Molecule-1 Synthetic Alone or
      in Combination with Other Immunosupprssive Modalities
<303> JOURNAL: J. Immunol.
<304> VOLUME: 153
<306> PAGES: 5336-5346
<307> DATE: 1994-12-01

<400> SEQUENCE: 102
gccgaggtcc atgtcgtacg c                                         21

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
acacgtctac aggagtctgg                                           20

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
caagcccatg gtgcatctgg                                           20

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
ctggggtcca tcgtgggtgc                                           20

<210> SEQ ID NO 106
<211> LENGTH: 20
<212> TYPE: DNA
<213> ORGANISM: Artificial Sequence
<220> FEATURE:
<223> OTHER INFORMATION: Synthetic

<400> SEQUENCE: 106
ccgtgctgcc tacaggagcc                                           20

<210> SEQ ID NO 107
<211> LENGTH: 20
<212> TYPE: DNA
<213> ORGANISM: Artificial Sequence
<220> FEATURE:
<223> OTHER INFORMATION: Synthetic

```
<400> SEQUENCE: 107
ggtgcttccg taagttctgg                                               20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
ggattgccaa gcccatggtg                                               20

<210> SEQ ID NO 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
ctaagtagtg ctagccggga                                               20

<210> SEQ ID NO 110
<211> LENGTH: 20
<212> TYPE: DNA
<213> ORGANISM: Artificial Sequence
<220> FEATURE:
<223> OTHER INFORMATION: Synthetic

<400> SEQUENCE: 110
tgcgtctcca cggaaacagc                                               20

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
gtgcggccca ggtacttggc                                               20

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
acaaggagga gggccacagt                                               20

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
tgagaggttt ggaggaaatc                                               20

<210> SEQ ID NO 114
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 114
gatagtctct ctgtcagcgt                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
gttgctgggc ctgctaggct                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
ctaggtctcg tcgtcggtgg                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
tctcactgcc ttcactctgc                                               20

<210> SEQ ID NO 118
<211> LENGTH: 21
<212> TYPE: DNA
<213> ORGANISM: Artificial Sequence
<220> FEATURE:
<223> OTHER INFORMATION: Synthetic

<400> SEQUENCE: 118
gtaccagatg aaggttatca a                                             21

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
ctttggagat tattcgagtt                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
```
gcaagtgtaa agccctgagt                                              20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
agaattccaa tcagctgaga                                              20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
tctgagaaac tctgcacttc                                              20

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
tcctcaggct ctcactgcct                                              20

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
ggttgttcaa gtccgtgctg                                              20

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125
gccgaggtcc atgtcgtagc c                                            21

<210> SEQ ID NO 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
agactccact tctgagatgt                                              20

<210> SEQ ID NO 127
<211> LENGTH: 20
<212> TYPE: DNA
<213> ORGANISM: Artificial Sequence

```
<220> FEATURE:
<223> OTHER INFORMATION: Synthetic

<400> SEQUENCE: 127
tgaagaaaaa ttccactttt                                               20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
tttagtttca cagcttgctg                                               20

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
tcccaggtgc aaaacaggca                                               20

<210> SEQ ID NO 130
<211> LENGTH: 20
<212> TYPE: DNA
<213> ORGANISM: Artificial Sequence
<220> FEATURE:
<223> OTHER INFORMATION: Synthetic

<400> SEQUENCE: 130
gtgaaagcca acaatttgga                                               20

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
catggcttca gatgcttagg                                               20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
ttgaggtatg gacacttgga                                               20

<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
gcgttgccac ttctttcact                                               20
```

```
<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
ttttgccagt agatgcgagt                                             20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
ggccatatat tcatgtcccc                                             20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
gccaggatca caatggagag                                             20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
gtatgtgccc tcgtcagatg                                             20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
ttcagccagg tgttcccgct                                             20

<210> SEQ ID NO 139
<211> LENGTH: 20
<212> TYPE: DNA
<213> ORGANISM: Artificial Sequence
<220> FEATURE:
<223> OTHER INFORMATION: Synthetic

<400> SEQUENCE: 139
ggaagtcagc tttgactgat                                             20

<210> SEQ ID NO 140
<211> LENGTH: 20
<212> TYPE: DNA
<213> ORGANISM: Artificial Sequence
<220> FEATURE:
<223> OTHER INFORMATION: Synthetic
```

<400> SEQUENCE: 140
cctccagagg ttgagcaaat                                           20

<210> SEQ ID NO 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
ccaaccagga gaggtgaggc                                           20

<210> SEQ ID NO 142
<211> LENGTH: 20
<212> TYPE: DNA
<213> ORGANISM: Artificial Sequence
<220> FEATURE:
<223> OTHER INFORMATION: Synthetic

<400> SEQUENCE: 142
gaagctgtgg ttggttgtca                                           20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
ttgaaggtct gattcactct                                           20

<210> SEQ ID NO 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
aaggtaatgg cccaggatgg                                           20

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
aagcagtagg tcaggcagca                                           20

<210> SEQ ID NO 146
<211> LENGTH: 20
<212> TYPE: DNA
<213> ORGANISM: Artificial Sequence
<220> FEATURE:
<223> OTHER INFORMATION: Synthetic

<400> SEQUENCE: 146
ccttgcttct gcggacactg                                           20

<210> SEQ ID NO 147

```
<211> LENGTH: 20
<212> TYPE: DNA
<213> ORGANISM: Artificial Sequence
<220> FEATURE:
<223> OTHER INFORMATION: Synthetic

<400> SEQUENCE: 147
agccccttgc ttctgcggac                                                  20

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
tgacggaggc taccttcaga                                                  20

<210> SEQ ID NO 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
gtaaaacagc ttaaatttgt                                                  20

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
agaagaggtt acattaagca                                                  20

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
agataatgaa ttggctgaca                                                  20

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
gcgtcatcat ccgcaccatc                                                  20

<210> SEQ ID NO 153
<211> LENGTH: 20
<212> TYPE: DNA
<213> ORGANISM: Artificial Sequence
<220> FEATURE:
<223> OTHER INFORMATION: Synthetic

<400> SEQUENCE: 153
```
cgttgcttgt gccgacagtg                                          20

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
gctcacgaag aacaccttcc                                          20

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
agagaaacta gtaagagtct                                          20

<210> SEQ ID NO 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
tggcatccac ccggcagatg                                          20

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
tcgagaaaca gagatgtaga                                          20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
tggagcttag gcacctccta                                          20

<210> SEQ ID NO 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
tggggaaagc caggaatcta                                          20

<210> SEQ ID NO 160
<211> LENGTH: 20
<212> TYPE: DNA

```
<213> ORGANISM: Artificial Sequence
<220> FEATURE:
<223> OTHER INFORMATION: Synthetic

<400> SEQUENCE: 160
cagcacaaag agaagaatga                                              20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
atgaggagag ttgtaacggc                                              20

<210> SEQ ID NO 162
<211> LENGTH: 20
<212> TYPE: DNA
<213> ORGANISM: Artificial Sequence
<220> FEATURE:
<223> OTHER INFORMATION: Synthetic

<400> SEQUENCE: 162
aagtccggtt cttatactcg                                              20

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
gcaggtaatc cttttagtgt                                              20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
gtgaagtcct ctgacacgtg                                              20

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
cgaatcctgc cccaaagagc                                              20

<210> SEQ ID NO 166
<211> LENGTH: 20
<212> TYPE: DNA
<213> ORGANISM: Artificial Sequence
<220> FEATURE:
<223> OTHER INFORMATION: Synthetic

<400> SEQUENCE: 166
actgcgccga atcctgcccc                                              20
```

<210> SEQ ID NO 167
<211> LENGTH: 20
<212> TYPE: DNA
<213> ORGANISM: Artificial Sequence
<220> FEATURE:
<223> OTHER INFORMATION: Synthetic

<400> SEQUENCE: 167
ttgatgatga caacgatgac                                       20

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
ctgttgtttg tttctctgct                                       20

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
tgttcagcta atgcttcttc                                       20

<210> SEQ ID NO 170
<211> LENGTH: 20
<212> TYPE: DNA
<213> ORGANISM: Artificial Sequence
<220> FEATURE:
<223> OTHER INFORMATION: Synthetic

<400> SEQUENCE: 170
gttaactcta tcttgtgtca                                       20

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
tccacttcag tcatcaagca                                       20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
tgctcaatac tctcttttta                                       20

<210> SEQ ID NO 173
<211> LENGTH: 20
<212> TYPE: DNA
<213> ORGANISM: Artificial Sequence
<220> FEATURE:

-continued

<223> OTHER INFORMATION: Synthetic

<400> SEQUENCE: 173
aggcccagca aacttgcccg 20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
aacggcaagg cagcaatacc 20

<210> SEQ ID NO 175
<211> LENGTH: 20
<212> TYPE: DNA
<213> ORGANISM: Artificial Sequence
<220> FEATURE:
<223> OTHER INFORMATION: Synthetic

<400> SEQUENCE: 175
cagaagcaag gtggtaagaa 20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
gcctgtccac tgtagctcca 20

<210> SEQ ID NO 177
<211> LENGTH: 20
<212> TYPE: DNA
<213> ORGANISM: Artificial Sequence
<220> FEATURE:
<223> OTHER INFORMATION: Synthetic

<400> SEQUENCE: 177
agaatgttac tcagtcccat 20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
tcagaggagc agcaccagag 20

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
tggcatggca ggtctgcagt 20

```
<210> SEQ ID NO 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
agctcactca ggctttggtt                                            20

<210> SEQ ID NO 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
tgcctaagta tacctcattc                                            20

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
ctgtcaaatt tctctttgcc                                            20

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
catatacttg gaatgaacac                                            20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
ggtccaactg tccgaatcaa                                            20

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
tgatctgaag attgtgaagt                                            20

<210> SEQ ID NO 186
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 186
aagcccttgt ccttgatctg                                          20

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
tgtgatggat gatacattga                                          20

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
tcaggttgac tgaagttagc                                          20

<210> SEQ ID NO 189
<211> LENGTH: 20
<212> TYPE: DNA
<213> ORGANISM: Artificial Sequence
<220> FEATURE:
<223> OTHER INFORMATION: Synthetic

<400> SEQUENCE: 189
gtgtatagat gagcaggtca                                          20

<210> SEQ ID NO 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
tctgtgacat tatcttgaga                                          20

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
aagataaaag ccgcgtcttg                                          20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
agaaaaccat cacacatata                                          20

<210> SEQ ID NO 193
<211> LENGTH: 20
```

```
<212> TYPE: DNA
<213> ORGANISM: Artificial Sequence
<220> FEATURE:
<223> OTHER INFORMATION: Synthetic

<400> SEQUENCE: 193
agagttgcga ggccgcttct                                              20

<210> SEQ ID NO 194
<211> LENGTH: 20
<212> TYPE: DNA
<213> ORGANISM: Artificial Sequence
<220> FEATURE:
<223> OTHER INFORMATION: Synthetic

<400> SEQUENCE: 194
tccctctcca ttgtgttggt                                              20

<210> SEQ ID NO 195
<211> LENGTH: 20
<212> TYPE: DNA
<213> ORGANISM: Artificial Sequence
<220> FEATURE:
<223> OTHER INFORMATION: Synthetic

<400> SEQUENCE: 195
catcagatct ttcaggtata                                              20

<210> SEQ ID NO 196
<211> LENGTH: 20
<212> TYPE: DNA
<213> ORGANISM: Artificial Sequence
<220> FEATURE:
<223> OTHER INFORMATION: Synthetic

<400> SEQUENCE: 196
ggctttactc tttaattaaa                                              20

<210> SEQ ID NO 197
<211> LENGTH: 20
<212> TYPE: DNA
<213> ORGANISM: Artificial Sequence
<220> FEATURE:
<223> OTHER INFORMATION: Synthetic

<400> SEQUENCE: 197
gaaatcaaaa aggttgccca                                              20

<210> SEQ ID NO 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
ggagtcctgg agccccctta                                              20

<210> SEQ ID NO 199
<211> LENGTH: 20
<212> TYPE: DNA
<213> ORGANISM: Artificial Sequence
<220> FEATURE:
<223> OTHER INFORMATION: Synthetic

<400> SEQUENCE: 199
```
ttggcatacg gagcagagct                                              20

<210> SEQ ID NO 200
<211> LENGTH: 20
<212> TYPE: DNA
<213> ORGANISM: Artificial Sequence
<220> FEATURE:
<223> OTHER INFORMATION: Synthetic

<400> SEQUENCE: 200
tgtgctctga agtgaaaaga                                              20

<210> SEQ ID NO 201
<211> LENGTH: 20
<212> TYPE: DNA
<213> ORGANISM: Artificial Sequence
<220> FEATURE:
<223> OTHER INFORMATION: Synthetic

<400> SEQUENCE: 201
ggcttggccc ataagtgtgc                                              20

<210> SEQ ID NO 202
<211> LENGTH: 20
<212> TYPE: DNA
<213> ORGANISM: Artificial Sequence
<220> FEATURE:
<223> OTHER INFORMATION: Synthetic

<400> SEQUENCE: 202
cctaaatttt atttccaggt                                              20

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
gctccaagtg tcccaatgaa                                              20

<210> SEQ ID NO 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
agtatgtttc tcactccgat                                              20

<210> SEQ ID NO 205
<211> LENGTH: 20
<212> TYPE: DNA
<213> ORGANISM: Artificial Sequence
<220> FEATURE:
<223> OTHER INFORMATION: control oligonucleotide

<400> SEQUENCE: 205
tgccagcacc cggtacgtcc                                              20

<210> SEQ ID NO 206
<211> LENGTH: 20
<212> TYPE: DNA
<213> ORGANISM: Artificial Sequence

```
<220> FEATURE:
<223> OTHER INFORMATION: Synthetic

<400> SEQUENCE: 206
gctgcctaca ggagccactc                                              20

<210> SEQ ID NO 207
<211> LENGTH: 20
<212> TYPE: DNA
<213> ORGANISM: Artificial Sequence
<220> FEATURE:
<223> OTHER INFORMATION: Synthetic

<400> SEQUENCE: 207
tcaagtccgt gctgcctaca                                              20

<210> SEQ ID NO 208
<211> LENGTH: 20
<212> TYPE: DNA
<213> ORGANISM: Artificial Sequence
<220> FEATURE:
<223> OTHER INFORMATION: Synthetic

<400> SEQUENCE: 208
gtctacagga gtctggttgt                                              20

<210> SEQ ID NO 209
<211> LENGTH: 20
<212> TYPE: DNA
<213> ORGANISM: Artificial Sequence
<220> FEATURE:
<223> OTHER INFORMATION: Synthetic

<400> SEQUENCE: 209
agcttgcgtc tccacggaaa                                              20

<210> SEQ ID NO 210
<211> LENGTH: 20
<212> TYPE: DNA
<213> ORGANISM: Artificial Sequence
<220> FEATURE:
<223> OTHER INFORMATION: Synthetic

<400> SEQUENCE: 210
tcacactatc aagtttctct                                              20

<210> SEQ ID NO 211
<211> LENGTH: 20
<212> TYPE: DNA
<213> ORGANISM: Artificial Sequence
<220> FEATURE:
<223> OTHER INFORMATION: Synthetic

<400> SEQUENCE: 211
gtcaaagctc gtgcggccca                                              20

<210> SEQ ID NO 212
<211> LENGTH: 20
<212> TYPE: DNA
<213> ORGANISM: Artificial Sequence
<220> FEATURE:
<223> OTHER INFORMATION: Synthetic

<400> SEQUENCE: 212
gtgaagtcgt agagtccagt                                              20
```

<210> SEQ ID NO 213
<211> LENGTH: 20
<212> TYPE: DNA
<213> ORGANISM: Artificial Sequence
<220> FEATURE:
<223> OTHER INFORMATION: Synthetic

<400> SEQUENCE: 213
gtgaccttgc ttagacgtgc                                              20

<210> SEQ ID NO 214
<211> LENGTH: 20
<212> TYPE: DNA
<213> ORGANISM: Artificial Sequence
<220> FEATURE:
<223> OTHER INFORMATION: Synthetic

<400> SEQUENCE: 214
catcttctta ggtttcgggt                                              20

<210> SEQ ID NO 215
<211> LENGTH: 20
<212> TYPE: DNA
<213> ORGANISM: Artificial Sequence
<220> FEATURE:
<223> OTHER INFORMATION: Synthetic

<400> SEQUENCE: 215
ggctgttgga gatactgaac                                              20

<210> SEQ ID NO 216
<211> LENGTH: 20
<212> TYPE: DNA
<213> ORGANISM: Artificial Sequence
<220> FEATURE:
<223> OTHER INFORMATION: Synthetic

<400> SEQUENCE: 216
gggaatgaaa gagagaggct                                              20

<210> SEQ ID NO 217
<211> LENGTH: 20
<212> TYPE: DNA
<213> ORGANISM: Artificial Sequence
<220> FEATURE:
<223> OTHER INFORMATION: Synthetic

<400> SEQUENCE: 217
acatacaatg atgagcagca                                              20

<210> SEQ ID NO 218
<211> LENGTH: 20
<212> TYPE: DNA
<213> ORGANISM: Artificial Sequence
<220> FEATURE:
<223> OTHER INFORMATION: Synthetic

<400> SEQUENCE: 218
gtctctctgt cagcgttact                                              20

<210> SEQ ID NO 219
<211> LENGTH: 20
<212> TYPE: DNA
<213> ORGANISM: Artificial Sequence
<220> FEATURE:
<223> OTHER INFORMATION: Synthetic

```
<400> SEQUENCE: 219
tgccaagccc atggtgcatc                                                 20

<210> SEQ ID NO 220
<211> LENGTH: 20
<212> TYPE: DNA
<213> ORGANISM: Artificial Sequence
<220> FEATURE:
<223> OTHER INFORMATION: Synthetic

<400> SEQUENCE: 220
gcaatttggg gttcaagttc                                                 20

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
caatcagctg agaacatttt                                                 20

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
ttttgtataa aacaatcata                                                 20

<210> SEQ ID NO 223
<211> LENGTH: 20
<212> TYPE: DNA
<213> ORGANISM: Artificial Sequence
<220> FEATURE:
<223> OTHER INFORMATION: Synthetic

<400> SEQUENCE: 223
ccttcactct gcatttggtt                                                 20

<210> SEQ ID NO 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
tgcatgttat caccatactc                                                 20

<210> SEQ ID NO 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
ccctccagtg atgtttacaa                                                 20

<210> SEQ ID NO 226
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 226
gaagaccctc cagtgatgtt                                               20

<210> SEQ ID NO 227
<211> LENGTH: 20
<212> TYPE: DNA
<213> ORGANISM: Artificial Sequence
<220> FEATURE:
<223> OTHER INFORMATION: Synthetic

<400> SEQUENCE: 227
cgtagaagac cctccagtga                                               20

<210> SEQ ID NO 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
ttcccaggtg caaaacaggc                                               20

<210> SEQ ID NO 229
<211> LENGTH: 20
<212> TYPE: DNA
<213> ORGANISM: Artificial Sequence
<220> FEATURE:
<223> OTHER INFORMATION: Synthetic

<400> SEQUENCE: 229
tggcttcaga tgcttagggt                                               20

<210> SEQ ID NO 230
<211> LENGTH: 20
<212> TYPE: DNA
<213> ORGANISM: Artificial Sequence
<220> FEATURE:
<223> OTHER INFORMATION: Synthetic

<400> SEQUENCE: 230
cctccgtgtg tggcccatgg                                               20

<210> SEQ ID NO 231
<211> LENGTH: 20
<212> TYPE: DNA
<213> ORGANISM: Artificial Sequence
<220> FEATURE:
<223> OTHER INFORMATION: Synthetic

<400> SEQUENCE: 231
ggtgatgttc cctgcctccg                                               20

<210> SEQ ID NO 232
<211> LENGTH: 20
<212> TYPE: DNA
<213> ORGANISM: Artificial Sequence
<220> FEATURE:
<223> OTHER INFORMATION: Synthetic

<400> SEQUENCE: 232
```
gatggtgatg ttccctgcct                                          20

<210> SEQ ID NO 233
<211> LENGTH: 20
<212> TYPE: DNA
<213> ORGANISM: Artificial Sequence
<220> FEATURE:
<223> OTHER INFORMATION: Synthetic

<400> SEQUENCE: 233
aggtatggac acttggatgg                                          20

<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
gaaagaccag ccagcaccaa                                          20

<210> SEQ ID NO 235
<211> LENGTH: 20
<212> TYPE: DNA
<213> ORGANISM: Artificial Sequence
<220> FEATURE:
<223> OTHER INFORMATION: Synthetic

<400> SEQUENCE: 235
cagcgttgcc acttctttca                                          20

<210> SEQ ID NO 236
<211> LENGTH: 20
<212> TYPE: DNA
<213> ORGANISM: Artificial Sequence
<220> FEATURE:
<223> OTHER INFORMATION: Synthetic

<400> SEQUENCE: 236
gtgaccacag gacagcgttg                                          20

<210> SEQ ID NO 237
<211> LENGTH: 20
<212> TYPE: DNA
<213> ORGANISM: Artificial Sequence
<220> FEATURE:
<223> OTHER INFORMATION: Synthetic

<400> SEQUENCE: 237
agatgcgagt ttgtgccagc                                          20

<210> SEQ ID NO 238
<211> LENGTH: 20
<212> TYPE: DNA
<213> ORGANISM: Artificial Sequence
<220> FEATURE:
<223> OTHER INFORMATION: Synthetic

<400> SEQUENCE: 238
ccttttgcca gtagatgcga                                          20

<210> SEQ ID NO 239
<211> LENGTH: 20
<212> TYPE: DNA

<213> ORGANISM: Artificial Sequence
<220> FEATURE:
<223> OTHER INFORMATION: Synthetic

<400> SEQUENCE: 239
cggttcttgt actcgggcca                                               20

<210> SEQ ID NO 240
<211> LENGTH: 20
<212> TYPE: DNA
<213> ORGANISM: Artificial Sequence
<220> FEATURE:
<223> OTHER INFORMATION: Synthetic

<400> SEQUENCE: 240
cgcagagcca ggatcacaat                                               20

<210> SEQ ID NO 241
<211> LENGTH: 20
<212> TYPE: DNA
<213> ORGANISM: Artificial Sequence
<220> FEATURE:
<223> OTHER INFORMATION: Synthetic

<400> SEQUENCE: 241
cttcagccag gtgttcccgc                                               20

<210> SEQ ID NO 242
<211> LENGTH: 20
<212> TYPE: DNA
<213> ORGANISM: Artificial Sequence
<220> FEATURE:
<223> OTHER INFORMATION: Synthetic

<400> SEQUENCE: 242
taacgtcact tcagccaggt                                               20

<210> SEQ ID NO 243
<211> LENGTH: 20
<212> TYPE: DNA
<213> ORGANISM: Artificial Sequence
<220> FEATURE:
<223> OTHER INFORMATION: Synthetic

<400> SEQUENCE: 243
ttctccattt tccaaccagg                                               20

<210> SEQ ID NO 244
<211> LENGTH:
<212> TYPE:
<213> ORGANISM:

<400> SEQUENCE: 244

000

<210> SEQ ID NO 245
<211> LENGTH: 20
<212> TYPE: DNA
<213> ORGANISM: Artificial Sequence
<220> FEATURE:
<223> OTHER INFORMATION: Synthetic

<400> SEQUENCE: 245
ctgttgtgtt gatggcattt                                               20

```
<210> SEQ ID NO 246
<211> LENGTH: 20
<212> TYPE: DNA
<213> ORGANISM: Artificial Sequence
<220> FEATURE:
<223> OTHER INFORMATION: Synthetic

<400> SEQUENCE: 246
catgaagctg tggttggttg                                                    20

<210> SEQ ID NO 247
<211> LENGTH: 20
<212> TYPE: DNA
<213> ORGANISM: Artificial Sequence
<220> FEATURE:
<223> OTHER INFORMATION: Synthetic

<400> SEQUENCE: 247
aggaaaatgc tcttgcttgg                                                    20

<210> SEQ ID NO 248
<211> LENGTH: 20
<212> TYPE: DNA
<213> ORGANISM: Artificial Sequence
<220> FEATURE:
<223> OTHER INFORMATION: Synthetic

<400> SEQUENCE: 248
tgggagcagg ttatcaggaa                                                    20

<210> SEQ ID NO 249
<211> LENGTH: 20
<212> TYPE: DNA
<213> ORGANISM: Artificial Sequence
<220> FEATURE:
<223> OTHER INFORMATION: Synthetic

<400> SEQUENCE: 249
taaggtaatg gcccaggatg                                                    20

<210> SEQ ID NO 250
<211> LENGTH: 20
<212> TYPE: DNA
<213> ORGANISM: Artificial Sequence
<220> FEATURE:
<223> OTHER INFORMATION: Synthetic

<400> SEQUENCE: 250
ggtcaggcag catatcacaa                                                    20

<210> SEQ ID NO 251
<211> LENGTH: 20
<212> TYPE: DNA
<213> ORGANISM: Artificial Sequence
<220> FEATURE:
<223> OTHER INFORMATION: Synthetic

<400> SEQUENCE: 251
gccccttgct tgtgcggaca                                                    20

<210> SEQ ID NO 252
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 252
agatcttttc agccccttgc                                               20

<210> SEQ ID NO 253
<211> LENGTH: 20
<212> TYPE: DNA
<213> ORGANISM: Artificial Sequence
<220> FEATURE:
<223> OTHER INFORMATION: Synthetic

<400> SEQUENCE: 253
tttgttaagg gaagaatgcc                                               20

<210> SEQ ID NO 254
<211> LENGTH: 20
<212> TYPE: DNA
<213> ORGANISM: Artificial Sequence
<220> FEATURE:
<223> OTHER INFORMATION: Synthetic

<400> SEQUENCE: 254
aaaggagagg gatgccagcc                                               20

<210> SEQ ID NO 255
<211> LENGTH: 20
<212> TYPE: DNA
<213> ORGANISM: Artificial Sequence
<220> FEATURE:
<223> OTHER INFORMATION: Synthetic

<400> SEQUENCE: 255
caagacaatt caagatggca                                               20

<210> SEQ ID NO 256
<211> LENGTH: 20
<212> TYPE: DNA
<213> ORGANISM: Artificial Sequence
<220> FEATURE:
<223> OTHER INFORMATION: Synthetic

<400> SEQUENCE: 256
cgtgtgtctg tgctagtccc                                               20

<210> SEQ ID NO 257
<211> LENGTH: 20
<212> TYPE: DNA
<213> ORGANISM: Artificial Sequence
<220> FEATURE:
<223> OTHER INFORMATION: Synthetic

<400> SEQUENCE: 257
gctgcttctg ctgtgaccta                                               20

<210> SEQ ID NO 258
<211> LENGTH: 20
<212> TYPE: DNA
<213> ORGANISM: Artificial Sequence
<220> FEATURE:
<223> OTHER INFORMATION: Synthetic

<400> SEQUENCE: 258
tatttgcgag ctccccgtac                                               20

<210> SEQ ID NO 259
<211> LENGTH: 20
```

<212> TYPE: DNA
<213> ORGANISM: Artificial Sequence
<220> FEATURE:
<223> OTHER INFORMATION: Synthetic

<400> SEQUENCE: 259
gcataagcac agcagcattc                                               20

<210> SEQ ID NO 260
<211> LENGTH: 20
<212> TYPE: DNA
<213> ORGANISM: Artificial Sequence
<220> FEATURE:
<223> OTHER INFORMATION: Synthetic

<400> SEQUENCE: 260
tccaaaaaga gaccagatgc                                               20

<210> SEQ ID NO 261
<211> LENGTH: 20
<212> TYPE: DNA
<213> ORGANISM: Artificial Sequence
<220> FEATURE:
<223> OTHER INFORMATION: Synthetic

<400> SEQUENCE: 261
aaatgcctgt ccactgtagc                                               20

<210> SEQ ID NO 262
<211> LENGTH: 20
<212> TYPE: DNA
<213> ORGANISM: Artificial Sequence
<220> FEATURE:
<223> OTHER INFORMATION: Synthetic

<400> SEQUENCE: 262
cttcagagga gcagcaccag                                               20

<210> SEQ ID NO 263
<211> LENGTH: 20
<212> TYPE: DNA
<213> ORGANISM: Artificial Sequence
<220> FEATURE:
<223> OTHER INFORMATION: Synthetic

<400> SEQUENCE: 263
gaatcttcag aggagcagca                                               20

<210> SEQ ID NO 264
<211> LENGTH: 20
<212> TYPE: DNA
<213> ORGANISM: Artificial Sequence
<220> FEATURE:
<223> OTHER INFORMATION: Synthetic

<400> SEQUENCE: 264
caaattggca tggcaggtct                                               20

<210> SEQ ID NO 265
<211> LENGTH: 20
<212> TYPE: DNA
<213> ORGANISM: Artificial Sequence
<220> FEATURE:
<223> OTHER INFORMATION: Synthetic

<400> SEQUENCE: 265

| gctttggttt tgagagtttg | 20 |

<210> SEQ ID NO 266
<211> LENGTH: 20
<212> TYPE: DNA
<213> ORGANISM: Artificial Sequence
<220> FEATURE:
<223> OTHER INFORMATION: Synthetic

<400> SEQUENCE: 266

| aggctttggt tttgagagtt | 20 |

<210> SEQ ID NO 267
<211> LENGTH: 20
<212> TYPE: DNA
<213> ORGANISM: Artificial Sequence
<220> FEATURE:
<223> OTHER INFORMATION: Synthetic

<400> SEQUENCE: 267

| gctcactcag gctttggttt | 20 |

<210> SEQ ID NO 268
<211> LENGTH: 20
<212> TYPE: DNA
<213> ORGANISM: Artificial Sequence
<220> FEATURE:
<223> OTHER INFORMATION: Synthetic

<400> SEQUENCE: 268

| ggtcctgcca aaatactact | 20 |

<210> SEQ ID NO 269
<211> LENGTH: 20
<212> TYPE: DNA
<213> ORGANISM: Artificial Sequence
<220> FEATURE:
<223> OTHER INFORMATION: Synthetic

<400> SEQUENCE: 269

| agcccttgtc cttgatctga | 20 |

<210> SEQ ID NO 270
<211> LENGTH: 20
<212> TYPE: DNA
<213> ORGANISM: Artificial Sequence
<220> FEATURE:
<223> OTHER INFORMATION: Synthetic

<400> SEQUENCE: 270

| tgtgggcttt ttgtgatgga | 20 |

<210> SEQ ID NO 271
<211> LENGTH: 20
<212> TYPE: DNA
<213> ORGANISM: Artificial Sequence
<220> FEATURE:
<223> OTHER INFORMATION: Synthetic

<400> SEQUENCE: 271

| aatcattcct gtgggctttt | 20 |

<210> SEQ ID NO 272
<211> LENGTH: 20
<212> TYPE: DNA
<213> ORGANISM: Artificial Sequence

```
<220> FEATURE:
<223> OTHER INFORMATION: Synthetic

<400> SEQUENCE: 272
ccgtgtatag atgagcaggt                                               20

<210> SEQ ID NO 273
<211> LENGTH: 20
<212> TYPE: DNA
<213> ORGANISM: Artificial Sequence
<220> FEATURE:
<223> OTHER INFORMATION: Synthetic

<400> SEQUENCE: 273
accgtgtata gatgagcagg                                               20

<210> SEQ ID NO 274
<211> LENGTH: 20
<212> TYPE: DNA
<213> ORGANISM: Artificial Sequence
<220> FEATURE:
<223> OTHER INFORMATION: Synthetic

<400> SEQUENCE: 274
tcatcttctt aggttctggg                                               20

<210> SEQ ID NO 275
<211> LENGTH: 20
<212> TYPE: DNA
<213> ORGANISM: Artificial Sequence
<220> FEATURE:
<223> OTHER INFORMATION: Synthetic

<400> SEQUENCE: 275
acaagctgat ggaaacgtcg                                               20

<210> SEQ ID NO 276
<211> LENGTH: 20
<212> TYPE: DNA
<213> ORGANISM: Artificial Sequence
<220> FEATURE:
<223> OTHER INFORMATION: Synthetic

<400> SEQUENCE: 276
tgctcgtaac atcagggaat                                               20

<210> SEQ ID NO 277
<211> LENGTH: 20
<212> TYPE: DNA
<213> ORGANISM: Artificial Sequence
<220> FEATURE:
<223> OTHER INFORMATION: Synthetic

<400> SEQUENCE: 277
aagatggtca tattgctcgt                                               20

<210> SEQ ID NO 278
<211> LENGTH: 20
<212> TYPE: DNA
<213> ORGANISM: Artificial Sequence
<220> FEATURE:
<223> OTHER INFORMATION: Synthetic

<400> SEQUENCE: 278
cgcgtcttgt cagtttccag                                               20
```

<210> SEQ ID NO 279
<211> LENGTH: 20
<212> TYPE: DNA
<213> ORGANISM: Artificial Sequence
<220> FEATURE:
<223> OTHER INFORMATION: Synthetic

<400> SEQUENCE: 279
cagctgtaat ccaaggaatg                                        20

<210> SEQ ID NO 280
<211> LENGTH: 20
<212> TYPE: DNA
<213> ORGANISM: Artificial Sequence
<220> FEATURE:
<223> OTHER INFORMATION: Synthetic

<400> SEQUENCE: 280
gggcttcatc agatctttca                                        20

<210> SEQ ID NO 281
<211> LENGTH: 20
<212> TYPE: DNA
<213> ORGANISM: Artificial Sequence
<220> FEATURE:
<223> OTHER INFORMATION: Synthetic

<400> SEQUENCE: 281
catgtatcac ttttgtcgca                                        20

<210> SEQ ID NO 282
<211> LENGTH: 20
<212> TYPE: DNA
<213> ORGANISM: Artificial Sequence
<220> FEATURE:
<223> OTHER INFORMATION: Synthetic

<400> SEQUENCE: 282 agcccccttta ttactcatgg                                       20

<210> SEQ ID NO 283
<211> LENGTH: 20
<212> TYPE: DNA
<213> ORGANISM: Artificial Sequence
<220> FEATURE:
<223> OTHER INFORMATION: Synthetic

<400> SEQUENCE: 283
ggagttacag ccaggctatt                                        20

<210> SEQ ID NO 284
<211> LENGTH: 20
<212> TYPE: DNA
<213> ORGANISM: Artificial Sequence
<220> FEATURE:
<223> OTHER INFORMATION: Synthetic

<400> SEQUENCE: 284
agtctcctct tggcatacgg                                        20

<210> SEQ ID NO 285
<211> LENGTH: 20
<212> TYPE: DNA
<213> ORGANISM: Artificial Sequence
<220> FEATURE:
<223> OTHER INFORMATION: Synthetic -continued

```
<400> SEQUENCE: 285
cccataagtg tgctctgaag                                                    20
```

ANTISENSE MODULATION OF B7 PROTEIN EXPRESSION

CROSS-REFERENCE TO RELATED APPLICATIONS

This is a continuation-in-part of U.S. application Ser. No. 09/326,186, filed Jun. 4, 1999, now U.S. Pat. No. 6,319,906, which is a continuation-in-part of U.S. application Ser. No. 08/777,266, filed Dec. 31, 1996, now U.S. Pat. No. 6,077,833.

FIELD OF THE INVENTION

This invention relates to diagnostics, research reagents and therapeutics for disease states which respond to modulation of T cell activation. In particular, this invention relates to antisense oligonucleotide interactions with certain messenger ribonucleic acids (mRNAs) or DNAs involved in the synthesis of proteins that modulate T cell activation. Antisense oligonucleotides designed to hybridize to nucleic acids encoding B7 proteins are provided. These oligonucleotides have been found to lead to the modulation of the activity of the RNA or DNA, and thus to the modulation of T cell activation. Palliative, therapeutic and prophylactic effects result.

BACKGROUND OF THE INVENTION

Inflammation is a localized protective response mounted by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage, synthesis and release of soluble inflammatory mediators, recruitment of inflammatory cells to the site of infection or tissue damage, destruction and removal of the invading organism or damaged tissue, and deactivation of the system once the invading organism or damage has been resolved. In many human diseases with an inflammatory component, the normal, homeostatic mechanisms which attenuate the inflammatory responses are defective, resulting in damage and destruction of normal tissue.

Cell—cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. In general, the first inflammatory cells to appear at the site of inflammation are neutrophils, followed by monocytes and lymphocytes. Cell—cell interactions are also critical for activation of both B-lymphocytes (B cells) and T-lymphocytes (T cells) with resulting enhanced humoral and cellular immune responses, respectively.

The hallmark of the immune system is its ability to distinguish between self (host) and nonself (foreign invaders). This remarkable specificity exhibited by the immune system is mediated primarily by T cells. T cells participate in the host's defense against infection but also mediate organ damage of transplanted tissues and contribute to cell attack in graft-versus-host disease (GVHD) and some autoimmune diseases. In order to induce an antigen-specific immune response, a T cell must receive signals delivered by an antigen-presenting cell (APC). T cell-APC interactions can be divided into three stages: cellular adhesion, T cell receptor (TCR) recognition, and costimulation. At least two discrete signals are required from an APC for induction of T cell activation. The first signal is antigen-specific and is provided when the TCR interacts with an antigen in the context of a major histocompatibility complex (MHC) protein, or an MHC-related CD1 protein, expressed on the surface of an APC ("CD," standing for "cluster of differentiation," is a term used to denote different T cell surface molecules). The second (costimulatory) signal involves the interaction of the T cell surface antigen, CD28, with its ligand on the APC, which is a member of the B7 family of proteins.

CD28, a disulfide-linked homodimer of a 44 kilodalton polypeptide and a member of the immunoglobulin superfamily, is one of the major costimulatory signal receptors on the surface of a resting T cell for T cell activation and cytokine production (Allison, Curr. Opin. Immunol., 1994, 6, 414; Linsley and Ledbetter, Annu. Rev. Immunol., 1993, 11, 191; June et al., Immunol. Today, 1994, 15, 321). Signal transduction through CD28 acts synergistically with TCR signal transduction to augment both interleukin-2 (IL-2) production and proliferation of naive T cells. B7-1 (also known as CD80) was the first ligand identified for CD28 (Liu and Linsley, Curr. Opin. Immunol., 1992, 4, 265). B7-1 is normally expressed at low levels on APCs, however, it is upregulated following activation by cytokines or ligation of cell surface molecules such as CD40 (Lenschow et al., Proc. Natl. Acad. Sci. U.S.A., 1993, 90, 11054; Nabavi et al., Nature, 1992, 360, 266). Initial studies suggested that B7-1 was the CD28 ligand that mediated costimulation (Reiser et al., Proc. Natl. Acad. Sci. U.S.A., 1992, 89, 271; Wu et al., J. Exp. Med., 1993, 178, 1789; Harlan et al., Proc. Natl. Acad. Sci. U.S.A., 1994, 91, 3137). However, the subsequent demonstration that anti-B7-1 monoclonal antibodies (mAbs) had minimal effects on primary mixed lymphocyte reactions and that B7-1-deficient mice responded normally to antigens (Lenschow et al., Proc. Natl. Acad. Sci. U.S.A., 1993, 90, 11054; Freeman et al., Science, 1993, 262, 909) resulted in the discovery of a second ligand for the CD28 receptor, B7-2 (also known as CD86). In contrast with anti-B7-1 mAbs, anti-B7-2 mAbs are potent inhibitors of T cell roliferation and cytokine production (Wu et al., J. Exp. Med., 1993, 178, 1789; Chen et al., J. Immunol., 1994, 152, 2105; Lenschow et al., Proc. Natl. Acad. Sci. U.S.A., 1993, 90, 11054). B7:CD28 signaling may be a necessary component of other T cell costimulatory pathways, such as CD40:CD40 L (CD40 ligand) signaling (Yang et al., Science, 1996, 273, 1862).

In addition to binding CD28, B7-1 and B7-2 bind the cytolytic T-lymphocyte associated protein CTLA4. CTLA4 is a protein that is structurally related to CD28 but is expressed on T cells only after activation (Linsley et al., J. Exp. Med., 1991, 174, 561). A soluble recombinant form of CTLA4, CTLA4-Ig, has been determined to be a more efficient inhibitor of the B7:CD28 interaction than monoclonal antibodies directed against CD28 or a B7 protein. In vivo treatment with CTLA4-Ig results in the inhibition of antibody formation to sheep red blood cells or soluble antigen (Linsley et al., Science, 1992, 257, 792), prolongation of cardiac allograft and pancreatic islet xenograft survival (Lin et al., J. Exp. Med., 1993, 178, 1801; Lenschow et al., 1992, Science, 257, 789; Lenschow et al., Curr. Opin. Immunol., 1991, 9, 243), and significant suppression of immune responses in GVHD (Hakim et al., J. Immun., 1995, 155, 1760). It has been proposed that CD28 and CTLA4, although both acting through common B7 receptors, serve opposing costimulatory and inhibitory functions, respectively (Allison et al., *Science*, 1995, 270, 932). CTLA4Ig, which binds both B7-1 and B7-2 molecules on antigen-presenting cells, has been shown to block T-cell costimulation in patients with stable psoriasis vulgaris, and to cause a 50% or greater sustained improvement in clinical disease activity in 46% of the patients to which it was administered. This result was dose-dependent. Abrams et al., *J. Clin. Invest.*, 1999, 9, 1243–1225.

European Patent Application No. EP 0 600 591, published Jun. 8, 1994 (A2), discloses a method of inhibiting tumor cell growth in which tumor cells from a patient are recombinantly engineered ex vivo to express a B7-1 protein and then reintroduced into a patient. As a result, an immunologic response is stimulated against both B7-transfected and non-transfected tumor cells. International Publication No. WO 95/03408, published Feb. 2, 1995, discloses nucleic acids encoding novel CTLA4/CD28 ligands which costimulate T cell activation, including B7-2 proteins. Also disclosed are antibodies to B7-2 proteins and methods of producing B7-2 proteins. International Publication No. WO 95/05464, published Feb. 23, 1995, discloses a polypeptide, other than B7-1, that binds to CTLA4, CD28 or CTLA4-Ig. Also disclosed are methods for obtaining a nucleic acid encoding such a polypeptide.

International Publication No. WO 95/06738, published Mar. 9, 1995, discloses nucleic acids encoding B7-2 (also known as B70) proteins. Also disclosed are antibodies to B7-2 proteins and methods of producing B7-2 proteins.

European Patent Application No. EP 0 643 077, published Mar. 15, 1995 (A1), discloses a monoclonal antibody which specifically binds a B7-2 (also known as B70) protein. Also disclosed are methods of producing monoclonal antibodies which specifically bind a B7-2 protein.

U.S. Pat. No. 5,434,131, issued Jul. 18, 1995, discloses the CTLA4 protein as a ligand for B7 proteins. Also disclosed are methods of producing CTLA4 fusion proteins (e.g., CTLA4-Ig) and methods of regulating immune responses using antibodies to B7 proteins or CTLA4 proteins.

International Publication No. WO 95/22619, published Aug. 24, 1995, discloses antibodies specific to B7-1 proteins which do not bind to B7-2 proteins. Also disclosed are methods of regulating immune responses using antibodies to B7-1 proteins.

International Publication No. WO 95/34320, published Dec. 21, 1995, discloses methods for inhibiting T cell responses using a first agent which inhibits a costimulatory agent, such as an CTLA4-Ig fusion protein, and a second agent which inhibits cellular adhesion, such as an anti-LFA-1 antibody. Such methods are indicated to be particularly useful for inhibiting the rejection of transplanted tissues or organs.

International Publication No. WO 95/32734, published Dec. 7, 1995, discloses FcγRII bridging agents which either prevent the upregulation of B7 molecules or impair the expression of ICAM-3 on antigen presenting cells. Such FcγRII bridging agents include proteins such as aggregated human IgG molecules or aggregated Fc fragments of human IgG molecules.

International Publication No. WO 96/11279, published Apr. 18, 1996 (A2) and May 17, 1996 (A3), discloses recombinant viruses comprising genetic sequences encoding (1) one or more immunostimulatory agents, including B7-1 and B7-2, and (2) and antigens from a disease causing agent. Also disclosed are methods of treating diseases using such recombinant viruses.

To date, there are no known therapeutic agents which effectively regulate and prevent the expression of B7 proteins such as B7-1 and B7-2. Thus, there is a long-felt need for compounds and methods which effectively modulate critical costimulatory molecules such as the B7 proteins. It is anticipated that oligonucleotides capable of modulating the expression of B7 proteins provide for a novel therapeutic class of anti-inflammatory agents with activity towards a variety of inflammatory or autoimmune diseases, or disorders or diseases with an inflammatory component such as asthma, juvenile diabetes mellitus, myasthenia gravis, Graves' disease, rheumatoid arthritis, allograft rejection, inflammatory bowel disease, multiple sclerosis, psoriasis, lupus erythematosus, systemic lupus erythematosus, diabetes, multiple sclerosis, contact dermatitis, rhinitis and various allergies. In addition, oligonucleotides capable of modulating the expression of B7 proteins would provide a novel means of manipulating the ex vivo proliferation of T cells.

SUMMARY OF THE INVENTION

In accordance with the present invention, oligonucleotides are provided which specifically hybridize with nucleic acids encoding B7-1 or B7-2. Certain oligonucleotides of the invention are designed to bind either directly to mRNA transcribed from, or to a selected DNA portion of, the B7-1 or B7-2 gene, thereby modulating the amount of protein translated from a B7-1 or B7-2 mRNA or the amount of mRNA transcribed from a B7-1 or B7-2 gene, respectively.

Oligonucleotides may comprise nucleotide sequences sufficient in identity and number to effect specific hybridization with a particular nucleic acid. Such oligonucleotides are commonly described as "antisense." Antisense oligonucleotides are commonly used as research reagents, diagnostic aids, and therapeutic agents.

It has been discovered that the B7-1 and B7-2 genes, encoding B7-1 and B7-2 proteins, respectively, are particularly amenable to this approach. As a consequence of the association between B7 expression and T cell activation and proliferation, inhibition of the expression of B7-1 or B7-2 leads to inhibition of the synthesis of B7-1 or B7-2, respectively, and thereby inhibition of T cell activation and proliferation. Additionally, the oligonucleotides of the invention may be used to inhibit the expression of one of several alternatively spliced mRNAs of a B7 transcript, resulting in the enhanced expression of other alternatively spliced B7 mRNAs. Such modulation is desirable for treating various inflammatory or autoimmune disorders or diseases, or disorders or diseases with an inflammatory component such as asthma, juvenile diabetes mellitus, myasthenia gravis, Graves' disease, rheumatoid arthritis, allograft rejection, inflammatory bowel disease, multiple sclerosis, psoriasis, lupus erythematosus, systemic lupus erythematosus, diabetes, multiple sclerosis, contact dermatitis, rhinitis, various allergies, and cancers and their metastases. Such modulation is further desirable for preventing or modulating the development of such diseases or disorders in an animal suspected of being, or known to be, prone to such diseases or disorders. The invention also relates to pharmaceutical compositions which comprise an antisense oligonucleotide to a B7 protein in combination with a second anti-inflammatory agent, such as a second antisense oligonucleotide to a protein which mediates intercellular interactions, e.g., an intercellular adhesion molecule (ICAM) protein.

Methods comprising contacting animals with oligonucleotides specifically hybridizable with nucleic acids encoding B7 proteins are herein provided. These methods are useful as tools, for example, in the detection and determination of the role of B7 protein expression in various cell functions and physiological processes and conditions, and for the diagnosis of conditions associated with such expression. Such methods can be used to detect the expression of B7 genes (i.e., B7-1 or B7-2) and are thus believed to be useful both therapeutically and diagnostically. Methods of modulating the expression of B7 proteins comprising contacting animals with oligonucleotides specifically hybridizable with a B7 gene are herein provided. These methods are believed to be useful both therapeutically and diagnostically as a consequence of the association between B7 expression and T cell activation and proliferation. The present invention also comprises methods of inhibiting B7-associated activation of T cells using the oligonucleotides of the invention. Methods of treating conditions in which abnormal or excessive T cell activation and proliferation occurs are also provided. These methods employ the oligonucleotides of the invention and are believed to be useful both therapeutically and as clinical research and diagnostic tools. The oligonucleotides of the present invention may also be used for research purposes. Thus, the specific hybridization exhibited by the oligonucleotides of the present invention may be used for assays, purifications, cellular product preparations and in other methodologies which may be appreciated by persons of ordinary skill in the art.

The methods disclosed herein are also useful, for example, as clinical research tools in the detection and determination of the role of B7-1 or B7-2 expression in various immune system functions and physiological processes and conditions, and for the diagnosis of conditions associated with their expression. The specific hybridization exhibited by the oligonucleotides of the present invention may be used for assays, purifications, cellular product preparations and in other methodologies which may be appreciated by persons of ordinary skill in the art. For example, because the oligonucleotides of this invention specifically hybridize to nucleic acids encoding B7 proteins, sandwich and other assays can easily be constructed to exploit this fact. Detection of specific hybridization of an oligonucleotide of the invention with a nucleic acid encoding a B7 protein present in a sample can routinely be accomplished. Such detection may include detectably labeling an oligonucleotide of the invention by enzyme conjugation, radiolabeling or any other suitable detection system. A number of assays may be formulated employing the present invention, which assays will commonly comprise contacting a tissue or cell sample with a detectably labeled oligonucleotide of the present invention under conditions selected to permit hybridization and measuring such hybridization by detection of the label, as is appreciated by those of ordinary skill in the art.

DETAILED DESCRIPTION OF THE INVENTION

Figure 1:
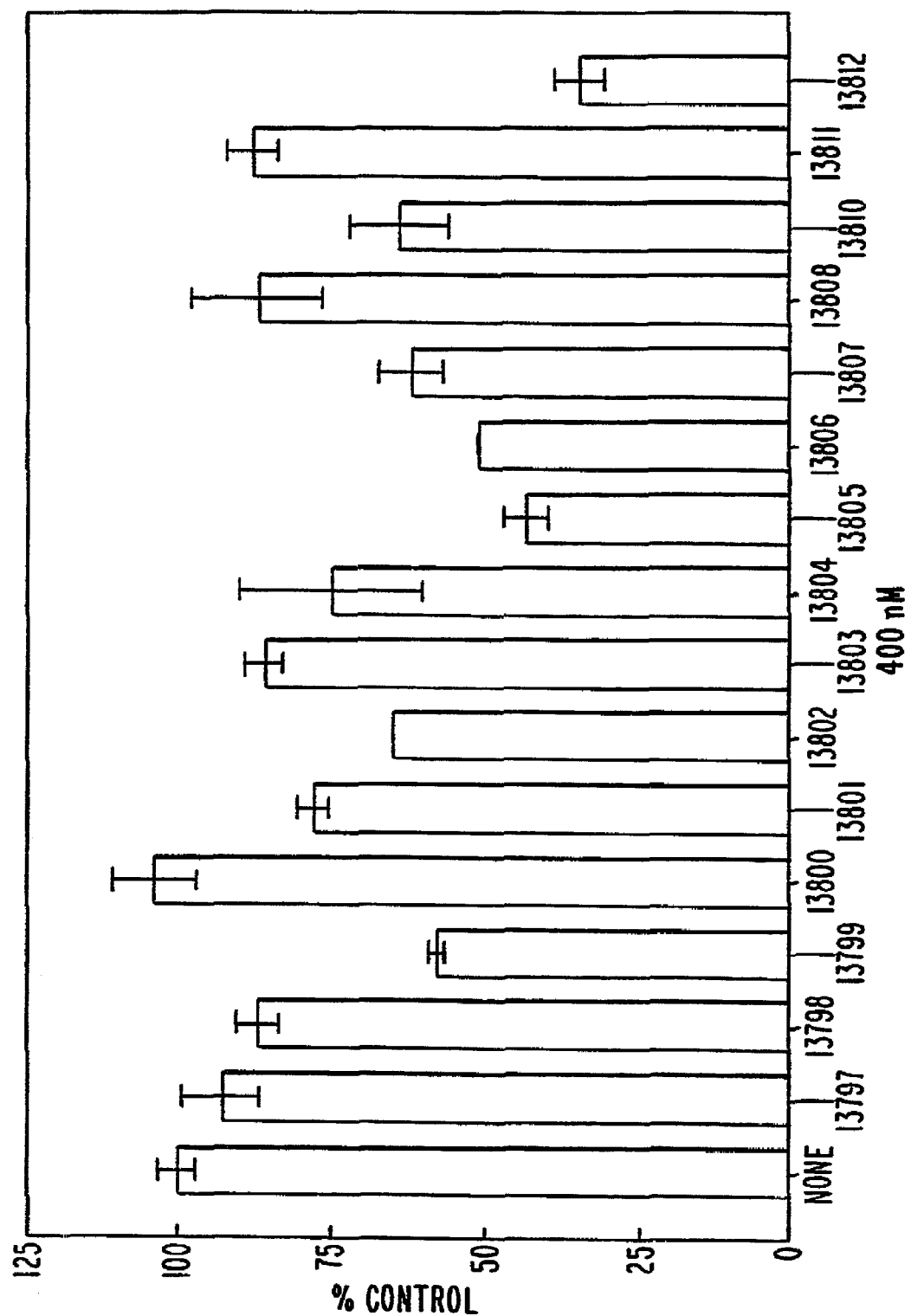
FIG. 1 is a bar graph showing the inhibitory effect of the indicated oligonucleotides on B7-1 protein expression in COS-7 cells.

The present invention employs oligonucleotides for use in antisense inhibition of the function of RNA and DNA encoding B7 proteins including B7-1 and B7-2. The present invention also employs oligonucleotides which are designed to be specifically hybridizable to DNA or messenger RNA (mRNA) encoding such proteins and ultimately to modulate the amount of such proteins transcribed from their respective genes. Such hybridization with mRNA interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with mRNA function is modulation of the expression of a B7 protein, wherein "modulation" means either an increase (stimulation) or a decrease (inhibition) in the expression of a B7 protein. In the context of the present invention, inhibition is the preferred form of modulation of gene expression.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses.

The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of HIV. U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenza virus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to CMV. U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent EBV infections.

It is preferred to target specific genes for antisense attack. "Targeting" an oligonucleotide to the associated nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a cellular gene associated with several immune system disorders and diseases (such as inflammation and autoimmune diseases), as well as with ostensibly "normal" immune reactions (such as a host animal's rejection of transplanted tissue), for which modulation is desired in certain instances. The targeting process also includes determination of a region (or regions) within this gene for the oligonucleotide interaction to occur such that the desired effect, either detection or modulation of expression of the protein, will result. Once the target region have been identified, oligonucleotides are chosen which are sufficiently complementary to the target, i.e., hybridize sufficiently well and with sufficient specificity to give the desired effect.

Generally, there are five regions of a gene that may be targeted for antisense modulation: the 5' untranslated region (hereinafter, the "5'-UTR"), the translation initiation codon region (hereinafter, the "tIR"), the open reading frame (hereinafter, the "ORF"), the translation termination codon region (hereinafter, the "tTR") and the 3' untranslated region (hereinafter, the "3'-UTR"). As is known in the art, these regions are arranged in a typical messenger RNA molecule in the following order (left to right, 5' to 3'): 5'-UTR, tIR, ORF, tTR, 3'-UTR. As is known in the art, although some eukaryotic transcripts are directly translated, many ORFs contain one or more sequences, known as "introns," which are excised from a transcript before it is translated; the expressed (unexcised) portions of the ORF are referred to as "exons" (Alberts et al., *Molecular Biology of the Cell*, 1983, Garland Publishing Inc., New York, pp. 411–415). Furthermore, because many eukaryotic ORFs are a thousand nucleotides or more in length, it is often convenient to subdivide the ORF into, e.g., the 5' ORF region, the central ORF region, and the 3' ORF region. In some instances, an ORF contains one or more sites that may be targeted due to some functional significance in vivo. Examples of the latter types of sites include intragenic stem-loop structures (see, e.g., U.S. Pat. No. 5,512,438) and, in unprocessed mRNA molecules, intron/exon splice sites. Within the context of the present invention, one preferred intragenic site is the region encompassing the translation initiation codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., *Growth Factors*, 1990, 4, 45; Gelbert et al., *Somat. Cell. Mol. Genet.*, 1990, 16, 173; Gold and Stormo, in: *Escherichia coli and Salmonella typhimurium: Cellular and Molecular Biology*, Vol. 2, 1987, Neidhardt et al., eds., American Society for Microbiology, Washington, D.C., p. 1303). Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions, in order to generate related polypeptides having different amino terminal sequences (Markussen et al., *Development*, 1.995, 121, 3723; Gao et al., *Cancer Res.*, 1995, 55, 743; McDermott et al., *Gene*, 1992, 117, 193; Perri et al., *J. Biol. Chem.*, 1991, 266, 12536; French et al., *J. Virol.*, 1989, 63, 3270; Pushpa-Rekha et al., *J. Biol. Chem.*, 1995, 270, 26993; Monaco et al., *J. Biol. Chem.*, 1994, 269, 347; DeVirgilio et al., *Yeast*, 1992, 8, 1043; Kanagasundaram et al., *Biochim. Biophys. Acta*, 1992, 1171, 198; Olsen et al., *Mol. Endocrinol.*, 1991, 5, 1246; Saul et al., *Appl. Environ. Microbiol.*, 1990, 56, 3117; Yaoita et al., *Proc. Natl. Acad. Sci. USA*, 1990, 87, 7090; Rogers et al., *EMBO J.*, 1990, 9, 2273). In the context of the invention, "start codon" and "translation initiation codon" refer to the codon or codons that are used in vivo to initiate translation of an mRNA molecule transcribed from a gene encoding a B7 protein, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation region" refer to a portion of such an mRNA or gene that encompasses from about 25 to about 50 contiguous nucleotides in either direction (i.e., 5' or 3') from a translation initiation codon. Similarly, the terms "stop codon region" and "translation termination region" refer to a portion of such an mRNA or gene that encompasses from about 25 to about 50 contiguous nucleotides in either direction (i.e., 5' or 3') from a translation termination codon.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates and those with $CH_2$—NH—O—$CH_2$, $CH_2$—N($CH_3$)—O—$CH_2$ [known as a methylene (methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$). Also preferred are oligonucleotides having morpholino backbone structures (Summerton and Weller, U.S. Pat. No. 5,034,506). Further preferred are oligonucleotides with NR—C(*)—$CH_2$—$CH_2$, $CH_2$—NR—C(*)—$CH_2$, $CH_2$—$CH_2$—NR—C(*), C(*)—NR—$CH_2$—$CH_2$ and $CH_2$—C(*)—NR—$CH_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., Science, 1991, 254, 1497; U.S. Pat. No. 5,539,082). Other preferred modified oligonucleotides may contain one or more substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy (2—O—$CH_2CH_2OCH_3$, also known as 2'-O-(2-methoxyethyl) or 2'-MOE) (Martin et al., Helv. Chim. Acta, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylamino-ethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow. (Martin et al., Helv. Chim. Acta, 1995, 78, 486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of the 5' terminal nucleotide. Oligonucleotides may also have sugar mimetics such as cyclobutyls in place of the pentofuranosyl group.

The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-methylcytosine, 5-hydroxymethylcytosine (HMC), glycosyl HMC and gentiobiosyl HMC, as well synthetic nucleobases, e.g., 5-bromouracil, 5-hydroxymethyluracil, 8-azaguanine, 7-deazaguanine, $N^6$(6-aminohexyl)adenine and 2,6-diaminopurine (Kornberg, A., DNA Replication, 1974, W.H. Freeman & Co., San Francisco, 1974, pp. 75–77; Gebeyehu, G., et al., Nucleic Acids Res., 1987, 15, 4513).

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 31 position of the sugar of the 3' terminal nucleotide, the 5' position of the sugar of the 5' terminal nucleotide, and the 2' position of the sugar of any nucleotide. The $N^6$ position of a purine nucleobase may also be utilized to link a lipophilic moiety to an oligonucleotide of the invention (Gebeyehu, G., et al., Nucleic Acids Res., 1987, 15, 4513). Such lipophilic moieties include but are not limited to a cholesteryl moiety (Letsinger et al., Proc. Natl. Acad. Sci. USA, 1989, 86, 6553), cholic acid (Manoharan et al., Bioorg. Med. Chem. Let., 1994, 4, 1053), a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylamino-carbonyl-oxycholesterol moiety (Crooke et al., J. Pharmacol. Exp. Ther., 1996, 277, 923). Oligonucleotides comprising lipophilic moieties, and methods for preparing such oligonucleotides, as disclosed in U.S. Pat. Nos. 5,138,045, 5,218,105 and 5,459,255, the contents of which are hereby incorporated by reference.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for the target RNA molecule but are unable to support nuclease activity (e.g., 2'-fluoro- or 2'-methoxyethoxy substituted). Other chimeras include "wingmers," that is, oligonucleotides in which the 5' portion of the oligonucleotide serves as a substrate for, e.g., RNase H, whereas the 3' portion is modified in such a fashion so as to have greater affinity for the target RNA molecule but is unable to support nuclease activity (e.g., 2'-fluoro- or 2'-methoxyethoxy substituted), or vice-versa.

The oligonucleotides in accordance with this invention preferably comprise from about 8 to about 30 nucleotides. It is more preferred that such oligonucleotides comprise from about 15 to 25 nucleotides. As is known in the art, a nucleotide is a base-sugar combination suitably bound to an adjacent nucleotide through a phosphodiester, phosphorothioate or other covalent linkage.

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

The oligonucleotides of the present invention can be utilized as therapeutic compounds, diagnostic tools and as research reagents and kits. The term "therapeutic uses" is intended to encompass prophylactic, palliative and curative uses wherein the oligonucleotides of the invention are contacted with animal cells either in vivo or ex vivo. When contacted with animal cells ex vivo, a therapeutic use includes incorporating such cells into an animal after treatment with one or more oligonucleotides of the invention. While not intending to be bound to a particular utility, the ex vivo modulation of, e.g., T cell proliferation by the oligonucleotides of the invention can be employed in, for example, potential therapeutic modalities wherein it is desired to modulate the expression of a B7 protein in APCs. As an example, oligonucleotides that inhibit the expression of B7-1 proteins are expected to enhance the availability of B7-2 proteins on the surface of APCS, thus increasing the costimulatory effect of B7-2 on T cells ex vivo (Levine et al., *Science*, 1996, 272, 1939).

For therapeutic uses, an animal suspected of having a disease or disorder which can be treated or prevented by modulating the expression or activity of a B7 protein is, for example, treated by administering oligonucleotides in accordance with this invention. The oligonucleotides of the invention can be utilized in pharmaceutical compositions by adding an effective amount of an oligonucleotide to a suitable pharmaceutically acceptable diluent or carrier. Workers in the field have identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans.

The oligonucleotides of the present invention can be further used to detect the presence of B7-specific nucleic acids in a cell or tissue sample. For example, radiolabeled oligonucleotides can be prepared by $^{32}$P labeling at the 5' end with polynucleotide kinase (Sambrook et al., *Molecular Cloning. A Laboratory Manual*, Cold Spring Harbor Laboratory Press, 1989, Volume 2, pg. 10.59). Radiolabeled oligonucleotides are then contacted with cell or tissue samples suspected of containing B7 message RNAs (and thus B7 proteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of B7 proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a B7 gene. Quantitation of the silver grains permits detection of the expression of mRNA molecules encoding these proteins and permits targeting of oligonucleotides to these areas.

Analogous assays for fluorescent detection of expression of B7 nucleic acids can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling Va.

The present invention employs oligonucleotides targeted to nucleic acids encoding B7 proteins and oligonucleotides targeted to nucleic acids encoding such proteins. Kits for detecting the presence or absence of expression of a B7 protein may also be prepared. Such kits include an oligonucleotide targeted to an appropriate gene, i.e., a gene encoding a B7 protein. Appropriate kit and assay formats, such as, e.g., "sandwich" assays, are known in the art and can easily be adapted for use with the oligonucleotides of the invention. Hybridization of the oligonucleotides of the invention with a nucleic acid encoding a B7 protein can be detected by means known in the art. Such means may include conjugation of an enzyme to the oligonucleotide, radiolabelling of the oligonucleotide or any other suitable detection systems. Kits for detecting the presence or absence of a B7 protein may also be prepared.

In the context of this invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

The formulation of therapeutic compositions and their subsequent administration is believed to be within the skill of those in the art. In general, for therapeutics, a patient in need of such therapy is administered an oligonucleotide in accordance with the invention, commonly in a pharmaceutically acceptable carrier, in doses ranging from 0.01 μg to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated.

In some cases, it may be more effective to treat a patient with an oligonucleotide of the invention in conjunction with other therapeutic modalities in order to increase the efficacy of a treatment regimen. In the context of the invention, the term "treatment regimen" is meant to encompass therapeutic, palliative and prophylactic modalities. In a preferred embodiment, the oligonucleotides of the invention are used in conjunction with an anti-inflammatory and/or immunosuppressive agent, preferably one or more antisense oligonucleotides targeted to an intercellular adhesion molecule (ICAM), preferably to ICAM-1. Other anti-inflammatory and/or immunosuppressive agents that may be used in combination with the oligonucleotides of the invention include, but are not limited to, soluble ICAM proteins (e.g., sICAM-1), antibody-toxin conjugates, prednisone, methylprednisolone, azathioprine, cyclophosphamide, cyclosporine, interferons, sympathomimetics, conventional antihistamines (histamine $H_1$ receptor antagonists, including, for example, brompheniramine maleate, chlorpheniramine maleate, dexchlorpheniramine maleate, tripolidine HCl, carbinoxamine maleate, clemastine fumarate, dimenhydrinate, diphenhydramine HCl, diphenylpyraline HCl, doxylamine succinate, tripelennamine citrate, tripelennamine HCl, cyclizine HCl, hydroxyzine HCl, meclizine HCl, methdilazine HCl, promethazine HCl, trimeprazine tartrate, azatadine maleate, cyproheptadine HCl, terfenadine, etc.), histamine $H_2$ receptor antagonists (e.g., ranitidine). See, generally, *The Merck Manual of Diagnosis and Therapy*, 15th Ed., Berkow et al., eds., 1987, Rahway, N.J., pages 302–336 and 2516–2522). When used with the compounds of the invention, such agents may be used individually, sequentially, or in combination with one or more other such agents.

In another preferred embodiment of the invention, an antisense oligonucleotide targeted to one B7 mRNA species (e.g., B7-1) is used in combination with an antisense oligonucleotide targeted to a second B7 mRNA species (e.g., B7-2) in order to inhibit the costimulatory effect of B7 molecules to a more extensive degree than can be achieved with either oligonucleotide used individually. In a related version of this embodiment, two or more oligonucleotides of the invention, each targeted to an alternatively spliced B7-1 or B7-2 mRNA, are combined with each other in order to inhibit expression of both forms of the alternatively spliced mRNAs. It is known in the art that, depending on the specificity of the modulating agent employed, inhibition of one form of an alternatively spliced mRNA may not result in a sufficient reduction of expression for a given condition to be manifest. Thus, such combinations may, in some instances, be desired to inhibit the expression of a particular B7 gene to an extent necessary to practice one of the methods of the invention.

Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years. In the case of in individual known or suspected of being prone to an autoimmune or inflammatory condition, prophylactic effects may be achieved by administration of preventative doses, ranging from 0.01 μg to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models. In general, dosage is from 0.01 µg to 100 g per kg of body weight, and may be given once or more daily, weekly, monthly or yearly, or even once every 2 to 20 years.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

The following examples are provided for illustrative purposes only and are not intended to limit the invention.

EXAMPLES

Example 1

Synthesis of Nucleic Acids Oligonucleotides

Oligonucleotides were synthesized on an automated DNA synthesizer using standard phosphoramidite chemistry with oxidation using iodine. β-Cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages. The thiation cycle wait step was increased to 68 seconds and was followed by the capping step.

The 2'-fluoro phosphorothioate oligonucleotides of the invention were synthesized using 5'-dimethoxytrityl-3'-phosphoramidites and prepared as disclosed in U.S. patent application Ser. No. 463,358, filed Jan. 11, 1990, now abandoned, and Ser. No. 566,977, filed Aug. 13, 1990, now abandoned, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

The 2'-methoxy (2'-O-methyl) oligonucleotides of the invention were synthesized using 2'-methoxy β-cyanoethyl-diisopropyl-phosphoramidites (Chemgenes, Needham Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va. The 3'-base used to start the synthesis was a 2'-deoxyribonucleotide. The 2'-O-propyl oligonucleotides of the invention are prepared by a slight modification of this procedure.

The 2' methoxyethoxy (2'-O—CH$_2$CH$_2$OCH$_3$) oligonucleotides of the invention were synthesized according to the method of Martin, Helv. Chim. Acta 1995, 78, 486. For ease of synthesis, the last nucleotide was a deoxynucleotide. All 2'-O—CH$_2$CH$_2$OCH$_3$- cytosines were 5-methyl cytosines, which were synthesized according to the following procedures.

Synthesis of 5-Methyl cytosine monomers:

2,2'-Anhydro [1-(β-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/Hexane/Acetone (5:5:1) containing 0.5% Et$_3$NH. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tic, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added to the later solution dropwise, over a 45 minute period. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (tic showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxytetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) nucleoside amidites

2'-(Dimethylaminooxyethoxy) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O2-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided.

5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy) ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate: hexane, 60:40). The solvent was evaporated in vacuum. Residue obtained was placed on a flash column and eluted with ethyl acetate:hexane (60:40), to get 2'-O-([2-phthalimidoxy) ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O-[N,N-dimethylaminooxyethyl]-5-methyluridine

5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous Na2SO4 and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P2O5 under high vacuum overnight at 40° C. Then the reaction mixture was dissolved in anhydrous acetonitrile (8.4 mL) and 2-cyanoethyl-N,N,N1,N1-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO3 (40 mL). Ethyl acetate layer was dried over anhydrous Na2SO4 and concentrated. Residue obtained was chromatographed (ethyl acetate as eluent) to get 5'-O-DMT-2'-O-(2-N,N-dimethylaminooxyethyl)-5-methyluridine -3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3-O-isomer. 2'-O-(2-ethylacetyl) diaminopurine riboside may be resolved and converted to 2'-0-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2'-N-isobutyryl-6-O-diphenylcarbamoyl-2'-O-(2-ethylacetyl)-5-O-(4,4-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5-O-(4,4'-dimethoxytrityl) guanosine-3'-[(2-cyanoethyl)-N,N-diisopropylphosphoramidite].

2-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2 (2-N,N-dimethylaminoethoxy) ethyl]-5-methyl uridine

2[2-(Dimethylamino)ethoxy] ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O2-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2 (2-N,N-dimethyl aminoethoxy)ethyl)]-5-methyl uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated NaHCO3 solution, followed by saturated NaCl solution and dried over anhydrous sodium sulfate. Evaporation of the solvent followed by silica gel chromatography using MeOH:CH2Cl2:Et3N (20:1, v/v, with 1% triethylamine) gives the title compound.

5'-O-Dimethoxytrityl-2'-O-[2(2-N,N-dimethylaminoethoxy) ethyl)]-5-methyl uridine-3-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in CH2Cl2 (20 mL) under an atmosphere of argon. The reaction mixture is stirred overnight and the solvent evaporated. The resulting residue is purified by silica gel flash column chromatography with ethyl acetate as the eluent to give the title compound.

Purification:

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0.

Oligodeoxynucleotides and their phosphorothioate analogs were judged from electrophoresis to be greater than 80% full length material.

B7 Antisense Oligonucleotides

A series of oligonucleotides with sequences designed to hybridize to the published human B7-1 (hB7-1) and murine (mB7-1) mRNA sequences (Freeman et al., *J. Immunol.*, 1989, 143, 2714, and Freeman et al., *J. Exp. Med.*, 1991, 174, 625 respectively). The sequences of and modifications to these oligonucleotides, and the location of each of their target sites on the hB7-1 mRNA, are given in Tables 1 and 2. Similarly, a series of oligonucleotides with sequences designed to hybridize to the human B7-2 (hB7-2) and murine B7-2 (mB7-2) mRNA published sequences (respectively, Azuma et al., *Nature*, 1993, 366, 76; Chen et al., *J. Immunol.*, 1994, 152, 4929) were synthesized. The sequences of and modifications to these oligonucleotides and the location of each of their target sites on the hB7-2 mRNA are described in Tables 3 and 4. Antisense oligonucleotides targeted to ICAM-1, including ISIS 2302 (SEQ ID NO: 17), have been described in U.S. Pat. No. 5,514,788, which issued May 7, 1996, hereby incorporated by reference. ISIS 1082 (SEQ ID NO: 102) and ISIS 3082 (SEQ ID NO: 101) have been previously described (Stepkowski et al., *J. Immunol.*, 1994, 153, 5336).

Subsequent to their initial cloning, alternative splicing events of B7 transcripts have been reported. The reported alternative splicing for B7-1 is relatively simple, in that it results in messages extended 5' relative to the 5' terminus of the human and murine B7-1 cDNA sequences originally reported (Borriello et al., *J. Immunol.*, 1994, 153, 5038; Inobe et al., *J. Immunol.*, 1996, 157, 588). In order to retain the numbering of the B7-1 sequences found in the references initially reporting B7-1 sequences, positions within these 5' extensions of the initially reported sequences have been given negative numbers (beginning with position −1, the most 3' base of the 5' extension) in Tables 1 and 2. The processing of murine B7-2 transcripts is considerably more complex than that so far reported for B7-1; for example, at least five distinct murine B7-2 mRNAs, and at least two distinct human B7-2 mRNAs, can be produced by alternative splicing events (Borriello et al., *J. Immunol.*, 1995, 155, 5490; Freeman et al., WO 95/03408, published Feb. 2, 1995; see also Jellis et al., *Immunogenet.*, 1995, 42, 85). The nature of these splicing events is such that different 5' exons are used to produce distinct B7-2 mRNAs, each of which has a unique 5' sequence but which share a 3' portion consisting of some or all of the B7-2 sequence initially reported. As a result, positions within the 5' extensions of B7-2 messages cannot be uniquely related to a position within the sequence initially reported. Accordingly, in Table 3, a different set of coordinates (corresponding to those of SEQ ID NO: 1 of WO 95/03408) and, in Table 4, the exon number (as given in Borriello et al., *J. Immunol.*, 1995, 155, 5490) is used to specify the location of targeted sequences which are not included in the initially reported B7-2 sequence. Furthermore, although these 5' extended messages contain potential in-frame start codons upstream from the ones indicated in the initially published sequences, for simplicity's sake, such additional potential start codons are not indicated in the description of target sites in Tables 1–4.

In Tables 1–4, the following abbreviations are used: UTR, untranslated region; ORF, open reading frame; tIR, translation initiation region; tTR, translation termination region; FITC, fluorescein isothiocyanate. Chemical modifications are indicated as follows. Residues having 2' fluoro (2'F), 2'-methoxy (2'MO) or 2'-methoxyethoxy (2'ME) modification are emboldened, with the type of modification being indicated by the respective abbreviations. Unless otherwise indicated, interresidue linkages are phosphodiester linkages; phosphorothioate linkages are indicated by an "S" in the superscript position (e.g., $T^SA$). Target positions are numbered according to Freeman et al., *J. Immunol.*, 1989, 143:2714 (human B7-1 cDNA sequence; Table 1), Freeman et al., *J. Exp. Med.*, 1991, 174, 625 (murine B7-1 cDNA sequence; Table 2), Azuma et al., *Nature*, 1993, 366:76 (human B7-2 cDNA sequence; Table 3) and Chen et al., *J. Immunol.*, 1994, 152:4929 (murine B7-2 cDNA sequence; Table 4). Nucleotide base codes are as given in 37 C.F.R. § 1.822(b)(1).

TABLE 1

Sequences of Oligonucleotides Targeted to Human B7-1 mRNA

| ISIS # | Target Position; Site (and/or Description) | Oligonucleotide Sequence (5' –> 3') and Chemical Modifications | SEQ ID NO: |
|---|---|---|---|
| 13797 | 0053–0072; 5' UTR | $G^SG^SG^ST^SA^SA^SG^SA^SC^ST^SC^SC^SA^SC^ST^ST^SC^ST^SG^SA$ | 22 |
| 13798 | 0132–0151; 5' UTR | $G^SG^SG^ST^SC^ST^SC^SC^SA^SA^SA^SG^SG^ST^ST^SG^ST^SG^SG^SA$ | 23 |
| 13799 | 0138–0157; 5' UTR | $G^ST^ST^SC^SC^ST^SG^SG^SG^ST^SC^ST^SC^SC^SA^SA^SA^SG^SG^ST$ | 24 |
| 13800 | 0158–0177; 5' UTR | $A^SC^SA^SC^SA^SC^SA^SG^SA^SG^SA^ST^ST^SG^SG^SA^SG^SG^ST$ | 25 |
| 13801 | 0193–0212; 5' UTR | $G^SC^ST^SC^SA^SC^SG^ST^SA^SG^SA^SA^SG^SA^SC^SC^SC^ST^SC^SC$ | 26 |
| 13802 | 0217–0236; 5' UTR | $G^SG^SC^SA^SG^SG^SG^SC^ST^SG^SA^ST^SG^SA^SC^SA^SA^ST^SC^SC$ | 27 |
| 13803 | 0226–0245; 5' UTR | $T^SG^SC^SA^SA^SA^SC^SA^SG^SG^SC^SA^SG^SG^SG^SC^ST^SG^SA$ | 28 |
| 13804 | 0246–0265; 5' UTR | $A^SG^SA^SC^SC^SA^SG^SG^SG^SC^SA^SC^ST^ST^SC^SC^SC^SA^SG^SG$ | 29 |
| 13805 | 0320–0339; tIR | $C^SC^ST^SG^SC^SC^ST^SC^SC^SG^ST^SG^ST^SG^ST^SG^SG^SC^SC$ | 30 |
| 13806 | 0380–0399; 5' ORF | $G^SA^SC^SC^SA^SG^SC^SC^SA^SG^SC^SA^SC^SC^SA^SA^SG^SA^SG^SC$ | 31 |
| 13807 | 0450–0469; 5' ORF | $C^SC^SA^SC^SA^SG^SG^SA^SA^SC^SA^SG^SC^SG^ST^ST^SG^SC^SC^SA^SC$ | 32 |
| 13808 | 0568–0587; 5' ORF | $C^SC^SG^SG^ST^ST^SC^ST^ST^SG^ST^SA^SC^ST^SC^SG^SG^SG^SC^SC$ | 33 |
| 13809 | 0634–0653; central ORF | $G^SC^SC^SC^ST^SC^SG^ST^SC^SA^SG^SA^ST^SG^SG^SG^SC^SG^SC^SA$ | 51 |
| 13810 | 0829–0848; central ORF | $C^SC^SA^SA^SC^SC^SA^SG^SG^SA^SG^SA^SG^SG^ST^SG^SA^SG^SG^SC$ | 34 |
| 13811 | 1102–1121; 3' ORF | $G^SG^SC^SA^SA^SA^SG^SC^SA^SG^ST^SA^SG^SG^ST^SC^SA^SG^SG^SC$ | 35 |
| 13812 | 1254–1273; 3'-UTR | $G^SC^SC^ST^SC^SA^ST^SG^SA^ST^SC^SC^SC^SA^SC^SG^SA^ST^SC$ | 36 |
| 13872 | (scrambled # 13812) | $A^SG^ST^SC^SC^ST^SA^SC^ST^SA^SC^SC^SA^SG^SC^SC^SG^SC^SC^ST$ | 52 |
| 12361 | 0056–0075; 5' UTR | $T^SC^SA^SG^SG^SG^ST^SA^SA^SG^SA^SC^ST^SC^SC^SA^SC^ST^ST^SC$ | 38 |
| 12348 | 0056–0075; 5' UTR | TCAGGG$^ST^SA^SA^SG^SA^SC^ST^SC$CACTTC (2'ME) | 38 |
| 12473 | 0056–0075; 5' UTR | $T^SC^SA^SG^SG^SG^ST^SA^SA^SG^SA^SC^ST^SC^SC^SC^SA^SC^ST^ST^SC$ (2'Fl) | 38 |

TABLE 1-continued

Sequences of Oligonucleotides Targeted to Human B7-1 mRNA

| ISIS # | Target Position; Site (and/or Description) | Oligonucleotide Sequence (5' -> 3') and Chemical Modifications | SEQ ID NO: |
|---|---|---|---|
| 12362 | 0143–0162; 5' UTR | $A^SG^SG^SG^ST^SG^ST^ST^SC^SC^ST^SG^SG^SG^ST^SC^ST^SC^SC^SA$ | 39 |
| 12349 | 0143–0162; 5' UTR | AGGGTG$^S$T$^S$T$^S$C$^S$C$^S$T$^S$G$^S$G$^S$G$^S$TCTCCA (2'ME) | 39 |
| 12474 | 0143–0162; 5' UTR | A$^S$G$^S$G$^S$G$^S$T$^S$G$^S$T$^S$T$^S$C$^S$C$^S$T$^S$G$^S$G$^S$G$^S$T$^S$C$^S$T$^S$C$^S$C$^S$A (2'Fl) | 39 |
| 12363 | 0315–0334; tIR | $C^ST^SC^SC^SG^ST^SG^ST^SG^ST^SG^SG^SC^SC^SC^SA^ST^SG^SG^SC$ | 40 |
| 12350 | 0315–0334; tIR | CTCCGT$^S$G$^S$T$^S$G$^S$T$^S$G$^S$G$^S$CCATGGC (2'ME) | 40 |
| 12475 | 0315–0334; tIR | C$^S$T$^S$C$^S$C$^S$G$^S$T$^S$G$^S$T$^S$G$^S$T$^S$G$^S$G$^S$C$^S$C$^S$C$^S$A$^S$T$^S$G$^S$G$^S$C (2'Fl) | 40 |
| 12364 | 0334–0353; 5' ORF | $G^SG^SA^ST^SG^SG^ST^SG^SA^ST^SG^ST^ST^SC^SC^SC^ST^SG^SC^SC$ | 41 |
| 12351 | 0334–0353; 5' ORF | GGATGG$^S$T$^S$G$^S$A$^S$T$^S$G$^S$T$^S$T$^S$CCCTGCC (2'ME) | 41 |
| 12476 | 0334–0353; 5' ORF | G$^S$G$^S$A$^S$T$^S$G$^S$G$^S$T$^S$G$^S$A$^S$T$^S$G$^S$T$^S$T$^S$C$^S$C$^S$C$^S$T$^S$G$^S$C$^S$C (2'Fl) | 41 |
| 12365 | 0387–0406; 5' ORF | $T^SG^SA^SG^SA^SA^SA^SG^SA^SC^SC^SA^SG^SC^SA^SC$ | 42 |
| 12352 | 0387–0406; 5' ORF | TGAGAA$^S$A$^S$G$^S$A$^S$C$^S$C$^S$A$^S$G$^S$C$^S$CAGCAC (2'ME) | 42 |
| 12477 | 0387–0406; 5' ORF | T$^S$G$^S$A$^S$G$^S$A$^S$A$^S$A$^S$G$^S$A$^S$C$^S$C$^S$A$^S$G$^S$C$^S$C$^S$A$^S$G$^S$C$^S$A$^S$C (2'Fl) | 42 |
| 12366 | 0621–0640; central ORF | $G^SG^SG^SC^SG^SC^SA^SG^SA^SG^SC^SC^SA^SG^SG^SA^ST^SC^SA^SC$ | 43 |
| 12353 | 0621–0640; central ORF | GGGCGC$^S$A$^S$G$^S$A$^S$G$^S$C$^S$C$^S$A$^S$GGATCAC (2'ME) | 43 |
| 12478 | 0621–0640; central ORF | G$^S$G$^S$G$^S$C$^S$G$^S$C$^S$A$^S$G$^S$A$^S$G$^S$C$^S$C$^S$A$^S$G$^S$G$^S$A$^S$T$^S$C$^S$A$^S$C (2'Fl) | 43 |
| 12367 | 1042–1061; 3' ORF | $G^SG^SC^SC^SC^SA^SG^SG^SA^ST^SG^SG^SG^SA^SG^SC^SA^SG^SG^ST$ | 44 |
| 12354 | 1042–1061; 3' ORF | GGCCCA$^S$G$^S$G$^S$A$^S$T$^S$G$^S$G$^S$G$^S$AGCAGGT (2'ME) | 44 |
| 12479 | 1042–1061; 3' ORF | G$^S$G$^S$C$^S$C$^S$C$^S$A$^S$G$^S$G$^S$A$^S$T$^S$G$^S$G$^S$G$^S$A$^S$G$^S$C$^S$A$^S$G$^S$G$^S$T (2'Fl) | 44 |
| 12368 | 1069–1088; tTR | $A^SG^SG^SG^SC^SG^ST^SA^SC^SA^SC^ST^ST^ST^SC^SC^SC^ST^ST^SC$ | 45 |
| 12355 | 1069–1088; tTR | AGGGCG$^S$T$^S$A$^S$C$^S$A$^S$C$^S$T$^S$T$^S$TCCCTTC (2'ME) | 45 |
| 12480 | 1069–1088; tTR | A$^S$G$^S$G$^S$G$^S$C$^S$G$^S$T$^S$A$^S$C$^S$A$^S$C$^S$T$^S$T$^S$T$^S$C$^S$C$^S$C$^S$T$^S$T$^S$C (2'Fl) | 45 |
| 12369 | 1100–1209; tTR | $C^SA^SG^SC^SC^SC^SC^ST^ST^SG^SC^ST^ST^SC^ST^SG^SC^SG^SG^SA$ | 46 |
| 12356 | 1100–1209; tTR | CAGCCC$^S$C$^S$T$^S$T$^S$G$^S$C$^S$T$^S$T$^S$C$^S$TGCGGA (2'ME) | 46 |
| 12481 | 1100–1209; tTR | C$^S$A$^S$G$^S$C$^S$C$^S$C$^S$C$^S$T$^S$T$^S$G$^S$C$^S$T$^S$T$^S$C$^S$T$^S$G$^S$C$^S$G$^S$G$^S$A (2'Fl) | 46 |
| 12370 | 1360–1380; 3' UTR | $A^SA^SG^SG^SA^SG^SA^SG^SG^SG^SA^ST^SG^SC^SC^SA^SG^SC^SC^SA$ | 47 |
| 12357 | 1360–1380; 3' UTR | AAGGAG$^S$A$^S$G$^S$G$^S$G$^S$A$^S$T$^S$G$^S$CCAGCCA (2'ME) | 47 |
| 12482 | 1360–1380; 3' UTR | A$^S$A$^S$G$^S$G$^S$A$^S$G$^S$A$^S$G$^S$G$^S$G$^S$A$^S$T$^S$G$^S$C$^S$C$^S$A$^S$G$^S$C$^S$C$^S$A (2'Fl) | 47 |
| 12914 | (−0038 to −0059; 5' UTR of alternative mRNA) | C$^S$T$^S$G$^S$T$^S$T$^S$A$^S$C$^S$T$^S$T$^S$T$^S$A$^S$C$^S$A$^S$G$^S$A$^S$G$^S$G$^S$G$^S$T$^S$T$^S$G (2'MO) | 48 |
| 12915 | (−0035 to −0059; 5' UTR of alternative mRNA) | C$^S$T$^S$T$^S$C$^S$T$^S$G$^S$T$^S$T$^S$A$^S$C$^S$T$^S$T$^S$T$^S$A$^S$C$^S$A$^S$G$^S$A$^S$G$^S$G$^S$G$^S$T$^S$T$^S$T$^S$G (2'MO) | 49 |
| 13498 | (−0038 to −0058; 5' UTR of alternative mRNA) | C$^S$T$^S$G$^S$T$^S$T$^S$A$^S$C$^S$T$^S$T$^S$T$^S$A$^S$C$^S$A$^S$G$^S$A$^S$G$^S$G$^S$G$^S$T$^S$T$^S$T (2'ME) | 50 |
| 13499 | (−0038 to −0058; 5' UTR of alternative mRNA) | CTGTTACTTTACAGAGGGTTT (2'ME) | 50 |

TABLE 2

Sequences of Oligonucleotides Targeted to Murine B7-1 mRNA

| ISIS # | Target Position; Site | Oligonucleotide Sequence (5' -> 3') and Chemical Modifications | SEQ ID NO: |
|---|---|---|---|
| 14419 | 0009–0028; 5' UTR | $A^SG^ST^SA^SG^SA^SG^ST^SC^ST^SA^ST^ST^SG^SA^SG^SG^ST^SA$ | 53 |
| 14420 | 0041–0060; 5' UTR | $G^SG^ST^ST^SG^SA^SG^ST^ST^ST^SC^SA^SC^SA^SC^SC^ST^SG^SA$ | 54 |
| 14421 | 0071–0091; 5' UTR | $G^ST^SC^SC^SA^SC^SA^SG^SA^SA^ST^SG^SG^SA^SA^SC^SA^SG^SA^SG$ | 55 |
| 14422 | 0109–0128; 5' UTR | $G^SG^SC^SA^ST^SC^SC^SA^SC^SC^SC^SG^SG^SC^SA^SG^SA^ST^SG^SC$ | 56 |
| 14423 | 0114–0133; 5' UTR | $T^SG^SG^SA^ST^SG^SG^SC^SA^ST^SC^SC^SA^SC^SC^SC^SG^SG^SC^SA$ | 57 |
| 14424 | 0168–0187; 5' UTR | $A^SG^SG^SC^SA^SC^SC^ST^SC^SC^ST^SA^SG^SG^SC^ST^SC^SA^SC^SA$ | 58 |
| 14425 | 0181–0200; 5' UTR | $G^SC^SC^SA^SA^ST^SG^SG^SA^SG^SC^ST^ST^SA^SG^SG^SC^SA^SC^SC$ | 59 |
| 14426 | 0208–0217; 5' UTR | $C^SA^ST^SG^SA^ST^SG^SG^SG^SA^SA^SA^SG^SC^SA^SG^SG^SA$ | 60 |
| 14427 | 0242–0261; tIR | $A^SA^ST^ST^SG^SC^SA^SA^SG^SC^SC^SA^ST^SA^SG^SC^ST^ST^SC^SA$ | 61 |
| 14428 | 0393–0412; 5' ORF | $C^SG^SG^SC^SA^SA^SG^SG^SC^SA^SG^SC^SA^SA^ST^SA^SC^SC^ST^ST$ | 62 |
| 14909 | 0478–0497; 5' ORF | $C^SC^SC^SA^SG^SC^SA^SA^ST^SG^SA^SC^SA^SG^SA^SC^SA^SG^SC^SA$ | 63 |
| 14910 | 0569–0588; central ORF | $G^SG^ST^SC^ST^SG^SA^SA^SA^SG^SC^SC^SA^SG^SG^SC^SC^SC$ | 64 |
| 14911 | 0745–0764; central ORF | $T^SG^SG^SA^SA^SA^SC^SC^SC^SC^SG^SG^SA^SA^SG^SC^SA^SA$ | 65 |
| 14912 | 0750–0769; central ORF | $G^SG^SC^ST^ST^ST^SG^SG^SG^SA^SA^SC^SC^SC^SC^SG^SG^SA$ | 66 |
| 14913 | 0825–0844; 3' ORF | $T^SC^SA^SG^SA^ST^ST^SC^SA^SG^SG^SA^ST^SC^SC^ST^SG^SG^SA$ | 67 |
| 14914 | 0932–0951; 3' ORF | $C^SC^SC^SA^SG^SG^ST^SG^SA^SA^SG^SC^ST^SC^ST^SG^SA^SC$ | 68 |
| 14915 | 1001–1020; 3' ORF | $C^ST^SG^SC^SG^SC^SG^SA^SA^ST^SC^SC^ST^SG^SC^SC^SC^SC^SA$ | 69 |
| 14916 | 1125–1144; tTR | $C^SA^SG^SG^SC^SC^SC^SG^SA^SA^SG^SG^ST^SA^SA^SG^SG^SC^ST^SG$ | 70 |
| 14917 | 1229–1248; 3' UTR | $T^SC^SA^SG^SC^ST^SA^SG^SC^SA^SC^SG^SG^ST^SG^SC^ST^SG^SA^SA$ | 71 |
| 14918 | 1329–1348; 3' UTR | $G^SG^SC^SC^SA^SG^SC^SA^SA^SA^SC^ST^ST^SG^SC^ST^SC^SG^ST$ | 72 |
| 14919 | 1377–1393; 3' UTR | $C^SC^SA^SC^SC^SA^SC^SA^SG^ST^SG^SG^SC^ST^SC^SA^SG^SC^SC$ | 73 |
| 12912 | −0067 to −0049; 5' UTR | G$^S$G$^S$C$^S$C$^S$A$^S$T$^S$G$^S$A$^S$G$^S$G$^S$G$^S$C$^S$A$^S$A$^S$T$^S$C$^S$T$^S$A$^S$A (2'MO) | 74 |
| 12913 | −0067 to −0047; 5' UTR | G$^S$T$^S$G$^S$G$^S$C$^S$C$^S$A$^S$T$^S$G$^S$A$^S$G$^S$G$^S$G$^S$C$^S$A$^S$A$^S$T$^S$C$^S$T$^S$A$^S$A (2'MO) | 75 |

TABLE 2-continued

Sequences of Oligonucleotides Targeted to Murine B7-1 mRNA

| ISIS # | Target Position; Site | Oligonucleotide Sequence (5' -> 3') and Chemical Modifications | SEQ ID NO: |
|---|---|---|---|
| 13496 | −0067 to −0047; 5' UTR | G$^S$T$^S$G$^S$G$^S$C$^S$C$^S$A$^S$T$^S$G$^S$A$^S$G$^S$G$^S$G$^S$C$^S$A$^S$A$^S$T$^S$C$^S$T$^S$A$^S$A (2'ME) | 75 |
| 13497 | −0067 to −0047; 5' UTR | GTGGCCATGAGGGCAATCTAA (2'ME) | 75 |

TABLE 3

Sequences of Oligonucleotides Targeted to Human B7-2 mRNA

| ISIS # | Target Position*; Site** | Oligonucleotide Sequence (5' -> 3') | SEQ ID NO: |
|---|---|---|---|
| 9133 | 1367–1386; 3'-UTR | T$^S$T$^S$C$^S$C$^S$A$^S$G$^S$G$^S$T$^S$C$^S$A$^S$T$^S$G$^S$A$^S$G$^S$C$^S$C$^S$A$^S$T$^S$T$^S$A | 3 |
| 10715 | scrambled control of # 9133 | G$^S$A$^S$T$^S$T$^S$A$^S$A$^S$C$^S$A$^S$T$^S$T$^S$T$^S$G$^S$G$^S$C$^S$G$^S$C$^S$C$^S$C$^S$A | 76 |
| 9134 | 1333–1352; 3'-UTR | C$^S$A$^S$T$^S$A$^S$A$^S$G$^S$G$^S$T$^S$G$^S$T$^S$G$^S$C$^S$T$^S$C$^S$T$^S$G$^S$A$^S$A$^S$G$^S$T$^S$G | 4 |
| 9135 | 1211–1230; 3'-UTR | T$^S$T$^S$A$^S$C$^S$T$^S$C$^S$A$^S$T$^S$G$^S$G$^S$T$^S$A$^S$A$^S$T$^S$G$^S$T$^S$C$^S$T$^S$T$^S$T$^S$ | 5 |
| 9136 | 1101–1120; tTR | A$^S$T$^S$T$^S$A$^S$A$^S$A$^S$A$^S$A$^S$C$^S$A$^S$T$^S$G$^S$T$^S$A$^S$T$^S$C$^S$A$^S$C$^S$T$^S$T$^S$ | 6 |
| 10716 | (scrambled # 9136) | A$^S$A$^S$A$^S$G$^S$T$^S$T$^S$A$^S$C$^S$A$^S$A$^S$C$^S$A$^S$T$^S$T$^S$A$^S$T$^S$A$^S$T$^S$C$^S$T | 77 |
| 9137 | 0054–0074; 5'-UTR | G$^S$G$^S$A$^S$A$^S$C$^S$A$^S$C$^S$A$^S$G$^S$A$^S$A$^S$G$^S$C$^S$A$^S$A$^S$G$^S$G$^S$G$^S$T$^S$G$^S$G$^S$T | 7 |
| 9138 | 0001–0020; 5'-UTR | C$^S$C$^S$G$^S$T$^S$A$^S$C$^S$C$^S$T$^S$C$^S$C$^S$T$^S$A$^S$A$^S$G$^S$G$^S$C$^S$T$^S$C$^S$C$^S$T | 8 |
| 9139 | 0133–0152; tIR | C$^S$C$^S$C$^S$A$^S$T$^S$A$^S$G$^S$T$^S$G$^S$C$^S$T$^S$G$^S$T$^S$C$^S$A$^S$C$^S$A$^S$A$^S$A$^S$T | 9 |
| 10877 | (scrambled # 9139) | A$^S$G$^S$T$^S$G$^S$C$^S$G$^S$A$^S$T$^S$T$^S$C$^S$T$^S$C$^S$A$^S$A$^S$A$^S$C$^S$C$^S$T$^S$A$^S$C | 78 |
| 10367 | 0073–0092; 5'-UTR | G$^S$C$^S$A$^S$C$^S$A$^S$G$^S$C$^S$A$^S$G$^S$C$^S$A$^S$T$^S$T$^S$C$^S$C$^S$C$^S$A$^S$G$^S$G | 10 |
| 10368 | 0240–0259; 5' ORF | T$^S$T$^S$G$^S$C$^S$A$^S$A$^S$A$^S$T$^S$T$^S$G$^S$G$^S$C$^S$A$^S$T$^S$G$^S$G$^S$C$^S$A$^S$G$^S$G | 11 |
| 10369 | 1122–1141; 3'-UTR | T$^S$G$^S$G$^S$T$^S$A$^S$T$^S$G$^S$G$^S$G$^S$C$^S$T$^S$T$^S$T$^S$A$^S$C$^S$T$^S$C$^S$T$^S$T$^S$T | 12 |
| 10370 | 1171–1190; 3'-UTR | A$^S$A$^S$A$^S$A$^S$G$^S$G$^S$T$^S$T$^S$G$^S$C$^S$C$^S$C$^S$A$^S$G$^S$G$^S$A$^S$A$^S$C$^S$G$^S$G | 13 |
| 10371 | 1233–1252; 3'-UTR | G$^S$G$^S$G$^S$A$^S$G$^S$T$^S$C$^S$C$^S$T$^S$G$^S$G$^S$A$^S$G$^S$C$^S$C$^S$C$^S$C$^S$T$^S$T | 14 |
| 10372 | 1353–1372; 3'-UTR | C$^S$C$^S$A$^S$T$^S$T$^S$A$^S$A$^S$G$^S$C$^S$T$^S$G$^S$G$^S$G$^S$C$^S$T$^S$T$^S$G$^S$G$^S$C$^S$C | 15 |
| 11149 | 0019–0034; 5'-UTR | T$^S$A$^S$T$^S$T$^S$T$^S$G$^S$C$^S$G$^S$A$^S$G$^S$C$^S$T$^S$C$^S$C$^S$C$^S$C | 79 |
| 11151 | 0020–0034; 5'-UTR | T$^S$A$^S$T$^S$T$^S$T$^S$G$^S$C$^S$G$^S$A$^S$G$^S$C$^S$T$^S$C$^S$C$^S$C | 80 |
| 11150 | 0021–0034; 5'-UTR | T$^S$A$^S$T$^S$T$^S$T$^S$G$^S$C$^S$G$^S$A$^S$G$^S$C$^S$T$^S$C$^S$C | 81 |
| 10373 | 0011–0030; 5'-UTR | T$^S$G$^S$C$^S$G$^S$A$^S$G$^S$C$^S$T$^S$C$^S$C$^S$C$^S$C$^S$G$^S$T$^S$A$^S$C$^S$C$^S$T$^S$C$^S$C | 16 |
| 10721 | (scrambled # 10373) | C$^S$G$^S$A$^S$C$^S$A$^S$G$^S$C$^S$T$^S$C$^S$C$^S$T$^S$G$^S$C$^S$G$^S$C$^S$T$^S$C$^S$C$^S$T$^S$C | 82 |
| 10729 | (5'FITC # 10373) | T$^S$G$^S$C$^S$G$^S$A$^S$G$^S$C$^S$T$^S$C$^S$C$^S$C$^S$C$^S$G$^S$T$^S$A$^S$C$^S$C$^S$T$^S$C$^S$C | 16 |
| 10782 | (5'cholesterol # 10373) | T$^S$G$^S$C$^S$G$^S$A$^S$G$^S$C$^S$T$^S$C$^S$C$^S$C$^S$C$^S$G$^S$T$^S$A$^S$C$^S$C$^S$T$^S$C$^S$C | 16 |
| | # 10373 Deletion Derivatives: | | |
| 10373 | 0011–0030; 5'-UTR | T$^S$G$^S$C$^S$G$^S$A$^S$G$^S$C$^S$T$^S$C$^S$C$^S$C$^S$C$^S$G$^S$T$^S$A$^S$C$^S$C$^S$T$^S$C$^S$C | 16 |
| 10888 | 0011–0026; 5'-UTR | A$^S$G$^S$C$^S$T$^S$C$^S$C$^S$C$^S$C$^S$G$^S$T$^S$A$^S$C$^S$C$^S$T$^S$C$^S$C | 83 |
| 10889 | 0015–0030; 5'-UTR | T$^S$G$^S$C$^S$G$^S$A$^S$G$^S$C$^S$T$^S$C$^S$C$^S$C$^S$C$^S$G$^S$T$^S$A$^S$C | 84 |
| 10991 | 0015–0024; 5'-UTR | C$^S$T$^S$C$^S$C$^S$C$^S$C$^S$G$^S$T$^S$A$^S$C | 85 |
| 10992 | 0015–0025; 5'-UTR | G$^S$C$^S$T$^S$C$^S$C$^S$C$^S$C$^S$G$^S$T$^S$A$^S$C | 86 |
| 10993 | 0015–0026; 5'-UTR | A$^S$G$^S$C$^S$T$^S$C$^S$C$^S$C$^S$C$^S$G$^S$T$^S$A$^S$C | 87 |
| 10994 | 0015–0027; 5'-UTR | G$^S$A$^S$G$^S$C$^S$T$^S$C$^S$C$^S$C$^S$C$^S$G$^S$T$^S$A$^S$C | 88 |
| 10995 | 0015–0028; 5'-UTR | C$^S$G$^S$A$^S$G$^S$C$^S$T$^S$C$^S$C$^S$C$^S$C$^S$G$^S$T$^S$A$^S$C | 89 |
| 10996 | 0015–0029; 5'-UTR | G$^S$C$^S$G$^S$A$^S$G$^S$C$^S$T$^S$C$^S$C$^S$C$^S$C$^S$G$^S$T$^S$A$^S$C | 90 |
| 11232 | 0017–0029; 5' UTR | G$^S$C$^S$G$^S$A$^S$G$^S$C$^S$T$^S$C$^S$C$^S$C$^S$C$^S$G$^S$T | 91 |
| | # 10996 Derivatives: | | |
| 10996 | 0015-0029; 5'-UTR | G$^S$C$^S$G$^S$A$^S$G$^S$C$^S$T$^S$C$^S$C$^S$C$^S$C$^S$G$^S$T$^S$A$^S$C | 90 |
| 11806 | (scrambled # 10996) | G$^S$C$^S$C$^S$G$^S$C$^S$C$^S$G$^S$C$^S$C$^S$A$^S$A$^S$G$^S$T$^S$C$^S$T | 92 |
| 11539 | (fully 2'MO # 10996) | G$^S$C$^S$G$^S$A$^S$G$^S$C$^S$T$^S$C$^S$C$^S$C$^S$C$^S$G$^S$T$^S$A$^S$C (2'MO) | 90 |
| 11540 | (control for # 11539) | G$^S$C$^S$C$^S$G$^S$C$^S$C$^S$G$^S$C$^S$C$^S$A$^S$A$^S$G$^S$T$^S$C$^S$T (2'MO) | 92 |
| 11541 | (# 10996 7-base "gapmer") | G$^S$C$^S$G$^S$A$^S$G$^S$C$^S$T$^S$C$^S$C$^S$C$^S$C$^S$G$^S$T$^S$A$^S$C (2'MO) | 90 |
| 11542 | (control for # 11541) | G$^S$C$^S$C$^S$G$^S$C$^S$C$^S$G$^S$C$^S$C$^S$A$^S$A$^S$G$^S$T$^S$C$^S$T (2'MO) | 92 |
| 11543 | (# 10996 9-base "gapmer") | G$^S$C$^S$G$^S$A$^S$G$^S$C$^S$T$^S$C$^S$C$^S$C$^S$C$^S$G$^S$T$^S$A$^S$C (2'MO) | 90 |
| 11544 | (control for # 11543) | G$^S$C$^S$C$^S$G$^S$C$^S$C$^S$G$^S$C$^S$C$^S$A$^S$A$^S$G$^S$T$^S$C$^S$T (2'MO) | 92 |
| 11545 | (# 10996 5' "wingmer") | G$^S$C$^S$G$^S$A$^S$G$^S$C$^S$T$^S$C$^S$C$^S$C$^S$C$^S$G$^S$T$^S$A$^S$C (2'MO) | 90 |
| 11546 | (control for # 11545) | G$^S$C$^S$C$^S$G$^S$C$^S$C$^S$G$^S$C$^S$C$^S$A$^S$A$^S$G$^S$T$^S$C$^S$T (2'MO) | 92 |
| 11547 | (# 10996 3' "wingmer") | G$^S$C$^S$G$^S$A$^S$G$^S$C$^S$T$^S$C$^S$C$^S$C$^S$C$^S$G$^S$T$^S$A$^S$C (2'MO) | 90 |
| 11548 | (control for # 11547) | G$^S$C$^S$C$^S$G$^S$C$^S$C$^S$G$^S$C$^S$C$^S$A$^S$A$^S$G$^S$T$^S$C$^S$T (2'MO) | 92 |
| 12496 | ((2'–5')A$_4$ # 10996) | GCGAGCTCCCCGTAC | 90 |
| 13107 | ((2'–5')A$_4$ # 10996) | G$^S$C$^S$G$^S$A$^S$G$^S$C$^S$T$^S$C$^S$C$^S$C$^S$C$^S$G$^S$T$^S$A$^S$C | 90 |
| 12492 | ((2'–5')A$_4$ # 10996) | G$^S$C$^S$G$^S$A$^S$G$^S$C$^S$T$^S$C$^S$C$^S$C$^S$C$^S$G$^S$T$^S$A$^S$C (2'MO) | 90 |
| 12495 | ((2'–5')A$_4$ # 10996) | G$^S$C$^S$G$^S$A$^S$G$^S$C$^S$T$^S$C$^S$C$^S$C$^S$C$^S$G$^S$T$^S$A$^S$C (2'MO) | 90 |
| 12887 | (1–24 of SEQ ID NO: 1 of WO 95/03408; alternative mRNA) | G$^S$A$^S$G$^S$A$^S$A$^S$G$^S$C$^S$A$^S$A$^S$A$^S$G$^S$C$^S$T$^S$T$^S$T$^S$C$^S$A$^S$C$^S$C$^S$C$^S$T$^S$G$^S$T$^S$G (2'MO) | 93 |

TABLE 3-continued

Sequences of Oligonucleotides Targeted to Human B7-2 mRNA

| ISIS # | Target Position*; Site** | Oligonucleotide Sequence (5' -> 3') | SEQ ID NO: |
|---|---|---|---|
| 12888 | (1–22 of SEQ ID NO: 1 of WO 95/03408; alternative mRNA) | $G^SA^SA^SG^SC^SA^SA^SA^SG^SC^ST^ST^ST^SC^SA^SC^SC^SC^ST^SG^ST^SG$ (2'MO) | 94 |
| 12889 | (1–19 of SEQ ID NO: 1 of WO 95/03408; alternative mRNA) | $G^SC^SA^SA^SA^SG^SC^ST^ST^ST^SC^SA^SC^SC^SC^ST^SG^ST^SG$ (2'MO) | 95 |
| 12890 | 0001–0024 | $C^ST^SC^SC^SC^SG^ST^SA^SC^SC^ST^SC^SC^ST^SA^SA^SG^SG^SC^ST^SC^SC^ST$ (2'MO) | 96 |
| 12891 | 0001–0022 | $C^SC^SC^SC^SG^ST^SA^SC^SC^ST^SC^SC^ST^SA^SA^SG^SG^SC^ST^SC^SC^ST$ (2'MO) | 97 |
| 12892 | 0001–0020 | $C^SC^SG^ST^SA^SC^SC^ST^SC^SC^ST^SA^SA^SG^SG^SC^ST^SC^SC$ (2'MO) | 98 |

TABLE 4

Sequences of Oligonucleotides Targeted to Murine B7-2 mRNA

| ISIS # | Target Position; Site | Oligonucleotide Sequence (5' -> 3') | SEQ ID NO: |
|---|---|---|---|
| 11347 | 1094–1113; 3' UTR | $A^SG^SA^SA^ST^ST^SC^SC^SA^SA^ST^SC^SA^SG^SC^ST^SG^SA^SG^SA$ | 121 |
| 11348 | 1062–1081; 3' UTR | $T^SC^ST^SG^SA^SG^SA^SA^SA^SC^ST^SC^ST^SG^SC^SA^SC^ST^ST^SC$ | 122 |
| 11349 | 1012–1031; 3' UTR | $T^SC^SC^ST^SC^SA^SG^SG^SC^ST^SC^ST^SC^SA^SC^ST^SG^SC^SC^ST$ | 123 |
| 11350 | 0019–1138; 5' UTR | $G^SG^ST^ST^SG^ST^ST^SC^SA^SA^SG^ST^SC^SG^ST^SG^SC^ST^SG$ | 124 |
| 11351 | 0037–0056; 5' UTR | $A^SC^SA^SC^SG^ST^SC^ST^SA^SC^SA^SG^SG^SA^SG^ST^SC^ST^SG^SG$ | 103 |
| 11352 | 0089–0108; tIR | $C^SA^SA^SG^SC^SC^SC^SA^ST^SG^SG^ST^SG^SC^SA^ST^SC^ST^SG^SG$ | 104 |
| 11353 | 0073–0092; tIR | $C^ST^SG^SG^SG^SG^ST^SC^SC^SA^ST^SC^SG^ST^SG^SG^SG^ST^SG^SC$ | 105 |
| 11354 | 0007–0026; 5' UTR | $C^SC^SG^ST^SG^SC^ST^SG^SC^ST^SA^SC^SA^SG^SG^SA^SG^SC^SC$ | 106 |
| 11695 | 0058–0077; 5' UTR | $G^SG^ST^SG^SC^ST^ST^SC^SC^SG^ST^SA^SA^SG^ST^ST^SC^ST^SG^SG$ | 107 |
| 11696 | 0096–0117; tIR | $G^SG^SA^ST^ST^SG^SC^SC^SA^SA^SG^SC^SC^SC^SA^ST^SG^SG^ST^SG$ | 108 |
| 11866 | (scrambled # 11696) | $C^ST^SA^SA^SG^ST^SA^SG^ST^SG^SC^ST^SA^SG^SC^SC^SG^SG^SG^SA$ | 109 |
| 11697 | 0148–0167; 5' ORF | $T^SG^SC^SG^ST^SC^ST^SC^SC^SA^SC^SG^SG^SA^SA^SC^SA^SG^SC$ | 110 |
| 11698 | 0319–0338; 5' ORF | $G^ST^SG^SC^SG^SG^SC^SC^SA^SG^SG^ST^SA^SC^ST^ST^SG^SG^SC$ | 111 |
| 11699 | 0832–0851; 3' ORF | $A^SC^SA^SA^SG^SG^SA^SG^SG^SA^SG^SG^SG^SC^SC^SA^SC^SA^SG^ST$ | 112 |
| 11700 | 0753–0772; 3' ORF | $T^SG^SA^SG^SA^SG^SG^ST^ST^ST^SG^SG^SA^SG^SG^SA^SA^SA^ST^SC$ | 113 |
| 11701 | 0938–0957; 3' ORF | $G^SA^ST^SA^SG^ST^SC^ST^SC^ST^SC^ST^SG^ST^SG^ST^SC^SA^SG^SC^SG^ST$ | 114 |
| 11702 | 0890–0909; 3' ORF | $G^ST^ST^SG^SC^ST^SG^SG^SG^SC^SC^ST^SG^SC^ST^SA^SG^SG^SC^ST$ | 115 |
| 11865 | (scrambled # 11702) | $C^ST^SA^SG^SG^ST^SC^ST^SC^SG^ST^SC^SG^ST^SC^SG^SG^ST^SG^SG$ | 116 |
| 11703 | 1003–1022; tTR | $T^SC^ST^SC^SA^SC^ST^SG^SC^SC^ST^ST^SC^SA^SC^ST^SC^ST^SG^SC$ | 117 |
| 13100 | Exon 1 (Borriello et al., J. Immun., 1995, 155, 5490; 5' UTR of alternative mRNA) | $G^ST^SA^SC^SC^SA^SG^SA^ST^SG^SA^SA^SG^SG^ST^ST^SA^ST^SC^SA^SA$ (2' MO) | 118 |
| 13101 | Exon 4 (Borriello et al.; 5' UTR of alternative mRNA) | $C^ST^ST^ST^SG^SG^SA^SG^SA^ST^ST^SA^ST^ST^SC^SG^SA^SG^ST^ST$ (2' MO) | 119 |
| 13102 | Exon 5 (Borriello et al.; 5' UTR of alternative mRNA) | $G^SC^SA^SA^SG^ST^SG^ST^SA^SA^SA^SG^SC^SC^SC^ST^SG^SA^SG^ST$ (2' MO) | 120 | cDNA clones:

A cDNA encoding the sequence for human B7-1 was isolated by using the reverse transcription/polymerase chain reaction (RT-PCR). Poly A+ RNA from Daudi cells (ATCC accession No. CCL 213) was reverse transcribed using oligo-dT primer under standard conditions. Following a 30 minute reaction at 42° C. and heat inactivation, the reaction mixture (20 μL) was brought to 100 μL with water. A 10 μL aliquot from the RT reaction was then amplified in a 50 μL PCR reaction using the 5' primer, 5'-GAT-CAG-GGT-ACC-CCA-AAG-AAA-AAG-TGA-TTT-GTC-ATT-GC-3' (sense, SEQ ID NO: 20), and the 3' primer, 5'-GAT-AGC-CTC-GAG-GAT-AAT-GAA-TTG-GCT-GAC-AAG-AC-3' (antisense, SEQ ID NO: 21).

The primers included unique restriction sites for subcloning of the PCR product into the vector pcDNA-3 (Invitrogen, San Diego, Calif.). The 5' primer was designed to have identity with bases 1 to 26 of the published human B7-1 sequence (Freeman et al., *J. Immmunol.*, 1989, 143, 2714; positions 13–38 of the primer) and includes a Kpn I restriction site (positions 7–12 of the primer) for use in cloning. The 3' primer was designed to be complementary to bases 1450 to 1471 of the published sequence for B7-1 (positions 14–35 of the primer) and includes a Xho I restriction site (positions 7–12 of the primer). Following PCR, the reaction was extracted with phenol and precipitated using ethanol. The product was digested with the appropriate restriction enzymes and the full-length fragment purified by agarose gel and ligated into the vector pcDNA-3 (Invitrogen, San Diego, Calif.) prepared by digesting with the same enzymes. The resultant construct, pcB7-1, was confirmed by restriction mapping and DNA sequence analysis using standard procedures. A mouse B7-1 clone, pcmB7-1, was isolated in a similar manner by RT-PCR of RNA isolated from a murine B-lymphocyte cell line, 70Z3.

A cDNA encoding the sequence for human B7-2, position 1 to 1391, was also isolated by RT-PCR. Poly A+ RNA from Daudi cells (ATCC accession No. CCL 213) was reverse transcribed using oligo-dT primer under standard conditions. Following a 30 minute reaction at 42° C. and heat inactivation, the reaction mixture (20 µL) was brought to 100 µL with water. A 10 µL aliquot from the RT reaction was then amplified in a 50 µL PCR reaction using the 5' primer, 5'-GAT-CAG-GGT-ACC-AGG-AGC-CTT-AGG-AGG-TAC-GG-3' (sense, SEQ ID NO: 1), and the 3' primer, 5'-GAT-AGC-CTC-GAG-TTA-TTT-CCA-GGT-CAT-GAG-CCA-3' (antisense, SEQ ID NO: 2).

The 5' primer was designed to have identity with bases 1–20 of the published B7-2 sequence (Azuma et al., Nature, 1993, 366, 76 and Genbank Accession No. L25259; positions 13–32 of the primer) and includes a Kpn I site (positions 7–12 of the primer) for use in cloning. The 3' primer was designed to have complementarity to bases 1370–1391 of the published sequence for B7-2 (positions 13–33 of the primer) and includes an Xho I restriction site (positions 7–12 of the primer). Following PCR, the reaction was extracted with phenol and precipitated using ethanol. The product was digested with Xho I and Kpn I, and the full-length fragment purified by agarose gel and ligated into the vector pcDNA-3 (Invitrogen, San Diego, Calif.) prepared by digesting with the same enzymes. The resultant construct, pcB7-2, was confirmed by restriction mapping and DNA sequence analysis using standard procedures.

A mouse B7-2 clone, pcmB7-2, was isolated in a similar manner by RT-PCR of RNA isolated from P388D1 cells using the 5' primer, 5'-GAT-CAG-GGT-ACC-AAG-AGT-GGC-TCC-TGT-AGG-CA (sense, SEQ ID NO: 99), and the 3' primer, 5'-GAT-AGC-CTC-GAG-GTA-GAA-TTC-CAA-TCA-GCT-GA (antisense, SEQ ID NO: 100).

The 5' primer has identity with bases 1–20, whereas the 3' primer is complementary to bases 1096–1115, of the published murine B7-2 sequence (Chen et al., J. Immun., 1994, 152, 4929). Both primers incorporate the respective restriction enzyme sites found in the other 5' and 3' primers used to prepare cDNA clones. The RT-PCR product was restricted with Xho I and Kpn I and ligated into pcDNA-3 (Invitrogen, San Diego, Calif.).

Other cDNA clones, corresponding to mRNAs resulting from alternative splicing events, are cloned in like fashion, using primers containing the appropriate restriction sites and having identity with (5' primers), or complementarity to (3' primers), the selected B7 mRNA.

Example 2

Modulation of hB7-1 Expression by Oligonucleotides

The ability of oligonucleotides to inhibit B7-1 expression was evaluated by measuring the cell surface expression of B7-1 in transfected COS-7 cells by flow cytometry.

Methods:

A T-175 flask was seeded at 75% confluency with COS-7 cells (ATCC accession No. CRL 1651). The plasmid pcB7-1 was introduced into cells by standard calcium phosphate transfection. Following a 4 hour transfection, the cells were trypsinized and seeded in 12-well dishes at 80% confluency. The cells were allowed to adhere to the plastic for 1 hour and were then washed with phosphate-buffered saline (PBS). OptiMEM™ (GIBCO-BRL, Gaithersburg, Md.) medium was added along with 15 µg/mL of Lipofectin™ (GIBCO-BRL, Gaithersburg, Md.) and oligonucleotide at the indicated concentrations. After four additional hours, the cells were washed with phosphate buffered saline (PBS) and incubated with fresh oligonucleotide at the same concentration in DMEM (Dulbecco et al., Virol., 1959, 8, 396; Smith et al., Virol., 1960, 12, 185) with 10% fetal calf sera (FCS).

In order to monitor the effects of oligonucleotides on cell surface expression of B7-1, treated COS-7 cells were harvested by brief trypsinization 24–48 hours after oligonucleotide treatment. The cells were washed with PBS, then resuspended in 100 µL of staining buffer (PBS, 0.2% BSA, 0.1% azide) with 5 µL conjugated anti-B7-1-antibody (i.e., anti-hCD80-FITC, Ancell, Bayport, Minn.; FITC: fluorescein isothiocyanate). The cells were stained for 30 minutes at 4° C., washed with PBS, resuspended in 300 µL containing 0.5% paraformaldehyde. Cells were harvested and the fluorescence profiles were determined using a flow cytometer.

Results:

The oligonucleotides shown in Table 1 were evaluated, in COS-7 cells transiently expressing B7-1 cDNA, for their ability to inhibit B7-1 expression. The results (FIG. 1) identified ISIS 13805, targeted to the translation initiation codon region, and ISIS 13812, targeted to the 3' untranslated region (UTR), as the most active oligonucleotides with greater than 50% inhibition of B7-1 expression. These oligonucleotides are thus highly preferred. ISIS 13799 (targeted to the 5' untranslated region), ISIS 13802 (targeted to the 5' untranslated region), ISIS 13806 and 13807 (both targeted to the 5' region of the ORF), and ISIS 13810 (targeted to the central portion of the ORF) demonstrated 35% to 50% inhibition of B7-1 expression. These sequences are therefore also preferred.

Figure 2:
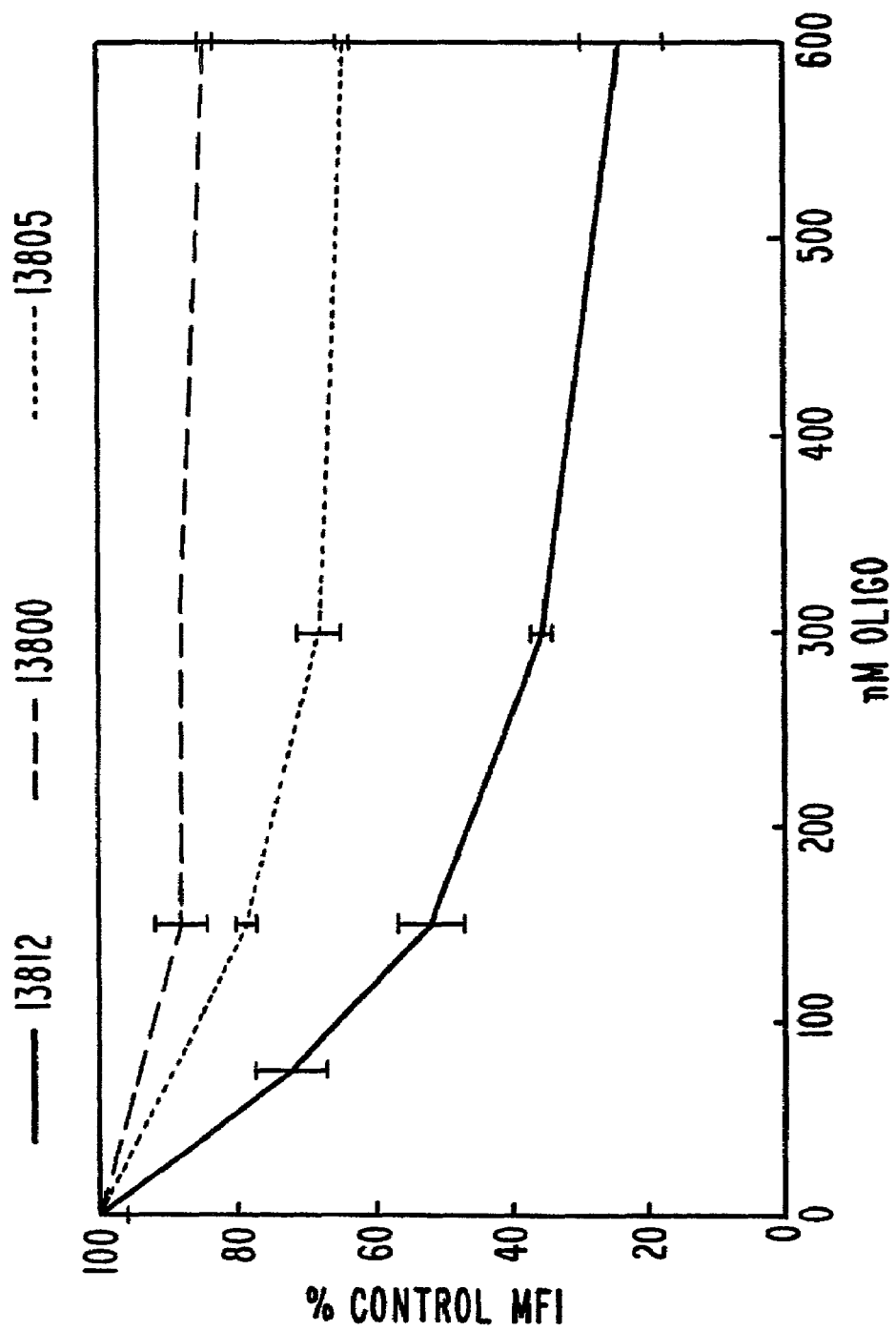
FIG. 2 is a dose-response curve showing the inhibitory effect of oligonucleotides on cell surface expression of B7-1 protein. Solid line, ISIS 13812; dashed line, ISIS 13800; dotted line, ISIS 13805.

Oligonucleotide ISIS 13800, which showed essentially no inhibition of B7-1 expression in the flow cytometry assay, and ISIS Nos. 13805 and 13812 were then evaluated for their ability to inhibit cell surface expression of B7-1 at various concentrations of oligonucleotide. The results of these assays are shown in FIG. 2. ISIS 13812 was a superior inhibitor of B7-1 expression with an $IC_{50}$ of approximately 150 nM. ISIS 13800, targeted to the 5' UTR, was essentially inactive.

Example 3

Modulation of hB7-2 Protein by Oligonucleotides

In an initial screen, the ability of hB7-2 oligonucleotides to inhibit B7-2 expression was evaluated by measuring the cell surface expression of B7-2 in transfected COS-7 cells by flow cytometry. The methods used were similar to those given in Example 2, with the exceptions that (1) COS-7 cells were transfected with the plasmids pbcB7-2 or BBG-58, a human ICAM-1 (CD54) expression vector (R&D Systems, Minneapolis, Minn.) introduced into cells by standard calcium phosphate transfection, (2) the oligonucleotides used were those described in Table 2, and (3) a conjugated anti-B7-2 antibody (i.e., anti-hCD86-FITC or anti-CD86-PE, PharMingen, San Diego, Calif.; PE: phycoerythrin) was used during flow cytometry.

Figure 3:
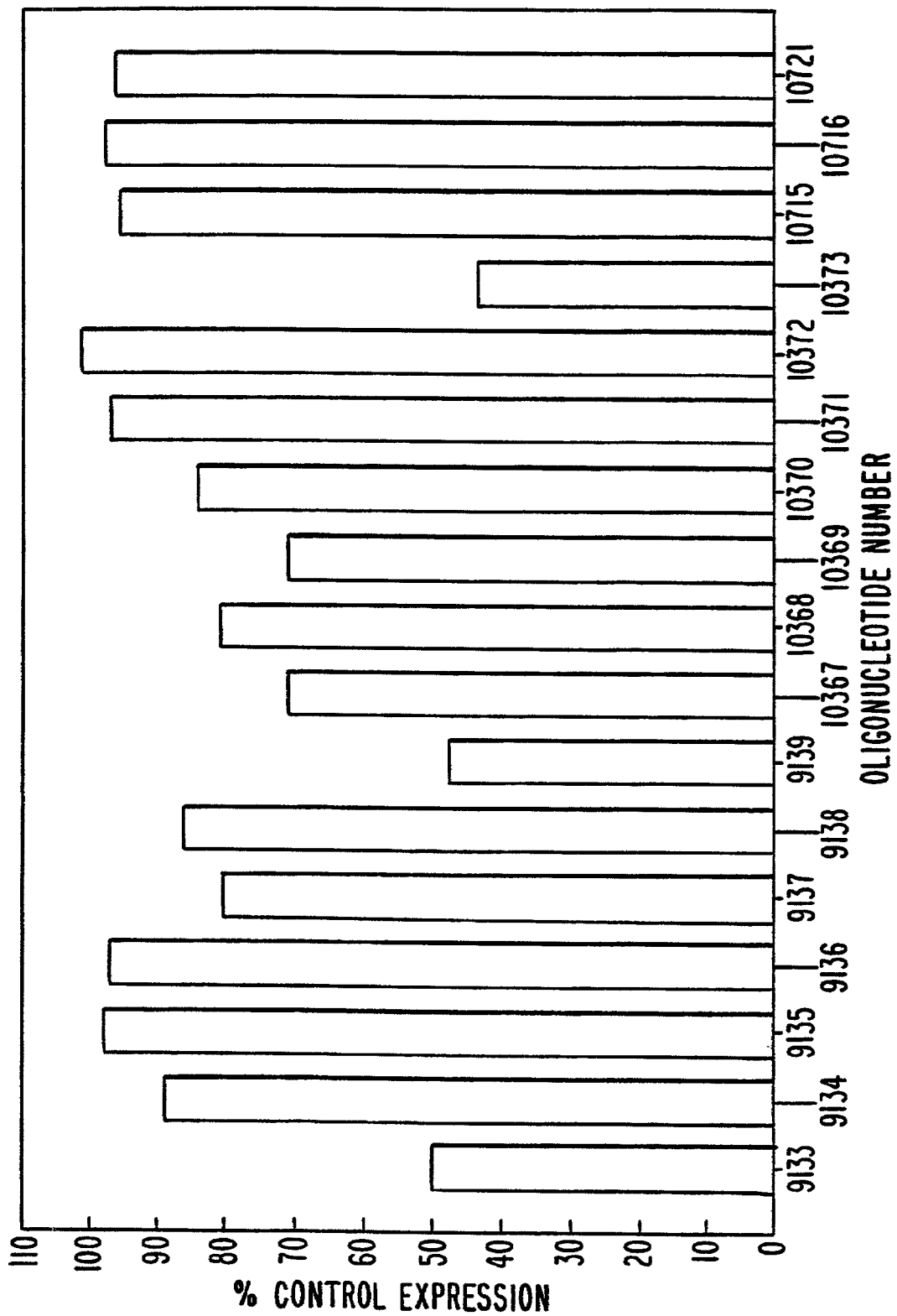
FIG. 3 is a bar graph showing the inhibitory effect of the indicated oligonucleotides on cell surface expression of B7-2 in COS-7 cells.

Results:

The results are shown in FIG. 3. At a concentration of 200 nM, ISIS 9133, ISIS 9139 and ISIS 10373 exhibited inhibitory activity of 50% or better and are therefore highly preferred. These oligonucleotides are targeted to the 3' untranslated region (ISIS 9133), the translation initiation codon region (ISIS 9139) and the 5' untranslated region (ISIS 10373). At the same concentration, ISIS 10715, ISIS 10716 and ISIS 10721, which are scrambled controls for ISIS 9133, ISIS 9139 and ISIS 10373, respectively, showed no inhibitory activity. Treatment with ISIS 10367 and ISIS 10369 resulted in greater than 25% inhibition, and these oligonucleotides are thus also preferred. These oligonucleotides are targeted to the 5' (ISIS 10367) and 3' (ISIS 10369) untranslated regions.

Example 4

Modulation of hB7-2 mRNA by Oligonucleotides

Methods:

For ribonuclease protection assays, cells were harvested 18 hours after completion of oligonucleotide treatment using a Totally RNA™ kit (Ambion, Austin, Tex.). The probes for the assay were generated from plasmids pcB7-2 (linearized by digestion with Bgl II) and pTRI-b-actin (Ambion Inc., Austin, Tex.). In vitro transcription of the linearized plasmid from the SP6 promoter was performed in the presence of α-$^{32}$P-UTP (800 Ci/mmole) yielding an antisense RNA complementary to the 3' end of B7-2 (position 1044–1391). The probe was gel-purified after treatment with DNase I to remove DNA template. Ribonuclease protection assays were carried out using an RPA II™ kit (Ambion) according to the manufacturer's directions. Total RNA (5 μg) was hybridized overnight, at 42° C., with 10$^5$ cpm of the B7-2 probe or a control beta-actin probe. The hybridization reaction was then treated, at 37° C. for 30 minutes, with 0.4 units of RNase A and 2 units of RNase T1. Protected RNA was precipitated, resuspended in 10 μL of gel loading buffer and electrophoresed on a 6% acrylamide gel with 50% w/v urea at 20 W. The gel was then exposed and the lanes quantitated using a PhosphorImager (Molecular Dynamics, Sunnyvale, Calif.) essentially according to the manufacturer's instructions.

Results:

The extent of oligonucleotide-mediated hB7-2 mRNA modulation generally paralleled the effects seen for hB7-2 protein (Table 5). As with the protein expression (flow cytometry) assays, the most active oligonucleotides were ISIS 9133, ISIS 9139 and 10373. None of the oligonucleotides tested had an inhibitory effect on the expression of b-actin mRNA in the same cells.

TABLE 5

Activities of Oligonucleotides Targeted to hB7-2 mRNA

| ISIS NO. | SEQ ID NO. | % Control Protein | % Control RNA Expression |
|---|---|---|---|
| 9133 | 3 | 70.2 | 46.0 |
| 9134 | 4 | 88.8 | 94.5 |
| 9135 | 5 | 98.2 | 83.4 |
| 9136 | 6 | 97.1 | 103.1 |
| 9137 | 7 | 80.5 | 78.1 |
| 9138 | 8 | 86.4 | 65.9 |
| 9139 | 9 | 47.9 | 32.6 |
| 10367 | 10 | 71.3 | 52.5 |
| 10368 | 11 | 81.0 | 84.5 |
| 10369 | 12 | 71.3 | 81.5 |
| 10370 | 13 | 84.3 | 83.2 |
| 10371 | 14 | 97.3 | 92.9 |
| 10372 | 15 | 101.7 | 82.5 |
| 10373 | 16 | 43.5 | 32.7 |

Example 5

Additional hB7-1 and hB7-2 Oligonucleotides

Oligonucleotides having structures and/or sequences that were modified relative to the oligonucleotides identified during the initial screening were prepared. These oligonucleotides were evaluated for their ability to modulate human B7-2 expression using the methods described in the previous Examples.

Figure 4:
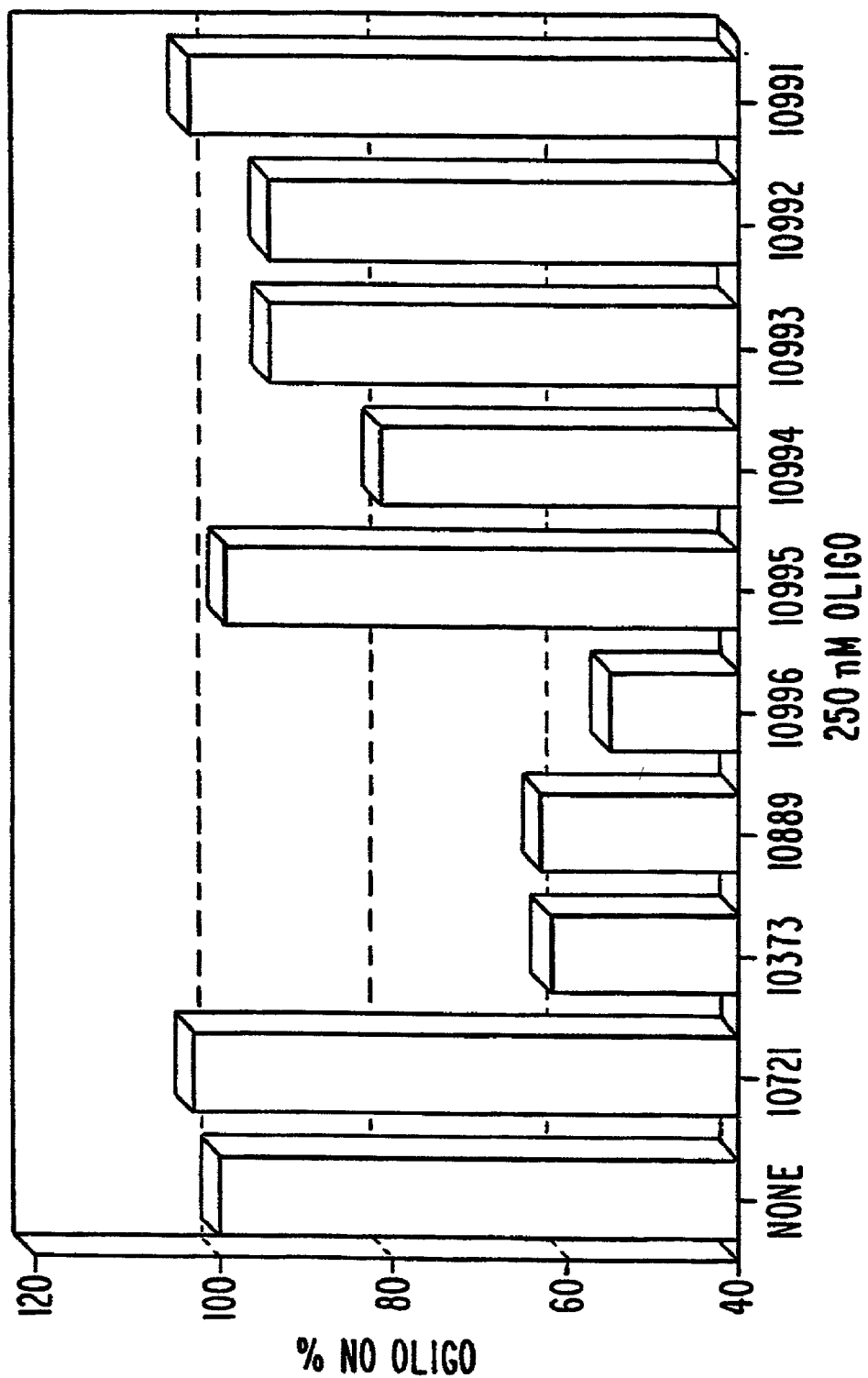
FIG. 4 is a bar graph showing the inhibitory effect of the indicated oligonucleotides, including ISIS 10373 (a 20-mer) and ISIS 10996 (a 15-mer) on cell surface expression of B7-2 in COS-7 cells.

ISIS 10996, an oligonucleotide having a 15 nucleotide sequence derived from the 20 nucleotide sequence of ISIS 10373, was also prepared and evaluated. ISIS 10996 comprises 15 nucleotides, 5'-GCG-AGC-TCC-CCG-TAC (SEQ ID NO: 90) contained within the sequence of ISIS 10373. Both ISIS 10373 and 10996 overlap a potential stem-loop structure located within the B7-2 message comprising bases 1–67 of the sequence of hB7-2 presented by Azuma et al. (Nature, 1993, 366, 76). While not intending to be bound by any particular theory regarding their mode(s) of action, ISIS 10373 and ISIS 10996 have the potential to bind as loop 1 pseudo-half-knots at a secondary structure within the target RNA. U.S. Pat. No. 5,512,438, which issued Apr. 30, 1996, the contents of which are hereby incorporated by reference, describes methods for modulating gene expression by the formation of pseudo-half-knots. Regardless of their mode(s) of action, despite having a shorter length than ISIS 10373, the 15-mer ISIS 10996 is as (or more) active in the B7-2 protein expression assay than the 20-mer from which it is derived (FIG. 4; ISIS 10721 is a scrambled control for ISIS 10373). A related 16-mer, ISIS 10889, was also active in the B7-2 protein expression assay. However, a structurally related 14-mer (ISIS 10995), 13-mer (ISIS 10994), 12-mer (ISIS 10993), 11-mer (ISIS 10992) and 10-mer (ISIS 10991) exhibited little or no activity in this assay. ISIS 10996 was further derivatized in the following ways.

ISIS 10996 derivatives having 2' methoxethoxy substitutions were prepared, including a fully substituted derivative (ISIS 11539), "gapmers" (ISIS 11541 and 11543) and "wingmers" (ISIS 11545 and 11547). As explained in Example 5, the 2' methoxyethoxy substitution prevents the action of some nucleases (e.g., RNase H) but enhances the affinity of the modified oligonucleotide for its target RNA molecule. These oligonucleotides are tested for their ability to modulate hB7-2 message or function according to the methods of Examples 3, 4, 7 and 8.

ISIS 10996 derivatives were prepared in order to be evaluated for their ability to recruit RNase L to a target RNA molecule, e.g., hB7-2 message. RNase L binds to, and is activated by, (2'–5') (A)$_n$, which is in turn produced from ATP by (2'–5')(A)$_n$, synthetase upon activation by, e.g., interferon. RNase L has been implicated in antiviral mechanisms and in the regulation of cell growth as well (Sawai, Chemica scripta, 1986, 21, 169; Charachon et al., Biochemistry, 1990, 29, 2550). The combination of anti-B7 oligonucleotides conjugated to (2'–5') (A)$_n$ is expected to result in the activation of RNase L and its targeting to the B7 message complementary to the oligonucleotide sequence. The following oligonucleotides have identical sequences (i.e., that of ISIS 10996) and identical (2'-5')(A)$_4$ "caps" on their 5' termini: ISIS 12492, 12495, 12496 and 13107. The adenosyl residues have 3' hydroxyl groups and are linked to each other by phosphorothioate linkages. The (3'–5') portion of the oligonucleotide, which has a sequence complementary to a portion of the human B7-2 RNA, is conjugated to the (2'–5') (A)$_4$ "cap" via a phosphorothioate linkage from the 5' residue of the (3'–5') portion of the oligonucleotide to an n-aminohexyl linker which is bonded to the "cap" via another phosphorothioate linkage. In order to test a variety of chemically diverse oligonucleotides of this type for their ability to recruit RNase L to a specific message, different chemical modifications were made to this set of four oligonucleotides as follows. ISIS 12496 consists of unmodified oligonucleotides in the (3'–5') portion of the oligonucleotide. In ISIS 13107, phosphorothioate linkages replace the phosphate linkages found in naturally occurring nucleic acids. Phosphorothioate linkages are also employed in ISIS 12492 and 12495, which additionally have 2'-methoxyethoxy substitutions. These oligonucleotides are tested for their ability to modulate hB7-2 message or function according to the methods of Examples 3, 4, 7 and 8.

Derivatives of ISIS 10996 having modifications at the 2' position were prepared and evaluated. The modified oligonucleotides included ISIS 11539 (fully 2'-O-methyl), ISIS 11541 (having 2'-O-methyl "wings" and a central 7-base "gap"), ISIS 11543 (2'-O-methyl wings with a 9-base gap), ISIS 11545 (having a 5' 2'-O-methyl wing) and ISIS 11547 (having a 3' 2'-O-methyl wing). The results of assays of 2'-O-methyl oligonucleotides were as follows. ISIS 11539, the fully 2'O-methyl version of ISIS 10996, was not active at all in the protein expression assay. The gapped and winged oligonucleotides (ISIS 11541, 11543, 11545 and 11547) each showed some activity at 200 nM (i.e., from 60 to 70% expression relative to untreated cells), but less than that demonstrated by the parent compound, ISIS 10996 (i.e., about 50% expression). Similar results were seen in RNA expression assays.

ISIS 10782, a derivative of ISIS 10373 to which cholesterol has been conjugated via a 5' n-aminohexyl linker, was prepared. Lipophilic moieties such as cholesterol have been reported to enhance the uptake by cells of oligonucleotides in some instances, although the extent to which uptake is enhanced, if any, remains unpredictable. ISIS 10782, and other oligonucleotides comprising lipophilic moieties, are tested for their ability to modulate B7-2 message or function according to the methods of Examples 3, 4, 7 and 8.

A series of 2'-methoxyethoxy (herein, "2'ME") and 2'-fluoride (herein, "2'F") "gapmer" derivatives of the hB7-1 oligonucleotides ISIS 12361 (ISIS Nos. 12348 and 12473, respectively), ISIS 12362 (ISIS Nos. 12349 and 12474), ISIS 12363 (ISIS Nos. 12350 and 12475), ISIS 12364 (ISIS Nos. 12351 and 12476), ISIS 12365 (ISIS Nos. 12352 and 12477), ISIS 12366 (ISIS Nos. 12353 and 12478), ISIS 12367 (ISIS Nos. 12354 and 12479), ISIS 12368 (ISIS Nos. 12355 and 12480), ISIS 12369 (ISIS Nos. 12356 and 12481) and ISIS 12370 (ISIS Nos. 12357 and 12482) were prepared. The central, non-2'-modified portions ("gaps") of these derivatives support RNase H activity when the oligonucleotide is bound to its target RNA, even though the 2'-modified portions do not. However, the 2'-modified "wings" of these oligonucleotides enhance their affinity to their target RNA molecules (Cook, Chapter 9 In: Antisense Research and Applications, Crooke et al., eds., CRC Press, Boca Raton, 1993, pp. 171–172).

Another 2' modification is the introduction of a methoxy (MO) group at this position. Like 2'ME- and 2'F-modified oligonucleotides, this modification prevents the action of RNase H on duplexes formed from such oligonucleotides and their target RNA molecules, but enhances the affinity of an oligonucleotide for its target RNA molecule. ISIS 12914 and 12915 comprise sequences complementary to the 5' untranslated region of alternative hB7-1 mRNA molecules, which arise from alternative splicing events of the primary hB7-1 transcript. These oligonucleotides include 2' methoxy modifications, and the enhanced target affinity resulting therefrom may allow for greater activity against alternatively spliced B7-1 mRNA molecules which may be present in low abundance in some tissues (Inobe et al., *J. Immun.*, 1996, 157, 582). Similarly, ISIS 13498 and 13499, which comprise antisense sequences to other alternative hB7-1 mRNAs, include 2' methoxyethoxy modifications in order to enhance their affinity for their target molecules, and 2' methoxyethoxy or 2'methoxy substitutions are incorporated into the hB7-2 oligonucleotides ISIS 12912, 12913, 13496 and 13497. These oligonucleotides are tested for their ability to modulate hB7-1 essentially according to the methods of Example 2 or hB7-2 according to the methods of Examples 3, 4, 7 and 8, with the exception that, when necessary, the target cells are transfected with a cDNA clone corresponding to the appropriate alternatively spliced B7 transcript.

Example 6

Specificity of Antisense Modulation

Figure 5:
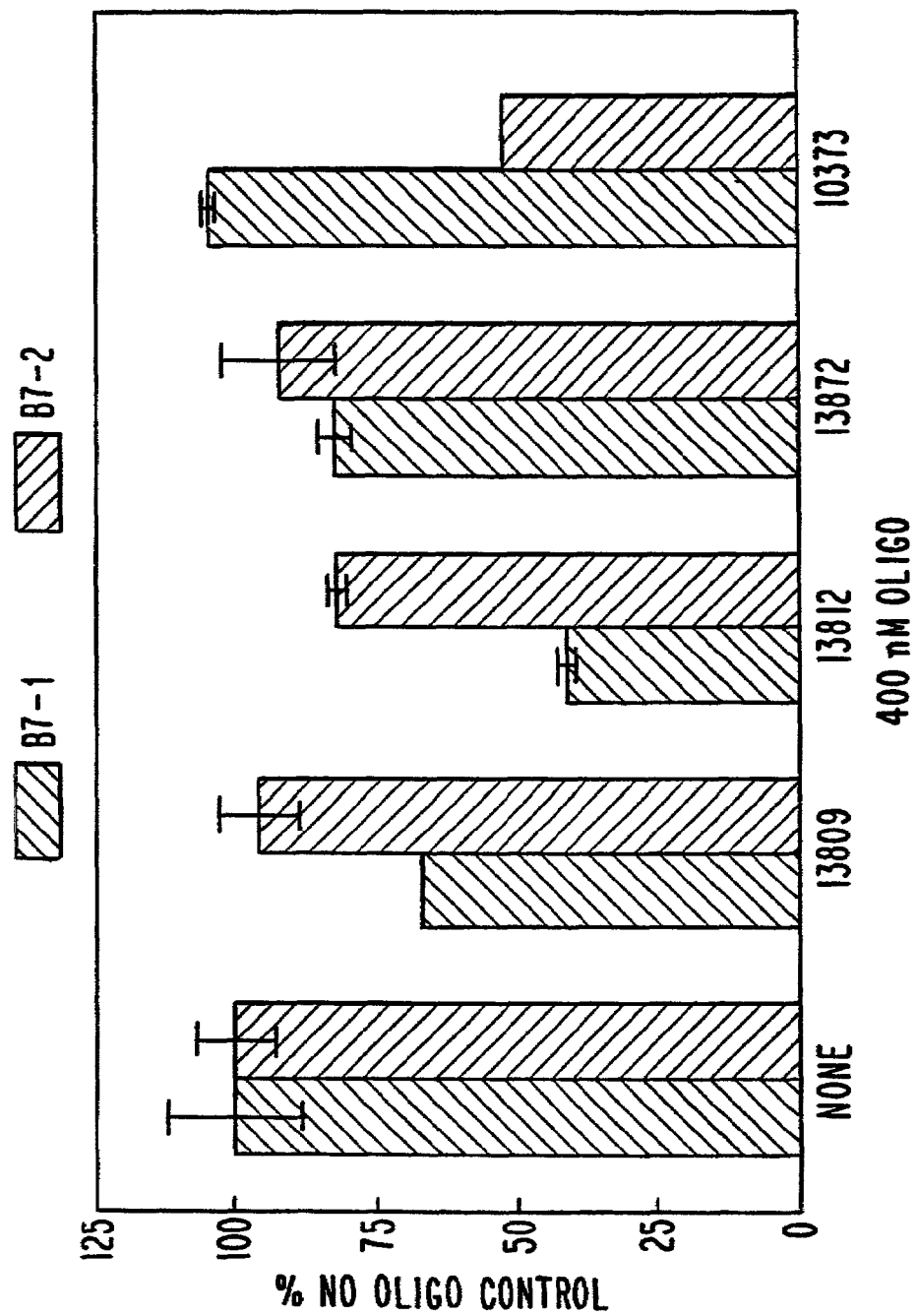
FIG. 5 is a bar graph showing the specificity of inhibition of B7-1 or B7-2 protein expression by oligonucleotides. Cross-hatched bars, B7-1 levels; striped bars, B7-2 levels.

Several oligonucleotides of the invention were evaluated in a cell surface expression flow cytometry assay to determine the specificity of the oligonucleotides for B7-1 as contrasted with activity against B7-2. The oligonucleotides tested in this assay included ISIS 13812, an inhibitor of B7-1 expression (FIG. 1; Example 2) and ISIS 10373, an inhibitor of B7-2 expression (FIG. 3; Example 3). The results of this assay are shown in FIG. 5. ISIS 13812 inhibits B7-1 expression with little or no effect on B7-2 expression. As is also seen in FIG. 5, ISIS 10373 inhibits B7-2 expression with little or no effect on B7-1 expression. ISIS 13872 (SEQ ID NO: 37, AGT-CCT-ACT-ACC-AGC-CGC-CT), a scrambled control of ISIS 13812, and ISIS 13809 (SEQ ID NO: 51) were included in these assays and demonstrated essentially no activity against either B7-1 or B7-2.

Example 7

Modulation of hB7-2 Expression by Oligonucleotides in Antigen Presenting Cells

The ability of ISIS 10373 to inhibit expression from the native B7-2 gene in antigen presenting cells (APCs) was evaluated as follows.

Methods:

Monocytes were cultured and treated with oligonucleotides as follows. For dendritic cells, EDTA-treated blood was layered onto Polymorphprep™ (1.113 g/mL; Nycomed, Oslo, Norway) and sedimented at 500×g for 30 minutes at 20° C. Mononuclear cells were harvested from the interface. Cells were washed with PBS, with serum-free RPMI media (Moore et al., *N.Y. J. Med.*, 1968, 68, 2054) and then with RPMI containing 5% fetal bovine serum (FBS). Monocytes were selected by adherence to plastic cell culture cell culture dishes for 1 h at 37° C. After adherence, cells were treated with oligonucleotides in serum-free RPMI containing Lipofectin™ (8 µg/mL). After 4 hours, the cells were washed. Then RPMI containing 5% FBS and oligonucleotide was added to cells along with interleukin-4 (IL-4; R&D Systems, Minneapolis, Minn.) (66 ng/mL) and granulocyte-macrophage colony-stimulating factor (GM-CSF; R&D Systems, Minneapolis, Minn.) (66 ng/mL) to stimulate differentiation (Romani et al., *J. Exp. Med.*, 1994, 180, 83, 1994). Cells were incubated for 48 hours, after which cell surface expression of various molecules was measured by flow cytometry.

Mononuclear cells isolated from fresh blood were treated with oligonucleotide in the presence of cationic lipid to promote cellular uptake. As a control oligonucleotide, ISIS 2302 (an inhibitor of ICAM-1 expression; SEQ ID NO: 17) was also administered to the cells. Expression of B7-2 protein was measured by flow cytometry according to the methods of Example 2. Monoclonal antibodies not described in the previous Examples included anti-hCD3 (Ancell, Bayport, Minn.) and anti-HLA-DR (Becton Dickinson, San Jose, Calif.).

Figure 6:
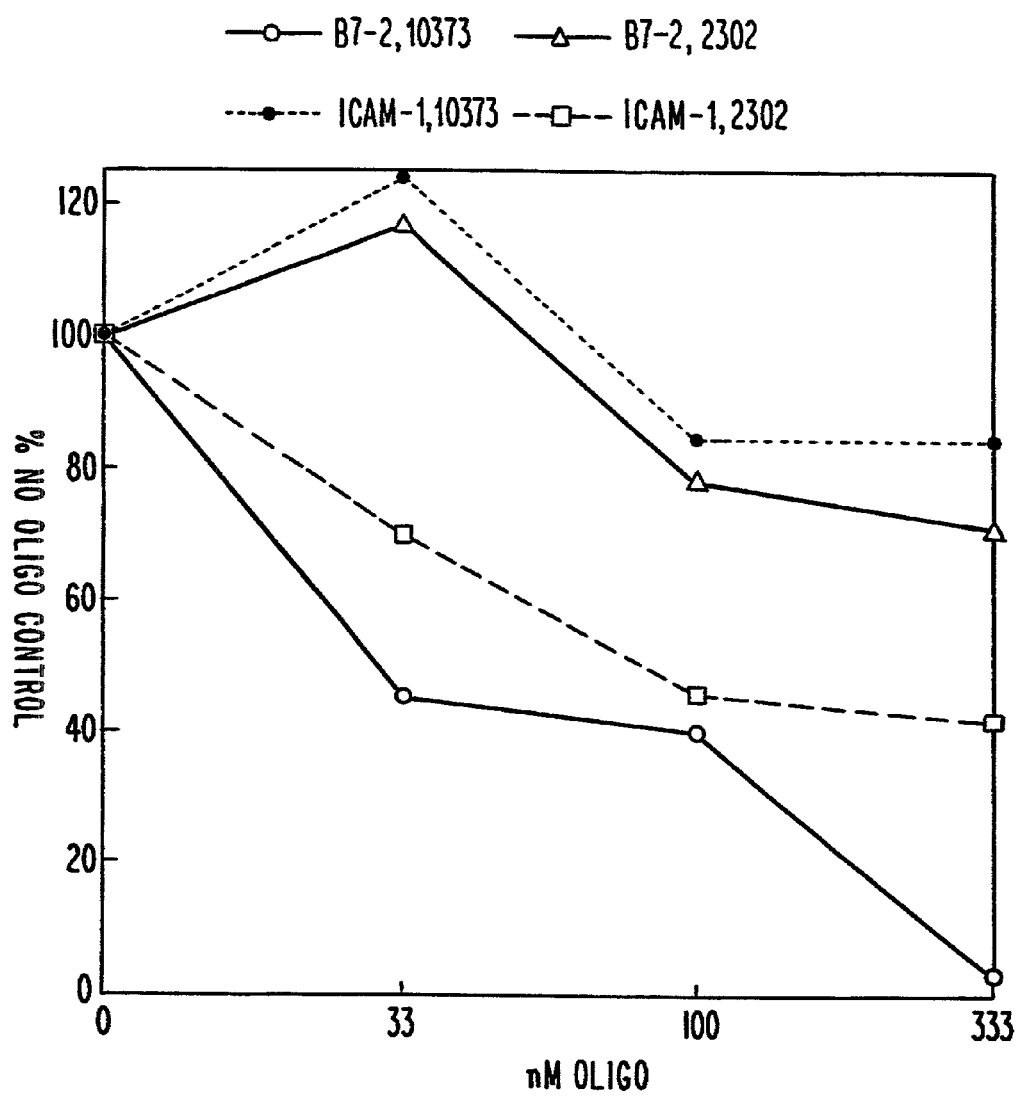
FIG. 6 is a dose-response curve showing the inhibitory effect of oligonucleotides having antisense sequences to ICAM-1 (ISIS 2302) or B7-2 (ISIS 10373) on cell surface expression of the ICAM-1 and B7-2 proteins. Solid line with X's, levels of B7-1 protein on cells treated with ISIS 10373; dashed line with asterisks, levels of ICAM-1 protein on cells treated with ISIS 10373; solid line with triangles, levels of B7-1 protein on cells treated with ISIS 2302; solid line with squares, levels of ICAM-1 protein on cells treated with ISIS 10373.

Results:

As shown in FIG. 6, ISIS 10373 has a significant inhibitory effect on B7-2 expression with an $IC_{50}$ of approximately 250 nM. ISIS 10373 had only a slight effect on ICAM-1 expression even at a dose of 1 µM. ISIS 2302 (SEQ ID NO: 17), a control oligonucleotide which has been shown to inhibit ICAM-1 expression, had no effect on B7-2 expression, but significantly decreased ICAM-1 levels with an $IC_{50}$ of approximately 250 nM. Under similar conditions, ISIS 10373 did not affect the cell surface expression of B7-1, HLA-DR or CD3 as measured by flow cytometry.

Example 8

Modulation of T Cell Proliferation by Oligonucleotides

The ability of ISIS 2302 and ISIS 10373 to inhibit T cell proliferation was evaluated as follows. Monocytes treated with oligonucleotide and cytokines (as in Example 6) were used as antigen presenting cells in a T cell proliferation assay. The differentiated monocytes were combined with CD4+ T cells from a separate donor. After 48 hours, proliferation was measured by [$^3$H] thymidine incorporation.

Methods:

For T cell proliferation assays, cells were isolated from EDTA-treated whole blood as described above, except that a faster migrating band containing the lymphocytes was harvested from just below the interface. Cells were washed as described in Example 6 after which erythrocytes were removed by $NH_4Cl$ lysis. T cells were purified using a T cell enrichment column (R&D Systems, Minneapolis, Minn.) essentially according to the manufacturer's directions. CD4+ T cells were further enriched from the entire T cell population by depletion of CD8+ cells with anti-CD8-conjugated magnetic beads (AMAC, Inc., Westbrook, Me.) according to the manufacturer's directions. T cells were determined to be >80% CD4+ by flow cytometry using Cy-chrome-conjugated anti-CD4 mAb (PharMingen, San Diego, Calif.).

Antigen presenting cells (APCs) were isolated as described in Example 6 and treated with mitomycin C (25 µg/mL) for 1 hour then washed 3 times with PBS. APCs ($10^5$ cells) were then combined with $4 \times 10^4$ CD4+ T cells in 350 µL of culture media. Where indicated, purified CD3 mAb was also added at a concentration of 1 µg/mL. During the last 6 hours of the 48 hour incubation period, proliferation was measured by determining uptake of 1.5 uCi of [$^3$H]-thymidine per well. The cells were harvested onto filters and the radioactivity measured by scintillation counting.

Figure 7:
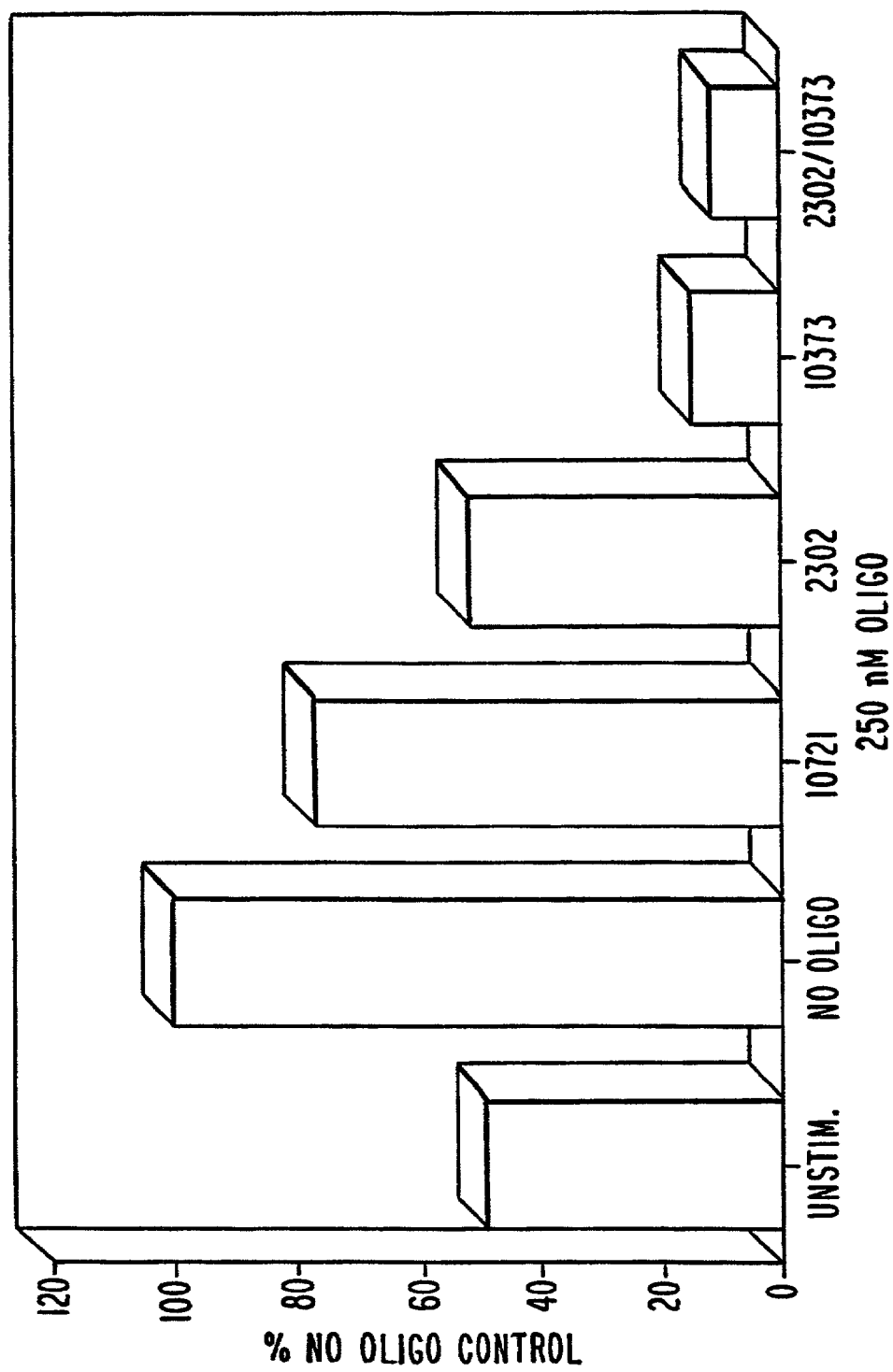
FIG. 7 is a bar graph showing the effect of the indicated oligonucleotides on T cell proliferation.

Results:

As shown in FIG. 7, mononuclear cells which were not cytokine-treated slightly induced T cell proliferation, presumably due to low levels of costimulatory molecules expressed on the cells. However, when the cells were treated with cytokines and induced to differentiate to dendritic-like cells, expression of both ICAM-1 and B7-2 was strongly upregulated. This resulted in a strong T cell proliferative response which could be blocked with either anti-ICAM-1 (ISIS 2302) or anti-B7-2 (ISIS 10373) oligonucleotides prior to induction of the mononuclear cells. The control oligonucleotide (ISIS 10721) had an insignificant effect on T cell proliferation. A combination treatment with both the anti-ICAM-1 (ISIS 2302) and anti-B7-2 (ISIS 10373) oligonucleotides resulted in a further decrease in T cell response.

Example 9

Modulation of Murine B7 Genes by Oligonucleotides

Oligonucleotides (see Table 4) capable of inhibiting expression of murine B7-2 transiently expressed in COS-7 cells were identified in the following manner. A series of phosphorothioate oligonucleotides complementary to murine B7-2 (mB7-2) cDNA were screened for their ability to reduce mB7-2 levels (measured by flow cytometry as in Example 2, except that a conjugated anti-mB7-2 antibody (i.e., anti-mCD86-PE, PharMingen, San Diego, Calif.) in COS-7 cells transfected with an mB7-2 cDNA clone. Anti-mB7-2 antibody may also be obtained from the hybridoma deposited at the ATCC under accession No. HB-253. Oligonucleotides (see Table 2) capable of modulating murine B7-1 expression are isolated in like fashion, except that a conjugated anti-mB7-1 antibody is used in conjunction with COS-7 cells transfected with an mB7-1 cDNA clone.

Figure 8:
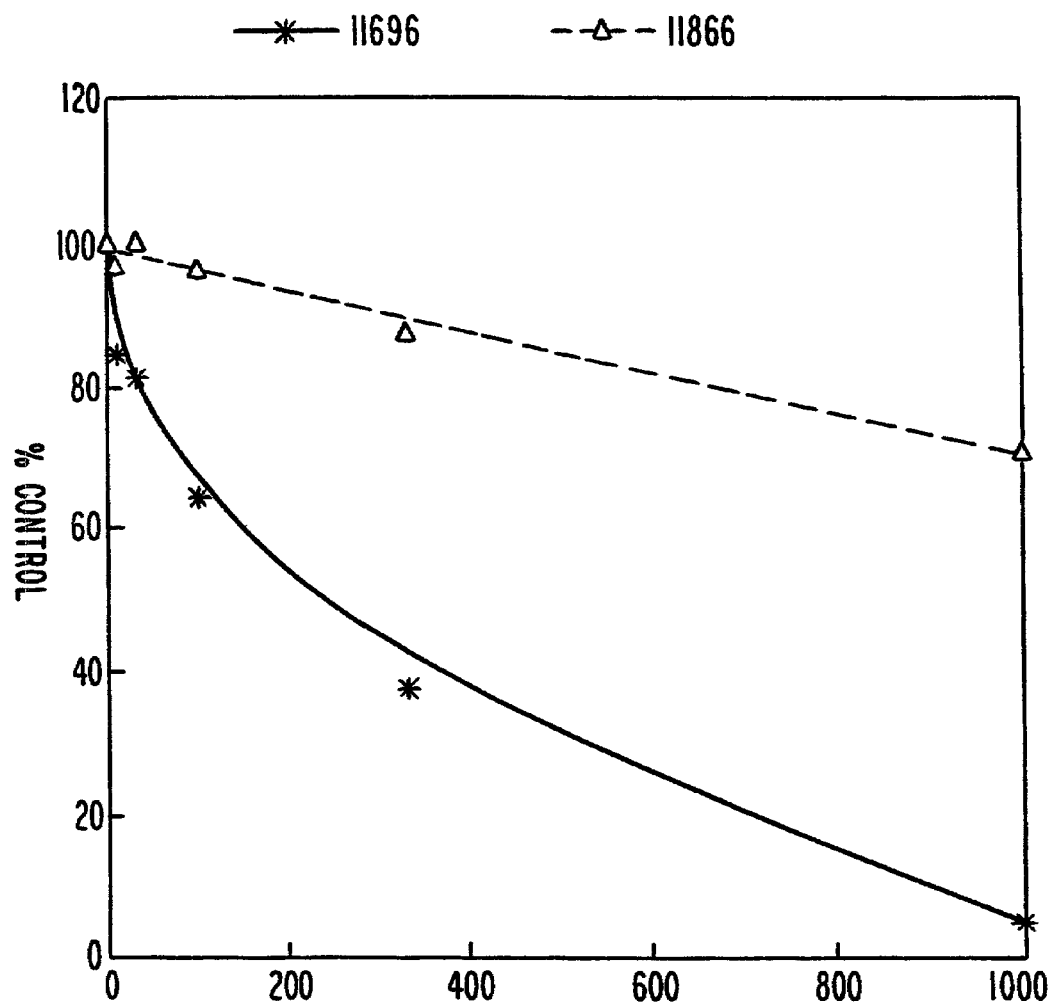
FIG. 8 is a dose-response curve showing the inhibitory effect of oligonucleotides on murine B7-2 protein expression in COS-7 cells. Solid line with asterisks, ISIS 11696; dashed line with triangles, ISIS 11866.

For murine B7-2, the most active oligonucleotide identified was ISIS 11696 (GGA-TTG-CCA-AGC-CCA-TGG-TG, SEQ ID NO: 18), which is complementary to position 96–115 of the cDNA, a site which includes the translation initiation (AUG) codon. FIG. 8 shows a dose-response curve for ISIS 11696 and a scrambled control, ISIS 11866 (CTA-AGT-AGT-GCT-AGC-CGG-GA, SEQ ID NO: 19). ISIS 11696 inhibited cell surface expression of B7-2 in COS-7 cells with an $IC_{50}$ in the range of 200–300 nM, while ISIS 11866 exhibited less than 20% inhibition at the highest concentration tested (1000 nM).

In order to further evaluate the murine B7-2 antisense oligonucleotides, the IC-21 cell line was used. IC-21 monocyte/macrophage cell line expresses both B7-1 and murine B7-2 (mB7-2) constitutively. A 2-fold induction of expression can be achieved by incubating the cells in the presence of lipopolysaccharide (LPS; GIBCO-BRL, Gaithersburg, Md.) (Hathcock et al., Science, 1993, 262, 905).

IC-21 cells (ATCC; accession No. TIB 186) were seeded at 80% confluency in 12-well plates in DMEM media with 10% FCS. The cells were allowed to adhere to the plate overnight. The following day, the medium was removed and the cells were washed with PBS. Then 500 µL of Opti-MEM™ (GIBCO-BRL, Gaithersburg, Md.) supplemented with 15 µg/mL of Lipofectin™ (GIBCO-BRL, Gaithersburg, Md.) was added to each well. Oligonucleotides were then added directly to the medium at the indicated concentrations. After incubation for 4 hours, the cells were washed with PBS and incubated overnight in culture medium supplemented with 15 µg/mL of LPS. The following day, cells were harvested by scraping, then analyzed for cell surface expression by flow cytometry.

Figure 9:
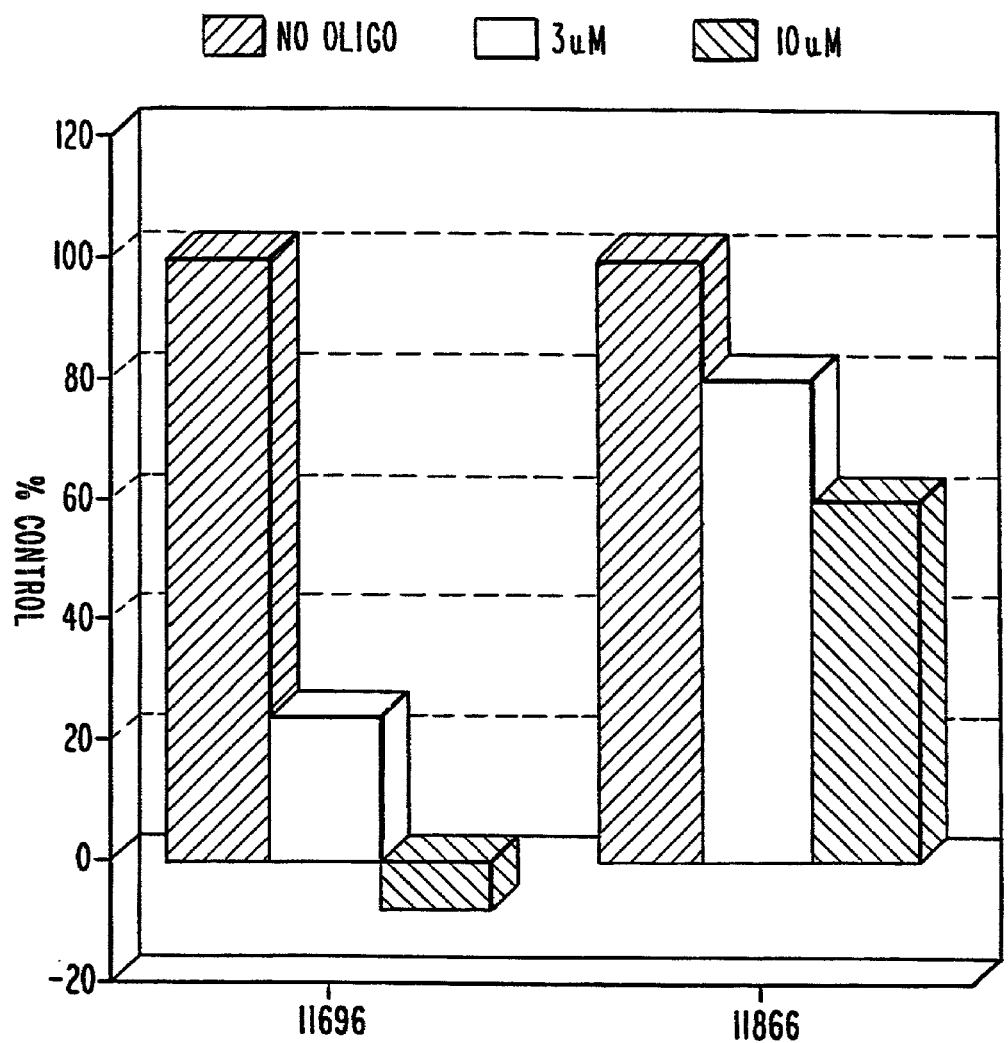
FIG. 9 is a bar graph showing the effect of oligonucleotides ISIS 11696 and ISIS 11866 on cell surface expression of murine B7-2 protein in IC-21 cells. Left (black) bars, no oligonucleotide; middle bars, 3 μM indicated oligonucleotide; right bars, 10 μM indicated oligonucleotide.
Figure 10:
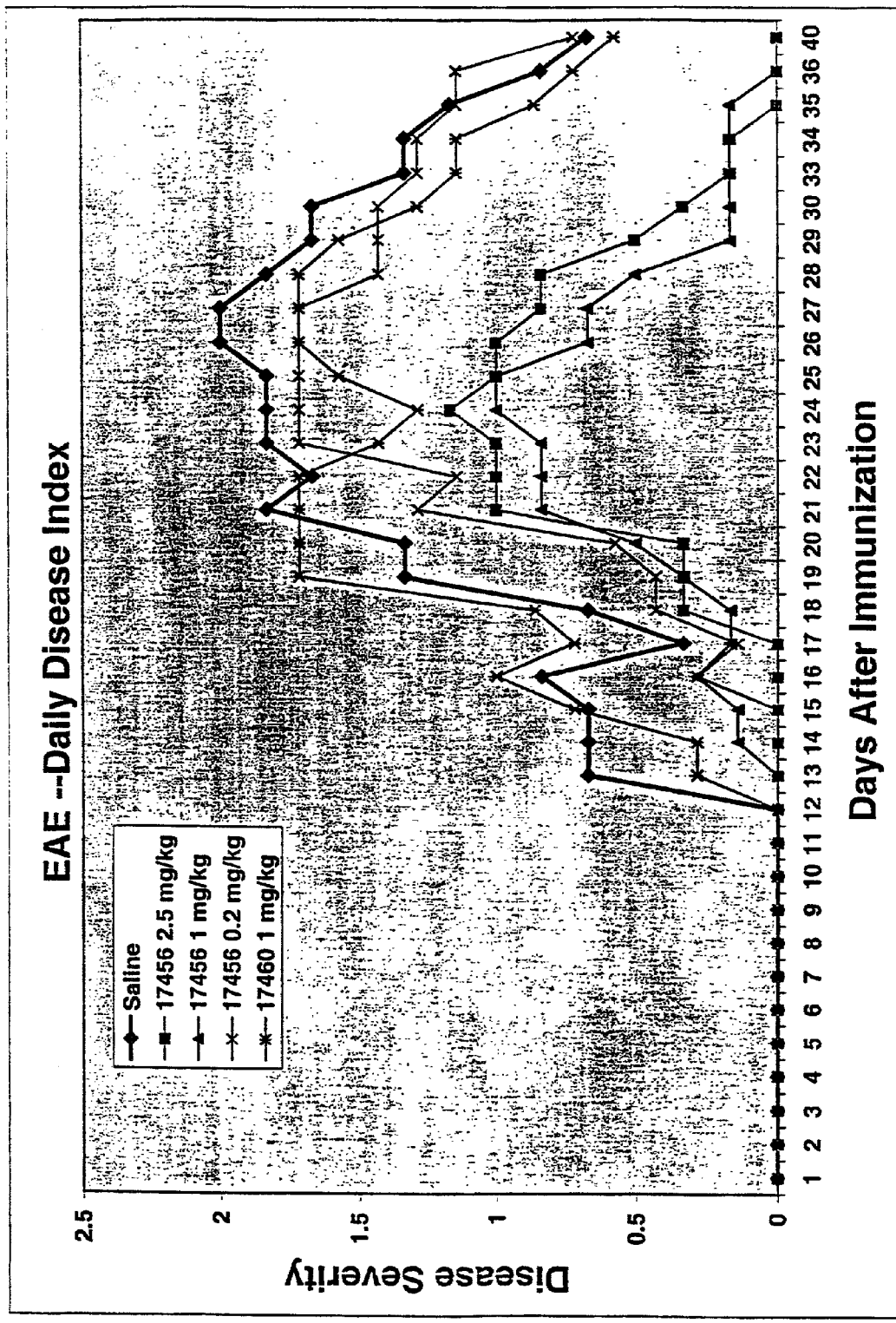
FIG. 10 is a graph showing the effect of ISIS 17456 on severity of EAE at various doses.

ISIS 11696 and ISIS 11866 were administered to IC-21 cells in the presence of Lipofectin™ (GIBCO-BRL, Gaithersburg, Md.). The results are shown in FIG. 9. At a concentration of 10 uM, ISIS 11696 inhibited mB7-2 expression completely (and decreased mB7-2 levels below the constitutive level of expression), while the scrambled control oligonucleotide, ISIS 11866, produced only a 40% reduction in the level of induced expression. At a concentration of 3 uM, levels of induced expression were greatly reduced by ISIS 11696, while ISIS 11866 had little effect.

Modified oligonucleotides, comprising 2' substitutions (e.g., 2' methoxy, 2' methoxyethoxy) and targeted to alternative transcripts of murine B7-1 (ISIS 12914, 12915, 13498, 13499) or murine B7-2 (ISIS 13100, 13100 and 13102) were prepared. These oligonucleotides are tested for their ability to modulate murine B7 essentially according to the above methods using IC-21 cells or COS-7 transfected with a cDNA clone corresponding to the appropriate alternatively spliced B7 transcript.

Example 10

Modulation of Allograft Rejection by Oligonucleotides

A murine model for evaluating compounds for their ability to inhibit heart allograft rejection has been previously described (Stepkowski et al., *J. Immunol.*, 1994, 153, 5336). This model was used to evaluate the immunosuppressive capacity of antisense oligonucleotides to B7 proteins alone or in combination with antisense oligonucleotides to intercellular adhesion molecule-1 (ICAM-1).

Methods:

Heart allograft rejection studies and oligonucleotide treatments of BALB/c mice were performed essentially as previously described (Stepkowski et al., *J. Immunol.*, 1994, 153, 5336). Antisense oligonucleotides used included ISIS 11696, ISIS 3082 (targeted to ICAM-1) and ISIS 1082 (a control oligonucleotide targeted to the herpes virus UL-13 gene sequence). Dosages used were 1, 2, 2.5, 5 or 10 mg/kg of individual oligonucleotide (as indicated below); when combinations of oligonucleotides were administered, each oligonucleotide was given at a dosage of 1, 5 or 10 mg/kg (total oligonucleotide dosages of 2, 10 and 20 mg/kg, respectively). The survival times of the transplanted hearts and their hosts were monitored and recorded.

Results:

The mean survival time for untreated mice was 8.2±0.8 days (7,8,8,8,9,9 days). Treatment of the mice for 7 days with ISIS 1082 (SEQ ID NO: 125, unrelated control oligonucleotide) slightly reduced the mean survival times to 7.1±0.7 days (5 mg/kg/day; 6,7,7,7,8,8) or 7.0±0.8 days(10 mg/kg/day; 6,7,7,8). Treatment of the mice for seven days with the murine B7-2 oligonucleotide ISIS 11696 (SEQ ID NO: 108) increased the mean survival time to 9.3 days at two doses (2 mg/kg/day, 9.3±0.6 days, 9,9,10; 10 mg/kg/day, 9.3±1.3 days, 8,9,9,11). Treatment of mice for seven days with an ICAM-1 oligonucleotide, ISIS 3082, also increased the mean survival of the mice over several doses. Specifically, at 1 mg/kg/day, the mean survival time (MSD) was 11.0±0.0 (11,11,11); at 2.5 mg/kg/day, the MSD was 12.0±2.7 (10,12,13,16); at 5 mg/kg/day, the MSD was 14.1±2.7 (10,12,12,13,16,16,17,17); and, at 10 mg/kg/day, the MSD was 15.3±5.8 (12,12,13,24). Some synergistic effect was seen when the mice were treated for seven days with 1 mg/kg/day each of ISIS 3082 and 11696: the MSD was 13.8±1.0 (13,13,14,15).

Example 11

Detection of Nucleic Acids Encoding B7 Proteins

Oligonucleotides are radiolabeled after synthesis by $^{32}$P-labeling at the 5' end with polynucleotide kinase. Sambrook et al., "Molecular Cloning. A Laboratory Manual," Cold Spring Harbor Laboratory Press, 1989, Volume 2, pg. 11.31. Radiolabeled oligonucleotide capable of hybridizing to a nucleic acid encoding a B7 protein is contacted with a tissue or cell sample suspected of B7 protein expression under conditions in which specific hybridization can occur, and the sample is washed to remove unbound oligonucleotide. A similar control is maintained wherein the radiolabeled oligonucleotide is contacted with a normal tissue or cell sample under conditions that allow specific hybridization, and the sample is washed to remove unbound oligonucleotide. Radioactivity remaining in the samples indicates bound oligonucleotide and is quantitated using a scintillation counter or other routine means. A greater amount of radioactivity remaining in the samples, as compared to control tissues or cells, indicates increased expression of a B7 gene, whereas a lesser amount of radioactivity in the samples relative to the controls indicates decreased expression of a B7 gene.

Radiolabeled oligonucleotides of the invention are also useful in autoradiography. A section of tissues suspected of expressing a B7 gene is treated with radiolabeled oligonucleotide and washed as described above, then exposed to photographic emulsion according to standard autoradiography procedures. A control of a normal tissue section is also maintained. The emulsion, when developed, yields an image of silver grains over the regions expressing a B7 gene, which is quantitated. The extent of B7 expression is determined by comparison of the silver grains observed with control and test samples.

Analogous assays for fluorescent detection of expression of a B7 gene use oligonucleotides of the invention which are labeled with fluorescein or other fluorescent tags. Labeled oligonucleotides are synthesized on an automated DNA synthesizer (Applied Biosystems, Foster City, Calif.) using standard phosphoramidite chemistry. b-Cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described above for radiolabeled oligonucleotides except that, instead of a scintillation counter, a fluorescence microscope is used to detect the fluorescence. A greater amount of fluorescence in the samples, as compared to control tissues or cells, indicates increased expression of a B7 gene, whereas a lesser amount of fluorescence in the samples relative to the controls indicates decreased expression of a B7 gene.

Example 12

Chimeric (Deoxy Gapped) Human B7-1 Antisense Oligonucleotides

Additional oligonucleotides targeting human B7-1 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 6.

Oligonucleotides were screened as described in Example 4. Results are shown in Table 7.

Oligonucleotides 22315 (SEQ ID NO: 128), 22316 (SEQ ID NO: 26), 22317 (SEQ ID NO: 129), 22320 (SEQ ID NO: 132), 22324 (SEQ ID NO: 135), 22325 (SEQ ID NO: 136), 22334 (SEQ ID NO: 145), 22335 (SEQ ID NO: 146), 22337 (SEQ ID NO: 148), and 22338 (SEQ ID NO: 36) resulted in 50% or greater inhibition of B7-1 mRNA in this assay.

TABLE 6

Nucleotide Sequences of Human B7-1 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 22313 | AGACTCCACTTCTGAGATGT | 126 | 0048–0067 | 5'-UTR |
| 22314 | TGAAGAAAAATTCCACTTTT | 127 | 0094–0113 | 5'-UTR |
| 22315 | TTTAGTTTCACAGCTTGCTG | 128 | 0112–0129 | 5'-UTR |
| 22316 | GCTCACGTAGAAGACCCTCC | 26 | 0193–0212 | 5'-UTR |
| 22317 | TCCCAGGTGCAAAACAGGCA | 129 | 0233–0252 | 5'-UTR |
| 22318 | GTGAAAGCCAACAATTTGGA | 130 | 0274–0293 | 5'-UTR |
| 22319 | CATGGCTTCAGATGCTTAGG | 131 | 0301–0320 | AUG |
| 22320 | TTGAGGTATGGACACTTGGA | 132 | 0351–0370 | coding |
| 22321 | GACCAGCCAGCACCAAGAGC | 31 | 0380–0399 | coding |
| 22322 | GCGTTGCCACTTCTTTCACT | 133 | 0440–0459 | coding |
| 22323 | TTTTGCCAGTAGATGCGAGT | 134 | 0501–0520 | coding |
| 22324 | GGCCATATATTCATGTCCCC | 135 | 0552–0571 | coding |
| 22325 | GCCAGGATCACAATGGAGAG | 136 | 0612–0631 | coding |
| 22326 | GTATGTGCCCTCGTCAGATG | 137 | 0640–0659 | coding |
| 22327 | TTCAGCCAGGTGTTCCCGCT | 138 | 0697–0716 | coding |
| 22328 | GGAAGTCAGCTTTGACTGAT | 139 | 0725–0744 | coding |
| 22329 | CCTCCAGAGGTTGAGCAAAT | 140 | 0798–0817 | coding |
| 22330 | CCAACCAGGAGAGGTGAGGC | 141 | 0827–0846 | coding |
| 22331 | GAAGCTGTGGTTGGTTGTCA | 142 | 0940–0959 | coding |
| 22332 | TTGAAGGTCTGATTCACTCT | 143 | 0987–1006 | coding |
| 22333 | AAGGTAATGGCCCAGGATGG | 144 | 1050–1069 | coding |
| 22334 | AAGCAGTAGGTCAGGCAGCA | 145 | 1098–1117 | coding |
| 22335 | CCTTGCTTCTGCGGACACTG | 146 | 1185–1204 | 3'-UTR |
| 22336 | AGCCCCTTGCTTCTGCGGAC | 147 | 1189–1208 | 3'-UTR |
| 22337 | TGACGGAGGCTACCTTCAGA | 148 | 1216–1235 | 3'-UTR |
| 22338 | GCCTCATGATCCCCACGATC | 36 | 1254–1273 | 3'-UTR |
| 22339 | GTAAAACAGCTTAAATTTGT | 149 | 1286–1305 | 3'-UTR |
| 22340 | AGAAGAGGTTACATTAAGCA | 150 | 1398–1417 | 3'-UTR |
| 22341 | AGATAATGAATTGGCTGACA | 151 | 1454–1473 | 3'-UTR |
| 24733 | GCGTCATCATCCGCACCATC | 152 | | control |
| 24734 | CGTTGCTTGTGCCGACAGTG | 153 | | control |
| 24735 | GCTCACGAAGAACACCTTCC | 154 | | control |

[1]Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2]Co-ordinates from Genbank Accession No. M27533, locus name "HUMIGB7".

TABLE 7

Inhibition of Human B7-1 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100% | — |
| 13805 | 30 | AUG | 46% | 54% |
| 13812 | 36 | 3'-UTR | 22% | 78% |
| 22313 | 126 | 5'-UTR | 75% | 25% |
| 22314 | 127 | 5'-UTR | 69% | 31% |
| 22315 | 128 | 5'-UTR | 49% | 51% |
| 22316 | 26 | 5'-UTR | 42% | 58% |
| 22317 | 129 | 5'-UTR | 43% | 57% |
| 22318 | 130 | 5'-UTR | 63% | 37% |
| 22319 | 131 | AUG | 68% | 32% |
| 22320 | 132 | coding | 45% | 55% |
| 22321 | 31 | coding | 57% | 43% |
| 22324 | 135 | coding | 46% | 54% |
| 22325 | 136 | coding | 46% | 54% |
| 22326 | 137 | coding | 62% | 38% |
| 22328 | 139 | coding | 64% | 36% |
| 22329 | 140 | coding | 59% | 41% |
| 22330 | 141 | coding | 54% | 46% |
| 22331 | 142 | coding | 62% | 38% |
| 22332 | 143 | coding | 67% | 33% |
| 22333 | 144 | coding | 73% | 27% |
| 22334 | 145 | coding | 43% | 57% |
| 22335 | 146 | 3'-UTR | 43% | 57% |
| 22336 | 147 | 3'-UTR | 55% | 45% |

TABLE 7-continued

Inhibition of Human B7-1 mRNA Expression by Chimeric (deoxy gapped) Phosphorothioate Oligodeoynucleotides

| ISIS No: | SEQ ID NO: | GENE TARGET REGION | % mRNA EXPRESSION | % mRNA INHIBITION |
|---|---|---|---|---|
| 22337 | 148 | 3'-UTR | 42% | 58% |
| 22338 | 36 | 3'-UTR | 40% | 60% |
| 22339 | 149 | 3'-UTR | 69% | 31% |
| 22340 | 150 | 3'-UTR | 71% | 29% |
| 22341 | 151 | 3'-UTR | 59% | 41% |

Dose response experiments were performed on several of the more active oligonucleotides. The oligonucleotides were screened as described in Example 4 except that the concentration of oligonucleotide was varied as shown in Table 8. Mismatch control oligonucleotides were included. Results are shown in Table 8.

All antisense oligonucleotides tested showed a dose response effect with inhibition of mRNA approximately 60% or greater.

TABLE 8

Dose Response of COS-7 Cells to B7-1 Chimeric (deoxy gapped) Antisense Oligonucleotides

| ISIS # | SEQ ID NO: | ASO Gene Target | Dose | % mRNA Expression | % mRNA Inhibition |
|---|---|---|---|---|---|
| basal | — | — | — | 100% | — |
| 22316 | 26 | 5'-UTR | 10 nM | 99% | 1% |
| " | " | " | 30 nM | 73% | 27% |
| " | " | " | 100 nM | 58% | 42% |
| " | " | " | 300 nM | 33% | 67% |
| 24735 | 154 | control | 10 nM | 100% | — |
| " | " | " | 30 nM | 95% | 5% |
| " | " | " | 100 nM | 81% | 19% |
| " | " | " | 300 nM | 75% | 25% |
| 22335 | 146 | 3'-UTR | 10 nM | 81% | 19% |
| " | " | " | 30 nM | 63% | 37% |
| " | " | " | 100 nM | 43% | 57% |
| " | " | " | 300 nM | 35% | 65% |

TABLE 8-continued

Dose Response of COS-7 Cells to B7-1 Chimeric (deoxy gapped) Antisense Oligonucleotides

| ISIS # | SEQ ID NO: | ASO Gene Target | Dose | % mRNA Expression | % mRNA Inhibition |
|---|---|---|---|---|---|
| 24734 | 153 | control | 10 nM | 94% | 6% |
| " | " | " | 30 nM | 96% | 4% |
| " | " | " | 100 nM | 94% | 6% |
| " | " | " | 300 nM | 84% | 16% |
| 22338 | 36 | 3'-UTR | 10 nM | 68% | 32% |
| " | " | " | 30 nM | 60% | 40% |
| " | " | " | 100 nM | 53% | 47% |
| " | " | " | 300 nM | 41% | 59% |
| 24733 | 152 | control | 10 nM | 90% | 10% |
| " | " | " | 30 nM | 91% | 9% |
| " | " | " | 100 nM | 90% | 10% |
| " | " | " | 300 nM | 80% | 20% |

Example 13

Chimeric (Deoxy Gapped) Mouse B7-1 Antisense Oligonucleotides

Additional oligonucleotides targeting mouse B7-1 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 9.

Oligonucleotides were screened as described in Example 4. Results are shown in Table 10.

Oligonucleotides 18105 (SEQ ID NO: 156), 18106 (SEQ ID NO: 157), 18109 (SEQ ID NO: 160), 18110 (SEQ ID NO: 161), 18111 (SEQ ID NO: 162), 18112 (SEQ ID NO: 163), 18113 (SEQ ID NO: 164), 18114 (SEQ ID NO: 165), 18115 (SEQ ID NO: 166), 18117 (SEQ ID NO: 168), 18118 (SEQ ID NO: 169), 18119 (SEQ ID NO: 170), 18120 (SEQ ID NO: 171), 18122 (SEQ ID NO: 173), and 18123 (SEQ ID NO: 174) resulted in greater than approximately 50% inhibition of B7-1 mRNA in this assay.

TABLE 9

Nucleotide Sequences of Mouse B7-1 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 18104 | AGAGAAACTAGTAAGAGTCT | 155 | 0018–0037 | 5'-UTR |
| 18105 | TGGCATCCACCCGGCAGATG | 156 | 0110–0129 | 5'-UTR |
| 18106 | TCGAGAAACAGAGATGTAGA | 157 | 0144–0163 | 5'-UTR |
| 18107 | TGGAGCTTAGGCACCTCCTA | 158 | 0176–0195 | 5'-UTR |
| 18108 | TGGGGAAAGCCAGGAATCTA | 159 | 0203–0222 | 5'-UTR |
| 18109 | CAGCACAAAGAGAAGAATGA | 160 | 0310–0329 | coding |
| 18110 | ATGAGGAGAGTTGTAACGGC | 161 | 0409–0428 | coding |
| 18111 | AAGTCCGGTTCTTATACTCG | 162 | 0515–0534 | coding |
| 18112 | GCAGGTAATCCTTTTAGTGT | 163 | 0724–0743 | coding |
| 18113 | GTGAAGTCCTCTGACACGTG | 164 | 0927–0946 | coding |
| 18114 | CGAATCCTGCCCCAAAGAGC | 165 | 0995–1014 | coding |
| 18115 | ACTGCGCCGAATCCTGCCCC | 166 | 1002–1021 | coding |
| 18116 | TTGATGATGACAACGATGAC | 167 | 1035–1054 | coding |
| 18117 | CTGTTGTTTGTTTCTCTGCT | 168 | 1098–1117 | coding |
| 18118 | TGTTCAGCTAATGCTTCTTC | 169 | 1134–1153 | coding |
| 18119 | GTTAACTCTATCTTGTGTCA | 170 | 1263–1282 | 3'-UTR |
| 18120 | TCCACTTCAGTCATCAAGCA | 171 | 1355–1374 | 3'-UTR |

TABLE 9-continued

Nucleotide Sequences of Mouse B7-1 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 18121 | TGCTCAATACTCTCTTTTTA | 172 | 1680–1699 | 3'-UTR |
| 18122 | AGGCCCAGCAAACTTGCCCG | 173 | 1330–1349 | 3'-UTR |
| 18123 | AACGGCAAGGCAGCAATACC | 174 | 0395–0414 | coding |

[1]Emboldened residues are 2'-methoxyethoxy residues (others are 2'-deoxy-). All 2'-methoxy-ethyl cytosines and 2'-deoxy cytosines residues are 5-methyl-cytosines; all linkages are phosphorothioate linkages.
[2]Co-ordinates from Genbank Accession No. X60958, locus name "MMB7BLAA".

TABLE 10

Inhibition of Mouse B7-1 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100.0% | — |
| 18104 | 155 | 5'-UTR | 60.0% | 40.0% |
| 18105 | 156 | 5'-UTR | 32.0% | 68.0% |
| 18106 | 157 | 5'-UTR | 51.0% | 49.0% |
| 18107 | 158 | 5'-UTR | 58.0% | 42.0% |
| 18108 | 159 | 5'-UTR | 82.0% | 18.0% |
| 18109 | 160 | coding | 45.5% | 54.5% |
| 18110 | 161 | coding | 21.0% | 79.0% |
| 18111 | 162 | coding | 38.0% | 62.0% |
| 18112 | 163 | coding | 42.0% | 58.0% |
| 18113 | 164 | coding | 24.6% | 75.4% |
| 18114 | 165 | coding | 25.6% | 74.4% |
| 18115 | 166 | coding | 33.5% | 66.5% |
| 18116 | 167 | coding | 65.6% | 34.4% |
| 18117 | 168 | coding | 46.7% | 53.3% |
| 18118 | 169 | coding | 31.7% | 68.3% |
| 18119 | 170 | 3'-UTR | 24.0% | 76.0% |
| 18120 | 171 | 3'-UTR | 26.7% | 73.3% |
| 18121 | 172 | 3'-UTR | 114.0% | — |
| 18122 | 173 | 3'-UTR | 42.0% | 58.0% |
| 18123 | 174 | coding | 42.0% | 58.0% |

Example 14

Chimeric (Deoxy Gapped) Human B7-2 Antisense Oligonucleotides

Additional oligonucleotides targeting human B7-2 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 11.

Oligonucleotides were screened as described in Example 4. Results are shown in Table 12.

Oligonucleotides 22284 (SEQ ID NO: 16), 22286 (SEQ ID NO: 176), 22287 (SEQ ID NO: 177), 22288 (SEQ ID NO: 178), 22289 (SEQ ID NO: 179), 22290 (SEQ ID NO: 180), 22291 (SEQ ID NO: 181), 22292 (SEQ ID NO: 182), 22293 (SEQ ID NO: 183), 22294 (SEQ ID NO: 184), 22296 (SEQ ID NO: 186), 22299 (SEQ ID NO: 189), 22300 (SEQ ID NO: 190), 22301 (SEQ ID NO: 191), 22302 (SEQ ID NO: 192), 22303 (SEQ ID NO: 193), 22304 (SEQ ID NO: 194), 22306 (SEQ ID NO: 196), 22307 (SEQ ID NO: 197), 22308 (SEQ ID NO: 198), 22309 (SEQ ID NO: 199), 22310 (SEQ ID NO: 200), and 22311 (SEQ ID NO: 201) resulted in greater than 50% inhibition of B7-2 mRNA in this assay.

TABLE 11

Nucleotide Sequences of Human B7-2 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 22284 | TGCGAGCTCCCCGTACCTCC | 16 | 0011–0030 | 5'-UTR |
| 22285 | CAGAAGCAAGGTGGTAAGAA | 175 | 0049–0068 | 5'-UTR |
| 22286 | GCCTGTCCACTGTAGCTCCA | 176 | 0113–0132 | 5'-UTR |
| 22287 | AGAATGTTACTCAGTCCCAT | 177 | 0148–0167 | AUG |
| 22288 | TCAGAGGAGCAGCACCAGAG | 178 | 0189–0208 | coding |
| 22289 | TGGCATGGCAGGTCTGCAGT | 179 | 0232–0251 | coding |
| 22290 | AGCTCACTCAGGCTTTGGTT | 180 | 0268–0287 | coding |
| 22291 | TGCCTAAGTATACCTCATTC | 181 | 0324–0343 | coding |
| 22292 | CTGTCAAATTTCTCTTTGCC | 182 | 0340–0359 | coding |
| 22293 | CATATACTTGGAATGAACAC | 183 | 0359–0378 | coding |
| 22294 | GGTCCAACTGTCCGAATCAA | 184 | 0392–0411 | coding |
| 22295 | TGATCTGAAGATTGTGAAGT | 185 | 0417–0436 | coding |
| 22296 | AAGCCCTTGTCCTTGATCTG | 186 | 0430–0449 | coding |
| 22297 | TGTGATGGATGATACATTGA | 187 | 0453–0472 | coding |
| 22298 | TCAGGTTGACTGAAGTTAGC | 188 | 0529–0548 | coding |
| 22299 | GTGTATAGATGAGCAGGTCA | 189 | 0593–0612 | coding |
| 22300 | TCTGTGACATTATCTTGAGA | 190 | 0694–0713 | coding |

TABLE 11-continued

Nucleotide Sequences of Human B7-2 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 22301 | AAGATAAAAGCCGCGTCTTG | 191 | 0798–0817 | coding |
| 22302 | AGAAAACCATCACACATATA | 192 | 0900–0919 | coding |
| 22303 | AGAGTTGCGAGGCCGCTTCT | 193 | 0947–0968 | coding |
| 22304 | TCCCTCTCCATTGTGTTGGT | 194 | 0979–0998 | coding |
| 22305 | CATCAGATCTTTCAGGTATA | 195 | 1035–1054 | coding |
| 22306 | GGCTTTACTCTTTAATTAAA | 196 | 1115–1134 | stop |
| 22307 | GAAATCAAAAGGTTGCCCA | 197 | 1178–1197 | 3'-UTR |
| 22308 | GGAGTCCTGGAGCCCCCTTA | 198 | 1231–1250 | 3'-UTR |
| 22309 | TTGGCATACGGAGCAGAGCT | 199 | 1281–1300 | 3'-UTR |
| 22310 | TGTGCTCTGAAGTGAAAAGA | 200 | 1327–1346 | 3'-UTR |
| 22311 | GGCTTGGCCCATAAGTGTGC | 201 | 1342–1361 | 3'-UTR |
| 22312 | CCTAAATTTTATTTCCAGGT | 202 | 1379–1398 | 3'-UTR |
| 24736 | GCTCCAAGTGTCCCAATGAA | 203 | control | |
| 24737 | AGTATGTTTCTCACTCCGAT | 204 | control | |
| 24738 | TGCCAGCACCCGGTACGTCC | 205 | control | |

[1]Emboldened residues are 2'-methoxyethoxy residues (others are 2'-deoxy-). All 2'-methoxy-ethyl cytosines and 2'-deoxy cytosines residues are 5-methyl-cytosines; all linkages are phosphorothioate linkages.
[2]Co-ordinates from Genbank Accession No. U04343 locus name "HSU04343".

TABLE 12

Inhibition of Human B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100% | 0% |
| 10373 | 16 | 5'-UTR | 24% | 76% |
| 22284 | 16 | 5'-UTR | 30% | 70% |
| 22285 | 175 | 5'-UTR | 74% | 26% |
| 22286 | 176 | 5'-UTR | 39% | 61% |
| 22287 | 177 | AUG | 27% | 73% |
| 22288 | 178 | coding | 38% | 62% |
| 22289 | 179 | coding | 41% | 59% |
| 22290 | 180 | coding | 42% | 58% |
| 22291 | 181 | coding | 41% | 59% |
| 22292 | 182 | coding | 39% | 61% |
| 22293 | 183 | coding | 43% | 57% |
| 22294 | 184 | coding | 21% | 79% |
| 22295 | 185 | coding | 66% | 34% |
| 22296 | 186 | coding | 42% | 58% |
| 22297 | 187 | coding | 54% | 46% |
| 22298 | 188 | coding | 53% | 47% |
| 22299 | 189 | coding | 46% | 54% |
| 22300 | 190 | coding | 39% | 61% |
| 22301 | 191 | coding | 51% | 49% |
| 22302 | 192 | coding | 41% | 59% |
| 22303 | 193 | coding | 46% | 54% |
| 22304 | 194 | coding | 41% | 59% |
| 22305 | 195 | coding | 57% | 43% |
| 22306 | 196 | stop | 44% | 56% |
| 22307 | 197 | 3'-UTR | 45% | 55% |
| 22308 | 198 | 3'-UTR | 40% | 60% |
| 22309 | 199 | 3'-UTR | 42% | 58% |
| 22310 | 200 | 3'-UTR | 41% | 59% |
| 22311 | 201 | 3'-UTR | 49% | 51% |
| 22312 | 202 | 3'-UTR | 83% | 17% |

Dose response experiments were performed on several of the more active oligonucleotides. The oligonucleotides were screened as described in Example 4 except that the concentration of oligonucleotide was varied as shown in Table 13. Mismatch control oligonucleotides were included. Results are shown in Table 13.

All antisense oligonucleotides tested showed a dose response effect with maximum inhibition of mRNA approximately 50% or greater.

TABLE 13

Dose Response of COS-7 Cells to B7-2 Chimeric (deoxy gapped) Antisense Oligonucleotides

| ISIS # | SEQ ID NO: | ASO Gene Target | Dose | % mRNA Expression | % mRNA Inhibition |
|---|---|---|---|---|---|
| basal | — | — | — | 100% | — |
| 22284 | 16 | 5'-UTR | 10 nM | 92% | 8% |
| " | " | " | 30 nM | 72% | 28% |
| " | " | " | 100 nM | 59% | 41% |
| " | " | " | 300 nM | 48% | 52% |
| 24738 | 205 | control | 10 nM | 81% | 19% |
| " | " | " | 30 nM | 92% | 8% |
| " | " | " | 100 nM | 101% | — |
| " | " | " | 300 nM | 124% | — |
| 22287 | 177 | AUG | 10 nM | 93% | 7% |
| " | " | " | 30 nM | 79% | 21% |
| " | " | " | 100 nM | 66% | 34% |
| " | " | " | 300 nM | 45% | 55% |
| 24737 | 204 | control | 10 nM | 85% | 15% |
| " | " | " | 30 nM | 95% | 5% |
| " | " | " | 100 nM | 87% | 13% |
| " | " | " | 300 nM | 99% | 1% |
| 22294 | 184 | coding | 10 nM | 93% | 7% |
| " | " | " | 30 nM | 95% | 5% |
| " | " | " | 100 nM | 58% | 42% |
| " | " | " | 300 nM | 45% | 55% |
| 24736 | 203 | control | 10 nM | 102% | — |
| " | " | " | 30 nM | 101% | — |
| " | " | " | 100 nM | 100% | — |
| " | " | " | 300 nM | 107% | — |

Example 15

Chimeric (Deoxy Gapped) Mouse B7-2 Antisense Oligonucleotides

Additional oligonucleotides targeting mouse B7-2 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 14.

Oligonucleotides were screened as described in Example 4. Results are shown in Table 15.

Oligonucleotides 18084 (SEQ ID NO: 206), 18085 (SEQ ID NO: 207), 18086 (SEQ ID NO: 208), 18087 (SEQ ID NO: 209), 18089 (SEQ ID NO: 211), 18090 (SEQ ID NO: 212), 18091 (SEQ ID NO: 213), 18093 (SEQ ID NO: 215), 18095 (SEQ ID NO: 217), 18096 (SEQ ID NO: 218), 18097 (SEQ ID NO: 219), 18098 (SEQ ID NO: 108), 18102 (SEQ ID NO: 223), and 18103 (SEQ ID NO: 224) resulted in 50% or greater inhibition of B7-2 mRNA expression in this assay.

TABLE 14

Nucleotide Sequences of Mouse B7-2 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 18084 | GCTGCCTACAGGAGCCACTC | 206 | 0003–0022 | 5'-UTR |
| 18085 | TCAAGTCCGTGCTGCCTACA | 207 | 0013–0032 | 5'-UTR |
| 18086 | GTCTACAGGAGTCTGGTTGT | 208 | 0033–0052 | 5'-UTR |
| 18087 | AGCTTGCGTCTCCACGGAAA | 209 | 0152–0171 | coding |
| 18088 | TCACACTATCAAGTTTCTCT | 210 | 0297–0316 | coding |
| 18089 | GTCAAAGCTCGTGCGGCCCA | 211 | 0329–0348 | coding |
| 18090 | GTGAAGTCGTAGAGTCCAGT | 212 | 0356–0375 | coding |
| 18091 | GTGACCTTGCTTAGACGTGC | 213 | 0551–0570 | coding |
| 18092 | CATCTTCTTAGGTTTCGGGT | 214 | 0569–0588 | coding |
| 18093 | GGCTGTTGGAGATACTGAAC | 215 | 0663–0682 | coding |
| 18094 | GGGAATGAAAGAGAGAGGCT | 216 | 0679–0698 | coding |
| 18095 | ACATACAATGATGAGCAGCA | 217 | 0854–0873 | coding |
| 18096 | GTCTCTCTGTCAGCGTTACT | 218 | 0934–0953 | coding |
| 18097 | TGCCAAGCCCATGGTGCATC | 219 | 0092–0111 | AUG |
| 18098 | GGATTGCCAAGCCCATGGTG | 108 | 0096–0115 | AUG |
| 18099 | GCAATTTGGGGTTCAAGTTC | 220 | 0967–0986 | coding |
| 18100 | CAATCAGCTGAGAACATTTT | 221 | 1087–1106 | 3'-UTR |
| 18101 | TTTTGTATAAAACAATCATA | 222 | 0403–0422 | coding |
| 18102 | CCTTCACTCTGCATTTGGTT | 223 | 0995–1014 | stop |
| 18103 | TGCATGTTATCACCATACTC | 224 | 0616–0635 | coding |

[1]Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2]Co-ordinates from Genbank Accession No. S70108 locus name "S70108".

TABLE 15

Inhibition of Mouse B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100.0% | 0.0% |
| 18084 | 206 | 5'-UTR | 36.4% | 63.6% |
| 18085 | 207 | 5'-UTR | 35.0% | 65.0% |
| 18086 | 208 | 5'-UTR | 40.1% | 59.9% |
| 18087 | 209 | coding | 42.1% | 57.9% |
| 18088 | 210 | coding | 52.3% | 47.7% |
| 18089 | 211 | coding | 20.9% | 79.1% |
| 18090 | 212 | coding | 36.6% | 63.4% |
| 18091 | 213 | coding | 37.1% | 62.9% |
| 18092 | 214 | coding | 58.9% | 41.1% |
| 18093 | 215 | coding | 32.7% | 67.3% |
| 18094 | 216 | coding | 63.8% | 36.2% |
| 18095 | 217 | coding | 34.3% | 65.7% |
| 18096 | 218 | coding | 32.3% | 67.7% |
| 18097 | 219 | AUG | 24.5% | 75.5% |
| 18098 | 108 | AUG | 32.2% | 67.8% |
| 18099 | 220 | coding | 66.8% | 33.2% |
| 18100 | 221 | 3'-UTR | 67.2% | 32.8% |
| 18101 | 222 | coding | 88.9% | 11.1% |
| 18102 | 223 | stop | 33.8% | 66.2% |
| 18103 | 224 | coding | 30.2% | 69.8% |

Example 16

Effect of B7 Antisense Oligonucleotides on Cell Surface Expression

B7 antisense oligonucleotides were tested for their effect on cell surface expression of both B7-1 and B7-2. Cell surface expression was measured as described in Example 2. Experiments were done for both human B7 and mouse B7. Results for human B7 are shown in Table 16. Results for mouse B7 are shown in Table 17.

In both species, B7-1 antisense oligonucleotides were able to specifically reduce the cell surface expression of B7-1. B7-2 antisense oligonucleotides were specific for the B7-2 family member. These oligonucleotides were also specific for their effect on B7-1 and B7-2 mRNA levels.

TABLE 16

Inhibition of Human B7 Cell Surface Expression by Chimeric (deoxy gapped) Phosphorothioate Oligodeoxynucleotides

| ISIS No: | SEQ ID NO: | GENE TARGET | % B7-1 EXPRESSION | % B7-2 EXPRESSION |
|---|---|---|---|---|
| basal | — | — | 100% | 0% |
| 22316 | 26 | B7-1 | 31% | 100% |
| 22317 | 129 | B7-1 | 28% | 91% |
| 22320 | 132 | B7-1 | 37% | 86% |
| 22324 | 135 | B7-1 | 37% | 91% |
| 22325 | 136 | B7-1 | 32% | 89% |
| 22334 | 145 | B7-1 | 28% | 92% |
| 22335 | 146 | B7-1 | 23% | 95% |
| 22337 | 148 | B7-1 | 48% | 101% |
| 22338 | 36 | B7-1 | 22% | 96% |
| 22284 | 16 | B7-2 | 88% | 32% |
| 22287 | 177 | B7-2 | 92% | 35% |
| 22294 | 184 | B7-2 | 77% | 28% |

TABLE 17

Inhibition of Mouse B7 Cell Surface Expression by Chimeric (deoxy gapped) Phosphorothioate Oligodeoxynucleotides

| ISIS No: | SEQ ID NO: | GENE TARGET REGION | % B7-1 EXPRESSION | % B7-2 EXPRESSION |
|---|---|---|---|---|
| basal | — | — | 100% | 0% |
| 18089 | 211 | B7-2 | 85% | 36% |
| 18097 | 219 | B7-2 | 87% | 28% |
| 18110 | 161 | B7-1 | 31% | 93% |
| 18113 | 164 | B7-1 | 25% | 91% |
| 18119 | 170 | B7-1 | 27% | 98% |

Dose response experiments were performed on several of the more active human B7-1 antisense oligonucleotides. The oligonucleotides were screened as described in Example 2 except that the concentration of oligonucleotide was varied as shown in Table 18. Results are shown in Table 18.

All antisense oligonucleotides tested showed a dose response effect with inhibition of cell surface expression approximately 60% or greater.

TABLE 18

Dose Response of COS-7 Cells to B7-1 Chimeric (deoxy gapped) Antisense Oligonucleotides

| ISIS # | SEQ ID NO: | ASO Gene Target | Dose | % Surface Expression | % Surface Inhibition |
|---|---|---|---|---|---|
| basal | — | — | — | 100% | — |
| 22316 | 26 | 5'-UTR | 10 nM | 74% | 26% |
| " | " | " | 30 nM | 74% | 26% |
| " | " | " | 100 nM | 47% | 53% |
| " | " | " | 300 nM | 34% | 66% |
| 22335 | 146 | 3'-UTR | 10 nM | 81% | 19% |
| " | " | " | 30 nM | 69% | 31% |
| " | " | " | 100 nM | 47% | 53% |
| " | " | " | 300 nM | 38% | 62% |

TABLE 18-continued

Dose Response of COS-7 Cells to B7-1 Chimeric (deoxy gapped) Antisense Oligonucleotides

| ISIS # | SEQ ID NO: | ASO Gene Target | Dose | % Surface Expression | % Surface Inhibition |
|---|---|---|---|---|---|
| 22338 | 36 | 3'-UTR | 10 nM | 78% | 22% |
| " | " | " | 30 nM | 65% | 35% |
| " | " | " | 100 nM | 50% | 50% |
| " | " | " | 300 nM | 40% | 60% |

Dose response experiments were performed on several of the more active human B7-2 antisense oligonucleotides. The oligonucleotides were screened as described in Example 2 except that the concentration of oligonucleotide was varied as shown in Table 19. Results are shown in Table 19.

All antisense oligonucleotides tested showed a dose response effect with maximum inhibition of cell surface expression 85% or greater.

TABLE 19

Dose Response of COS-7 Cells to B7-2 Chimeric (deoxy gapped) Antisense Oligonucleotides

| ISIS # | SEQ ID NO: | ASO Gene Target | Dose | % Surface Expression | % Surface Inhibition |
|---|---|---|---|---|---|
| basal | — | — | — | 100% | — |
| 22284 | 16 | 5'-UTR | 10 nM | 63% | 37% |
| " | " | " | 30 nM | 60% | 40% |
| " | " | " | 100 nM | 37% | 63% |
| " | " | " | 300 nM | 15% | 85% |
| 22287 | 177 | AUG | 10 nM | 93% | 7% |
| " | " | " | 30 nM | 60% | 40% |
| " | " | " | 100 nM | 32% | 68% |
| " | " | " | 300 nM | 15% | 85% |
| 22294 | 184 | coding | 10 nM | 89% | 11% |
| " | " | " | 30 nM | 62% | 38% |
| " | " | " | 100 nM | 29% | 71% |
| " | " | " | 300 nM | 12% | 88% |

Example 17

Effect of B7-1 Antisense Oligonucleotides in a Murine Model for Rheumatoid Arthritis Collagen-induced arthritis (CIA) was used as a murine model for arthritis (Mussener, A., et al., *Clin. Exp. Immunol.*, 1997, 107, 485–493). Female DBA/1LacJ mice (Jackson Laboratories, Bar Harbor, Me.) between the ages of 6 and 8 weeks were used to assess the activity of B7-1 antisense oligonucleotides.

On day 0, the mice were immunized at the base of the tail with 100 μg of bovine type II collagen which is emulsified in Complete Freund's Adjuvant (CPA). On day 7, a second booster dose of collagen was administered by the same route. On day 14, the mice were injected subcutaneously with 100 μg of LPS. Oligonucleotide was administered intraperitoneally daily (10 mg/kg bolus) starting on day −3 (three days before day 0) and continuing for the duration of the study. Oligonucleotide 17456 (SEQ ID NO. 173) is a fully phosphorothioated analog of 18122.

Weights were recorded weekly. Mice were inspected daily for the onset of CIA. Paw widths are rear ankle widths of affected and unaffected joints were measured three times a week using a constant tension caliper. Limbs were clinically evaluated and graded on a scale from 0–4 (with 4 being the highest).

Results are shown in Table 20. Treatment with B7-1 and B7-2 antisense oligonucleotides was able to reduce the incidence of the disease, but had modest effects on severity. The combination of 17456 (SEQ ID NO. 173) and 11696 (SEQ ID NO. 108) was able to significantly reduce the incidence of the disease and its severity.

TABLE 20

Effect of B7 antisense oligonucleotide on CIA

| ISIS # (s) | SEQ ID NO | Dose mg/kg | % Incidence | Peak day[1] | Severity[2] |
|---|---|---|---|---|---|
| control | — | — | 70% | 6.7 ± 2.9 | 3.2 ± 1.1 |
| 17456 (B7-1) | 173 | 10 | 50% | 12.1 ± 4.6 | 2.7 ± 1.3 |
| 11696 (B7-2) | 108 | 10 | 37.5% | 11.6 ± 4.5 | 3.4 ± 1.8 |
| 17456/11696 | | 10 | 30% | 1.0 ± 0.6 | 0.7 ± 0.4 |
| 18110 (B7-1) | 161 | 10 | 55.6% | 2.0 ± 0.8 | 2.0 ± 1.3 |
| 18089 (B7-2) | 211 | 10 | 44.4% | 6.8 ± 2.2 | 2.3 ± 1.3 |
| 18110/18089 | | 10 | 60% | 11.6 ± 0.7 | 4.5 ± 1.7 |

[1] Peak day is the day from onset of maximum swelling for each joint measure.
[2] Severity is the total clinical score divided by the total number of mice in the group.

Example 18

Effect of B7-1 Antisense Oligonucleotides in a Murine Model for Multiple Sclerosis Experimental autoimmune encephalomyelitis (EAE) is a commonly accepted murine model for multiple sclerosis (Myers, K. J., et al., *J. Neuroimmunol.*, 1992, 41, 1–8). SJL/H, PL/J, (SJLxPL/J)F1, (SJLxBalb/c)F1 and Balb/c female mice between the ages of 6 and 12 weeks are used to test the activity of a B7-1 antisense oligonucleotide.

The mice are immunized in the two rear foot pads and base of the tail with an emulsion consisting of encephalitogenic protein or peptide (according to Myers, K. J., et al., *J. of Immunol.*, 1993, 151, 2252–2260) in Complete Freund's Adjuvant supplemented with heat killed *Mycobacterium tuberculosis*. Two days later, the mice receive an intravenous injection of 500 ng Bordatella pertussis toxin and additional adjuvant.

Alternatively, the disease may also be induced by the adoptive transfer of T-cells. T-cells are obtained from the draining of the lymph nodes of mice immunized with encephalitogenic protein or peptide in CFA. The T cells are grown in tissue culture for several days and then injected intravenously into naive syngeneic recipients.

Mice are monitored and scored daily on a 0–5 scale for signals of the disease, including loss of tail muscle tone, wobbly gait, and various degrees of paralysis.

Oligonucleotide 17456 (SEQ ID NO. 173), a fully phosphorothioated analog of 18122, was compared to a saline control and a fully phosphorothioated oligonucleotide of random sequence (Oligonucleotide 17460). Results of this experiment are shown in FIG. 11.

As shown in FIG. 11, for all doses of oligonucleotide 17456 tested, there is a protective effect, i.e. a reduction of disease severity. At 0.2 mg/kg, this protective effect is greatly reduced after day 20, but at the higher doses tested, the protective effect remains throughout the course of the experiment (day 40). The control oligonucleotide gave results similar to that obtained with the saline control.

Example 19

Additional Antisense Oligonucleotides Targeted to Human B7-1

Additional oligonucleotides targeting human B7-1 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 21.

The human promonocytic leukaemia cell line, THP-1 (American Type Culture Collection, Manassas, Va.) was maintained in RPMI 1640 growth media supplemented with 10% fetal calf serum (FCS; Life Technologies, Rockville, Md.). A total of $1 \times 10^7$ cells were electroporated at an oligonucleotide concentration of 10 micromolar in 2 mm cuvettes, using an Electrocell Manipulator 600 instrument (Biotechnologies and Experimental Research, Inc.) employing 200 V, 1000 µF. Electroporated cells were then transferred to petri dishes and allowed to recover for 16 hrs. Cells were then induced with LPS at a final concentration of 1 µg/ml for 16 hours. RNA was isolated and processed as described in previous examples. Results are shown in Table 22.

Oligonucleotides 113492, 113495, 113498, 113499, 113501, 113502, 113504, 113505, 113507, 113510, 113511, 113513 and 113514 (SEQ ID NO: 228, 231, 234, 235, 237, 238, 240, 241, 243, 247, 248, 250 and 251) resulted in 50% or greater inhibition of B7-1 mRNA expression in this assay.

TABLE 21

Nucleotide Sequences of Human B7-1 Chimeric (deoxy gapped) Oligodeoxynucleotides

| ISIS NO. | NUCLEOTIDE SEQUENCE[1] (5' −> 3') | SEQ ID NO. | TARGET GENE NUCLEOTIDE CO-ORDINATES[2] | GENE TARGET REGION |
|---|---|---|---|---|
| 113489 | CCCTCCAGTGATGTTTACAA | 225 | 179 | 5' UTR |
| 113490 | GAAGACCCTCCAGTGATGTT | 226 | 184 | 5' UTR |
| 113491 | CGTAGAAGACCCTCCAGTGA | 227 | 188 | 5' UTR |
| 113492 | TTCCCAGGTGCAAAACAGGC | 228 | 234 | 5' UTR |
| 113493 | TGGCTTCAGATGCTTAGGGT | 229 | 299 | 5' UTR |
| 113494 | CCTCCGTGTGTGGCCCATGG | 230 | 316 | AUG |
| 113495 | GGTGATGTTCCCTGCCTCCG | 231 | 330 | Coding |

TABLE 21-continued

Nucleotide Sequences of Human B7-1 Chimeric (deoxy gapped) Oligodeoxynucleotides

| ISIS NO. | NUCLEOTIDE SEQUENCE[1] (5' -> 3') | SEQ ID NO. | TARGET GENE NUCLEOTIDE CO-ORDINATES[2] | GENE TARGET REGION |
|---|---|---|---|---|
| 113496 | GATGGTGATGTTCCCTGCCT | 232 | 333 | Coding |
| 113497 | AGGTATGGACACTTGGATGG | 233 | 348 | Coding |
| 113498 | GAAAGACCAGCCAGCACCAA | 234 | 384 | Coding |
| 113499 | CAGCGTTGCCACTTCTTTCA | 235 | 442 | Coding |
| 113500 | GTGACCACAGGACAGCGTTG | 236 | 454 | Coding |
| 113501 | AGATGCGAGTTTGTGCCAGC | 237 | 491 | Coding |
| 113502 | CCTTTTGCCAGTAGATGCGA | 238 | 503 | Coding |
| 113503 | CGGTTCTTGTACTCGGGCCA | 239 | 567 | Coding |
| 113504 | CGCAGAGCCAGGATCACAAT | 240 | 618 | Coding |
| 113505 | CTTCAGCCAGGTGTTCCCGC | 241 | 698 | Coding |
| 113506 | TAACGTCACTTCAGCCAGGT | 242 | 706 | Coding |
| 113507 | TTCTCCATTTTCCAACCAGG | 243 | 838 | Coding |
| 113508 | CTGTTGTGTTGATGGCATTT | 245 | 863 | Coding |
| 113509 | CATGAAGCTGTGGTTGGTTG | 246 | 943 | Coding |
| 113510 | AGGAAAATGCTCTTGCTTGG | 247 | 1018 | Coding |
| 113511 | TGGGAGCAGGTTATCAGGAA | 248 | 1033 | Coding |
| 113512 | TAAGGTAATGGCCCAGGATG | 249 | 1051 | Coding |
| 113513 | GGTCAGGCAGCATATCACAA | 250 | 1090 | Coding |
| 113514 | GCCCCTTGCTTCTGCGGACA | 251 | 1188 | 3' UTR |
| 113515 | AGATCTTTTCAGCCCCTTGC | 252 | 1199 | 3' UTR |
| 113516 | TTTGTTAAGGGAAGAATGCC | 253 | 1271 | 3' UTR |
| 113517 | AAAGGAGAGGGATGCCAGCC | 254 | 1362 | 3' UTR |
| 113518 | CAAGACAATTCAAGATGGCA | 255 | 1436 | 3' UTR |

[1]Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2]Co-ordinates from Genbank Accession No. M27533 to which the oligonucleotides are targeted.

TABLE 22

Inhibition of Human B7-1 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 113489 | 225 | 5' UTR | 122 | — |
| 113490 | 226 | 5' UTR | 183 | — |
| 113491 | 227 | 5' UTR | 179 | — |
| 113492 | 228 | 5' UTR | 27 | 73 |
| 113493 | 229 | 5' UTR | 488 | — |
| 113494 | 230 | AUG | 77 | 23 |
| 113495 | 231 | Coding | 43 | 57 |
| 113496 | 232 | Coding | 71 | 29 |
| 113497 | 233 | Coding | 78 | 22 |
| 113498 | 234 | Coding | 37 | 63 |
| 113499 | 235 | Coding | 25 | 75 |
| 113500 | 236 | Coding | 83 | 17 |
| 113501 | 237 | Coding | 36 | 64 |
| 113502 | 238 | Coding | 26 | 74 |
| 113503 | 239 | Coding | 65 | 35 |
| 113504 | 240 | coding | 46 | 54 |
| 113505 | 241 | Coding | 40 | 60 |
| 113506 | 242 | Coding | 105 | — |
| 113507 | 243 | Coding | 36 | 64 |
| 113508 | 245 | Coding | 117 | — |
| 113509 | 246 | Coding | 62 | 38 |
| 113510 | 247 | Coding | 43 | 57 |
| 113511 | 248 | Coding | 48 | 52 |
| 113512 | 249 | Coding | 73 | 27 |
| 113513 | 250 | Coding | 48 | 52 |
| 113514 | 251 | 3' UTR | 35 | 65 |
| 113515 | 252 | 3' UTR | 184 | — |
| 113516 | 253 | 3' UTR | 83 | 17 |
| 113517 | 254 | 3' UTR | 201 | — |
| 113518 | 255 | 3' UTR | 97 | 03 |

Example 20

Additional Antisense Oligonucleotides Targeted to Human B7-2

Additional oligonucleotides targeting human B7-2 were synthesized. Oligonucleotides were synthesized as uniformly phosphorothioate chimeric oligonucleotides having regions of five 2'-O-methoxyethyl (2'-MOE) nucleotides at the wings and a central region of ten deoxynucleotides. Oligonucleotide sequences are shown in Table 23.

The human promonocytic leukaemia cell line, THP-1 (American Type Culture Collection, Manassas, Va.) was maintained in RPMI 1640 growth media supplemented with 10% fetal calf serum (FCS; Life Technologies, Rockville, Md.). A total of $1 \times 10^7$ cells were electroporated at an oligonucleotide concentration of 10 micromolar in 2 mm cuvettes, using an Electrocell Manipulator 600 instrument (Biotechnologies and Experimental Research, Inc.) employing 200 V, 1000 µF. Electroporated cells were then transferred to petri dishes and allowed to recover for 16 hrs Cells were then induced with LPS and dibutyryl cAMP (500 μM) for 16 hours. RNA was isolated and processed as described in previous examples. Results are shown in Table 24.

Oligonucleotides ISIS 113131, 113132, 113134, 113138, 113142, 113144, 113145, 113146, 113147, 113148, 113149, 113150, 113153, 113155, 113157, 113158, 113159 and 113160 (SEQ ID NO: 256, 257, 259, 263, 267, 269, 270, 271, 272, 273, 274, 275, 278, 280, 282, 283, 284 and 285) resulted in 50% or greater inhibition of B7-2 mRNA expression in this assay.

TABLE 23

Nucleotide Sequences of Human B7-2 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 113131 | CGTGTGTCTGTGCTAGTCCC | 256 | 38 | 5' UTR |
| 113132 | GCTGCTTCTGCTGTGACCTA | 257 | 83 | 5' UTR |
| 113133 | TATTTGCGAGCTCCCCGTAC | 258 | 15 | 5' UTR |
| 113134 | GCATAAGCACAGCAGCATTC | 259 | 79 | 5' UTR |
| 113135 | TCCAAAAAGAGACCAGATGC | 260 | 97 | 5' UTR |
| 113136 | AAATGCCTGTCCACTGTAGC | 261 | 117 | 5' UTR |
| 113137 | CTTCAGAGGAGCAGCACCAG | 262 | 191 | Coding |
| 113138 | GAATCTTCAGAGGAGCAGCA | 263 | 195 | Coding |
| 113139 | CAAATTGGCATGGCAGGTCT | 264 | 237 | Coding |
| 113140 | GCTTTGGTTTTGAGAGTTTG | 265 | 257 | Coding |
| 113141 | AGGCTTTGGTTTTGAGAGTT | 266 | 259 | Coding |
| 113142 | GCTCACTCAGGCTTTGGTTT | 267 | 267 | Coding |
| 113143 | GGTCCTGCCAAAATACTACT | 268 | 288 | Coding |
| 113144 | AGCCCTTGTCCTTGATCTGA | 269 | 429 | Coding |
| 113145 | TGTGGGCTTTTTGTGATGGA | 270 | 464 | Coding |
| 113146 | AATCATTCCTGTGGGCTTTT | 271 | 473 | Coding |
| 113147 | CCGTGTATAGATGAGCAGGT | 272 | 595 | Coding |
| 113148 | ACCGTGTATAGATGAGCAGG | 273 | 596 | Coding |
| 113149 | TCATCTTCTTAGGTTCTGGG | 274 | 618 | Coding |
| 113150 | ACAAGCTGATGGAAACGTCG | 275 | 720 | Coding |
| 113151 | TGCTCGTAACATCAGGGAAT | 276 | 747 | Coding |
| 113152 | AAGATGGTCATATTGCTCGT | 277 | 760 | Coding |
| 113153 | CGCGTCTTGTCAGTTTCCAG | 278 | 787 | Coding |
| 113154 | CAGCTGTAATCCAAGGAATG | 279 | 864 | Coding |
| 113155 | GGGCTTCATCAGATCTTTCA | 280 | 1041 | Coding |
| 113156 | CATGTATCACTTTTGTCGCA | 281 | 1093 | Coding |
| 113157 | AGCCCCCTTATTACTCATGG | 282 | 1221 | 3' UTR |
| 113158 | GGAGTTACAGGGAGGCTATT | 283 | 1261 | 3' UTR |
| 113159 | AGTCTCCTCTTGGCATACGG | 284 | 1290 | 3' UTR |
| 113160 | CCCATAAGTGTGCTCTGAAG | 285 | 1335 | 3' UTR |

[1]Emboldened residues are 2'-methoxyethoxy residues (others are 2'-deoxy-). All 2'-methoxyethyl cytosines and 2'-deoxy cytosines residues are 5-methyl-cytosines; all linkages are phosphorothioate linkages.
[2]For ISIS# 113131 and 113132, co-ordinates are from Genbank Accession No. L25259, locus name "HUMB72A". For remaining oligonucleotides, co-ordinates are from Genbank Accession No. U04343, locus name "HSU04343".

TABLE 24

Inhibition of Human B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 113131 | 256 | 5' UTR | 13 | 87 |
| 113132 | 257 | 5' UTR | 17 | 83 |
| 113133 | 258 | 5' UTR | 214 | — |
| 113134 | 259 | 5' UTR | 27 | 73 |
| 113135 | 260 | 5' UTR | 66 | 34 |
| 113136 | 261 | 5' UTR | 81 | 19 |
| 113137 | 262 | Coding | 57 | 43 |
| 113138 | 263 | Coding | 12 | 88 |
| 113140 | 265 | Coding | 214 | — |
| 113141 | 266 | Coding | 126 | — |
| 113142 | 267 | Coding | 35 | 65 |
| 113143 | 268 | Coding | 118 | — |
| 113144 | 269 | Coding | 41 | 59 |
| 113145 | 270 | Coding | 46 | 54 |

TABLE 24-continued

Inhibition of Human B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 113146 | 271 | Coding | 32 | 68 |
| 113147 | 272 | Coding | 35 | 65 |
| 113148 | 273 | Coding | 23 | 77 |
| 113149 | 274 | Coding | 29 | 71 |
| 113150 | 275 | Coding | 19 | 81 |
| 113151 | 276 | Coding | 208 | — |
| 113152 | 277 | Coding | 89 | 11 |
| 113153 | 278 | Coding | 19 | 81 |
| 113154 | 279 | Coding | 63 | 37 |
| 113155 | 280 | Coding | 13 | 87 |
| 113156 | 281 | Coding | 83 | 17 |
| 113157 | 282 | 3' UTR | 13 | 87 |
| 113158 | 283 | 3' UTR | 20 | 80 |
| 113159 | 284 | 3' UTR | 43 | 57 |
| 113160 | 285 | 3' UTR | 09 | 91 |

Example 21

Human Skin Psoriasis Model

Animal models of psoriasis based on xenotransplantation of human skin from psoriatic patients are advantageous because they involve the direct study of affected human tissue. Psoriasis is solely a disease of the skin and consequently, engraftment of human psoriatic skin onto SCID mice allows psoriasis to be created with a high degree of fidelity in mice. One such model is that of Dam et al., *J. Invest. Dermatol.*, 1999, 113, 1082–1089. Briefly, keratome biopsies containing both dermis and epidermis are obtained from either clinically symptomless skin of psoriatic patients, or from psoriatic plaques. The keratomes are transferred to Earle's balanced Salt Solution (GIBCO, Grand Island, N.Y.) supplemented with 400 U pennicilin/ml, 400 ug streptomycin/ml, and 4 mg gentamicin/ml, and stored at 4° C. Immediately before orthotopic transplantation onto the flank of 6–8 week old anesthetized C.B-17 SCID mice (Taconic Farms, Germantown, N.Y.), human skin xenografts (1.7× 2.2×0.05 cm) are cut from the keratomes, and the grafts are secured to each SCID mouse with absorbable sutures and covered with dressings for 1 wk. Animals are randomized into treatment groups and test compound (in this case the human B7-1 oligonucleotide ISIS 113492 or the human B7-2 oligonucleotide ISIS 113131, or a combination of both oligonucleotides) is injected intradermally into the xenografts using a 30 G needle. Within 3–4 weeks the animals are sacrificed and 4 mm punch biopsies are taken from each xenograft. Biopsies are fixed in formalin for paraffin embedding and/or transferred to cryotubes and snap-frozen in liquid nitrogen and stored at −80° C.

What is claimed is:

1. An antisense compound 20 to 30 nucleobases in length targeted to a nucleic acid molecule encoding human B7, said compound comprising SEQ ID NO: 256.

2. The antisense compound of claim 1 which is an antisense oligonucleotide.

3. The antisense compound of claim 2 which is modified.

4. The antisense compound of claim 2 which comprises at least one modified internucleoside linkage.

5. The antisense compound of claim 4 wherein the modified internucleoside linkage is a phosphorothioate linkage.

6. The antisense compound of claim 5 wherein every internucleoside linkage is a phosphorothioate linkage.

7. The antisense compound of claim 2 which comprises at least one modified sugar moiety.

8. The antisense compound of claim 7 wherein the modified sugar moiety is a 2'-O-methoxyethyl sugar moiety.

9. The antisense compound of claim 2 which comprises at least one modified nucleobase.

10. The antisense compound of claim 9 wherein the modified nucleobase is a 5-methylcytosine.

11. The antisense compound of claim 9 wherein nucleobases 1–5 and 16–20 comprise a 2'-O-methoxyethyl modification.

12. The antisense compound of claim 9, wherein each cytidine residue comprises a 5-methyl modification.

13. The antisense compound of claim 1, that is a pharmaceutically acceptable salt.

14. The antisense compound of claim 13 that is a sodium salt.

15. A composition comprising the antisense compound of claim 1 in combination with a carrier or diluent.

16. The composition of claim 15 further comprising a colloidal dispersion system.

17. The composition of claim 15 further comprising an anti-inflammatory or immunosuppressive agent.

18. A composition comprising an antisense compound consisting of SEQ ID NO: 256.

19. The composition of claim 18, wherein every internucleoside linkage of the antisense compound is a phosphorothioate linkage.

20. The composition of claim 18, wherein each cytidine residue of the antisense compound comprises a 5-methyl modification.

21. The composition of claim 18, wherein the antisense compound is a pharmaceutically acceptable salt.

22. The composition of claim 21 wherein the pharmaceutically acceptable salt is a sodium salt.

23. The composition of claim 18 further comprising a pharmaceutically acceptable carrier or diluent.

24. The composition of claim 21 further comprising a pharmaceutically acceptable carrier or diluent.

25. A composition comprising an antisense compound comprising SEQ ID NO: 256, wherein every internucleoside linkage is a phosphorothioate linkage, and nucleobases 1–5 and 16–20 comprise a 2'-O-methoxyethyl modification.

26. The composition of claim 25, wherein each cytidine residue of the antisense compound comprises a 5-methyl modification.

27. The composition of claim 26, wherein the antisense compound is a pharmaceutically acceptable salt.

28. The composition of claim 27, wherein the pharmaceutically acceptable salt is a sodium salt.

29. The composition of claim 25, further comprising a pharmaceutically acceptable carrier or diluent.

30. A composition comprising an antisense compound consisting of SEQ ID NO: 256, wherein every internucleoside linkage is a phosphorothioate linkage, and nucleobases 1–5 and 16–20 comprise a 2'-O-methoxyethyl modification.

31. The composition of claim 30, wherein each cytidine residue of the antisense compound comprises a 5-methyl modification.

32. The composition of claim 31, wherein the antisense compound is a pharmaceutically acceptable salt.

33. The composition of claim 32, wherein the pharmaceutically acceptable salt is a sodium salt.

34. The composition of claim 30, further comprising a pharmaceutically acceptable carrier or diluent.

35. The composition of claim 32, further comprising a pharmaceutically acceptable carrier or diluent.

36. A composition comprising an antisense compound consisting of SEQ ID NO: 256, wherein every internucleoside linkage is a phosphorothioate linkage, nucleobases 14 and 15–18 comprise a 2'-O-methoxyethyl modification, and cytidine residues at positions 5 and 10 comprise a 5-methyl modification.

37. The composition of claim 36, wherein the compound is a pharmaceutically acceptable salt.

38. The composition of claim 37, wherein the pharmaceutically acceptable salt is a sodium salt.

39. The composition of claim 36, further comprising a pharmaceutically acceptable carrier or diluent.

40. The composition of claim 37, further comprising a pharmaceutically acceptable carrier or diluent.

\* \* \* \* \*

UNITED STATES PATENT AND TRADEMARK OFFICE
CERTIFICATE OF CORRECTION

| | | |
|---|---|---|
| PATENT NO. | : 7,115,580 B1 | Page 1 of 1 |
| APPLICATION NO. | : 09/980953 | |
| DATED | : October 3, 2006 | |
| INVENTOR(S) | : C. Frank Bennett et al. | |

It is certified that error appears in the above-identified patent and that said Letters Patent is hereby corrected as shown below:

Column 148, Claim 36, line 43, please delete "14" and insert therefore --1-4--.

Signed and Sealed this

Fifth Day of December, 2006

JON W. DUDAS
*Director of the United States Patent and Trademark Office*